US012667568B2

(12) United States Patent
Li et al.

(10) Patent No.: US 12,667,568 B2
(45) Date of Patent: Jun. 30, 2026

(54) COMPOSITIONS AND METHODS FOR THE TREATMENT AND DIAGNOSIS OF CANCER

(71) Applicants: The General Hospital Corporation, Boston, MA (US); BioVentures, LLC, Little Rock, AR (US)

(72) Inventors: Hong-yu Li, Little Rock, AR (US); Wei Yan, Little Rock, AR (US); Li Lan, Boston, MA (US)

(73) Assignees: The General Hospital Corporation, Boston, MA (US); Bio Ventures, LLC, Little Rock, AR (US)

( * ) Notice: Subject to any disclaimer, the term of this patent is extended or adjusted under 35 U.S.C. 154(b) by 570 days.

(21) Appl. No.: 18/040,940

(22) PCT Filed: Aug. 9, 2021

(86) PCT No.: PCT/US2021/045211
§ 371 (c)(1),
(2) Date: Feb. 7, 2023

(87) PCT Pub. No.: WO2022/032224
PCT Pub. Date: Feb. 10, 2022

(65) Prior Publication Data

US 2024/0000784 A1 Jan. 4, 2024

Related U.S. Application Data

(60) Provisional application No. 63/062,618, filed on Aug. 7, 2020.

(51) Int. Cl.
*A61K 31/517* (2006.01)
*A61K 31/502* (2006.01)
*A61K 33/243* (2019.01)
*A61P 35/00* (2006.01)

(52) U.S. Cl.
CPC .......... *A61K 31/517* (2013.01); *A61K 31/502* (2013.01); *A61K 33/243* (2019.01); *A61P 35/00* (2018.01)

(58) Field of Classification Search
CPC .. A61K 31/517; A61K 31/502; A61K 33/243; A61P 35/00
See application file for complete search history.

(56) References Cited

U.S. PATENT DOCUMENTS

| | | | | |
|---|---|---|---|---|
| 2011/0301059 | A1 | 12/2011 | Pyeon et al. | |
| 2014/0235486 | A1 | 8/2014 | Chapman et al. | |
| 2015/0057243 | A1 | 2/2015 | Zhou et al. | |
| 2024/0066033 | A1 * | 2/2024 | Li | A61K 31/517 |

FOREIGN PATENT DOCUMENTS

| | | | |
|---|---|---|---|
| KR | 101539106 | B1 | 7/2015 |
| WO | 2009015294 | A1 | 1/2009 |

OTHER PUBLICATIONS

Su, et al.; Cancer Cell, v38, pp. 79-96; 2020 (Year: 2020).*
Algret, R. et al., Molecular Architecture and Function of the SEA Complex, a Modulator of the TORC1 Pathway, Molecular & Cellular Proteomics, 2014, 13(11):2855-2870.
Cully, M., RNA Methyltransferase Inhibitor Reduces AML, Nature Reviews Drug Discovery, 2020, 19:510.
Da Ines, O. et al., Meiotic Recombination in Arabidopsis is Catalysed by DMC1, with RAD51 Playing a Supporting Role, PLOS Genetics, 2013, 9(9):e1003787, pp. 1-11.
Fridy, P. et al., A Robust Pipeline for Rapid Production of Versatile Nanobody Repertoires, Nature Methods, 2014, 11 (12):1253-1260.
Lan, L. et al., The ACF1 Complex is Required for DNA Double-Strand Break Repair in Human Cells, Molecular Cell, 2010, 40(6):976-987.
Lan, L. et al., Novel Method for Site-Specific Induction of Oxidative DNA Damage Reveals Differences in Recruitment of Repair Proteins to Heterochromatin and Euchromatin, Nucleic Acids Research, 2014, 42(4):2330-2345.
Li, M. et al., Integrated Analysis of DNA Methylation and Gene Expression Reveals Specific Signaling Pathways Associated with Platinum Resistance in Ovarian Cancer, BMC Medical Genomics, 2009, 2:34, pp. 1-13.
Pinder, J. et al., Nuclear Domain 'Knock-in' Screen for the Evaluation and Identification of Small Molecule Enhancers of CRISPR-based Genome Editing, Nucleic Acids Research, 2015, 43(19):9379-9392.
Pubchem, Substance Record SID 312548953, Available Mar. 22, 2016, 6 pages.
Rosace, D. et al., Emerging Roles of Novel Small Non-Coding Regulatory RNAs in Immunity and Cancer, RNA Biology, 2020, 17(8):1196-1213.
Schaefer, M. et al., Azacytidine Inhibits RNA Methylation at DNMT2 Target Sites in Human Cancer Cell Lines, Cancer Research, 2009, 69(20):8127-8132.
Schaefer, M. et al., Solving the Dnmt2 Enigma, Chromosoma, 2010, 119:35-40.
Shi, Y. et al., A Strategy for Dissecting the Architectures of Native Macromolecular Assemblies, Nature Methods, 2015, 12(12):1135-1138.
Subramaniam, D. et al., DNA Methyltransferases: A Novel Target for Prevention and Therapy, Frontiers in Oncology, 2014, vol. 4, Article 80, pp. 1-13.
Tyanova, S. et al., The MaxQuant Computational Platform for Mass Spectrometry-Based Shotgun Proteomics, Nature Protocols, 2016, 11(12):2301-2319.
Wang, H. et al., Promotive Role of Recombinant HE4 Protein in Proliferation and Carboplatin Resistance in Ovarian Cancer Cells, Oncology Reports, 2015, 33:403-412.

(Continued)

*Primary Examiner* — Jeffrey S Lundgren
*Assistant Examiner* — W. Justin Youngblood
(74) *Attorney, Agent, or Firm* — QUARLES & BRADY LLP

(57) ABSTRACT

Disclosed herein are RNA methyltransferase inhibitors and methods of using the same. The inhibitors may be used in a method for the treatment of a subject in need of a treatment for a cancer by administering an effective amount of an RNA methyltransferase inhibitor to the subject.

20 Claims, 41 Drawing Sheets

Specification includes a Sequence Listing.

(56) References Cited

OTHER PUBLICATIONS

Wu, C. et al., SYCP2 Expression is a Novel Prognostic Biomarker in Luminal A/B Breast Cancer, Future Oncology, 2019, 15(8):817-826.
PCT International Search Report and Written Opinion, PCT/US2021/045203, Dec. 23, 2021, 12 pages.
PCT International Search Report and Written Opinion, PCT/US2021/045204, Dec. 23, 2021, 15 pages.
PCT International Search Report and Written Opinion, PCT/US2021/045211, Dec. 23, 2021, 12 pages.

* cited by examiner

Relative survival rate
1
0.5
0.25
0.125
MCF-7
U2OS
SKOV3
Cisplatin
siCtrl
siTRDMT1
**
**
***

TRDMT1
1
67
167
275
391
a.a. 1-391
G155V
SAM BD
Catalytic Motif
Linker
DNA/RNA BD TRDMT1 KO
+WT
+C79A
+G155V
TRDMT1
β-Actin TRDMT1 KO
WT
G155V
MG132
-
+
WB:Ub
IP:GFP
GFP-TRDMT1
Tubulin
Input

| | Unique peptides | | | |
|---|---|---|---|---|
| | 150mM | | 300mM | |
| Protien | Crontrol | GFP-TRDMT1 | Crontrol | GFP-TRDMT1 |
| TRIM28 | 3 | 10 | 10 | 21 |
| TRIM21 | 0 | 8 | 7 | 4 |
| HUWE1 | 0 | 0 | 1 | 0 |

| Cell line | *BRCA1* status |
|---|---|
| HCC1954 | p.V1810fs |
| HCC1937 | p.Q1756fs |

| Variables | | Number(n=16) |
|---|---|---|
| Sex | Female | 16(100%) |
| Subtype | Luminal | 7(43%) |
| | TNBC | 8(50%) |
| | Unknown | 1(7%) |

| | RDDR score | Protein S |
|---|---|---|
| HCC1937 (HRD) | +++ | 10.7 |
| HCC1500 | ++++ | 182 |
| BT549 | ++ | 9.3 |
| MCF7 | ++ | 5.52 |
| MDAMB468 | ++ | 5.41 |
| BJ | -/+ | 0.55 |

COMPOSITIONS AND METHODS FOR THE TREATMENT AND DIAGNOSIS OF CANCER

CROSS-REFERENCE TO RELATED APPLICATION

This application represents the U.S. national stage entry of International Application No. PCT/US2021/045211 filed Aug. 9, 2021, which claims benefit of priority to U.S. Patent Application Ser. No. 63/062,618, filed Aug. 7, 2020. The contents of these applications are incorporated herein by reference in their entirety.

REFERENCE TO A SEQUENCE LISTING

This application is being filed electronically via EFS-Web and includes an electronically submitted Sequence Listing in .txt format. The .txt file contains a sequence listing entitled "12514103640ST25.txt" created on Aug. 9, 2021 and is 3,595 bytes in size. The Sequence Listing contained in this .txt file is part of the specification and is hereby incorporated by reference herein in its entirety.

BACKGROUND OF THE INVENTION

Cancer drugs targeting the DNA damage response (DDR), including DNA-damaging drugs, such as cisplatin, bleomycin, or Mitomycin C, and DNA repair inhibitors, such as PARPi, ATRi, or TopIi, kill cancer cells by exploiting their DNA repair defects or genomic instability. These DDR-targeted drugs directly or indirectly induce DNA double-strand breaks (DSBs), a lethal form of DNA damage. Despite the efficacy of these drugs in the clinic, drug resistance is a common problem. Biomarkers of resistance to DDR-targeted drugs and strategies to overcome the resistance are much needed for improving cancer therapy. Homologous Recombination (HR) is one of the DNA repair pathways critical for repairing DSBs. Breast, ovarian, and some other cancers with BRCA1/2 mutations are defective in HR and highly sensitive to PARPi. Unfortunately, only around 10% of cancer patients carry BRCA1/2 mutations, presenting a challenge to predicting the response of the majority of cancer patients to PARPi and other DDR-targeted drugs. Overall, the lack of biomarkers for sensitivity or resistance to DDR-targeted drugs has been a major obstacle for the treatment of cancer patients. Moreover, both preexisting and acquired resistance to DDR-targeted drugs also limit the efficacy of these drugs in patients. As a result, there is a need for better methods to identify and treat patients suffering from cancer that can benefit from cancer drugs that target DDR.

BRIEF SUMMARY OF THE INVENTION

Disclosed herein are RNA methyltransferase inhibitors and methods of using and making the same. One aspect of the technology provides for a method for the treatment of a subject in need of a treatment for a cancer. The method may comprise administering an effective amount of an RNA methyltransferase inhibitor to the subject. In some embodiments, the RNA methyltransferase inhibitor is a compound of formula

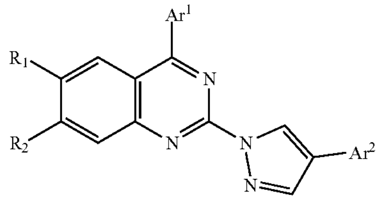

or a pharmaceutically acceptable salt thereof, wherein $R_1$ and $R_2$ are independently selected from hydrogen; an unsubstituted or substituted, unbranched or branched, saturated or unsaturated, acyclic or cyclic $C_1$-$C_6$ alkyl; hydroxide; an unsubstituted or substituted, unbranched or branched, saturated or unsaturated, acyclic or cyclic $C_1$-$C_6$ alkoxy; an unsubstituted or substituted, unbranched or branched, saturated or unsaturated, acyclic or cyclic $C_1$-$C_6$ amino; an unsubstituted or substituted aryl; or an unsubstituted or substituted heteroaryl; and wherein $Ar^1$ and $Ar^2$ are independently selected from an unsubstituted or substituted aryl or an unsubstituted or substituted heteroaryl. In some embodiments, $R_1$ and $R_2$ are independently the unsubstituted or substituted, unbranched or branched, saturated or unsaturated, acyclic or cyclic $C_1$-$C_6$ alkoxy; $Ar^1$ is the unsubstituted heteroaryl; and/or $Ar^2$ is the substituted aryl. In some embodiments, $R_1$ and $R_2$ are methoxy; $Ar^1$ is an unsubstituted thiopene; and/or $Ar^2$ is a sulfonyl-substituted phenyl.

In some embodiments, the RNA methyltransferase inhibitor, or a pharmaceutically acceptable salt thereof, is selected from the group consisting of 6,7-dimethoxy-4-phenyl-2-(4-(pyridin-3-yl)-1H-pyrazol-1-yl)quinazoline, 6,7-dimethoxy-2-(4-(pyridin-3-yl)-1H-pyrazol-1-yl)-4-(quinolin-8-yl)quinazoline, 5-(6,7-dimethoxy-2-(4-(pyridin-3-yl)-1H-pyrazol-1-yl)quinazolin-4-yl)-N,N-dimethylpyridin-2-amine, 6,7-dimethoxy-4-(pyridin-3-yl)-2-(4-(pyridin-3-yl)-1H-pyrazol-1-yl)quinazoline, 1-(4-(6,7-dimethoxy-2-(4-(pyridin-3-yl)-1H-pyrazol-1-yl)quinazolin-4-yl)phenyl)ethanone, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(pyridin-3-yl)quinazoline, 4-(furan-3-yl)-6,7-dimethoxy-2-(4-(4-(methylsulfonyl)phenyl)-1H-pyrazol-1-yl)quinazoline, 6,7-dimethoxy-2-(4-(4-(methylsulfonyl)phenyl)-1H-pyrazol-1-yl)-4-(thiophen-3-yl)quinazoline, 6,7-dimethoxy-2-(4-(4-(methylsulfonyl)phenyl)-1H-pyrazol-1-yl)-4-(p-tolyl)quinazoline, 2-(4-(4-(methylsulfonyl)phenyl)-1H-pyrazol-1-yl)-4-(thiophen-3-yl)quinazoline, 7-(4-ethylpiperazin-1-yl)-2-(4-(4-(methylsulfonyl)phenyl)-1H-pyrazol-1-yl)-4-(thiophen-3-yl)quinazoline, 4-(1-(6,7-dimethoxy-4-(thiophen-3-yl)quinazolin-2-yl)-1H-pyrazol-4-yl)-N-(2-(dimethylamino)ethyl)benzenesulfonamide, 6,7-dimethoxy-4-(4-((4-methylpiperazin-1-yl)sulfonyl)phenyl)-2-(4-(4-(methylsulfonyl)phenyl)-1H-pyrazol-1-yl)quinazoline, and 6,7-dimethoxy-4-(3-methoxyphenyl)-2-(4-(4-(methyl sulfonyl)phenyl)-1H-pyrazol-1-yl)quinazoline. In an embodiment, the RNA methyltransferase inhibitor is

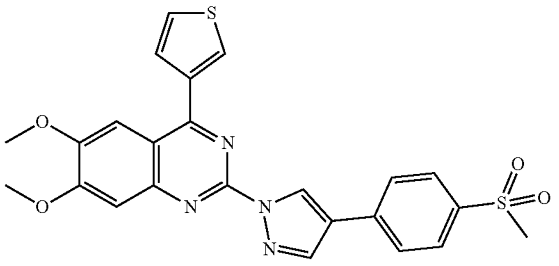

or a pharmaceutically acceptable salt thereof.

In some embodiments, the cancer has upregulated SYCP2 expression or upregulated SYCP2 activity, the cancer is a homologous recombination (HR) deficient cancer, the cancer is a cancer resistant to therapy with a DNA damaging agent, or any combination thereof. In some embodiments, the cancer is a breast cancer, ovarian cancer, esophageal cancer, stomach cancer, colon cancer, lung cancer, skin cancer, prostate cancer, head and neck cancer, bone cancer, kidney cancer, urinary tract cancer, bladder cancer, or pancreatic cancer. In particular embodiments, the breast cancer is a BRCA proficient breast cancer.

These and other aspects of the invention will be further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

(FIG. 1A) The survival rate of MCF-7, U2OS, and SKOV3 cells pre-treated with siTRDMT1 or siCtrl after 1 μM cisplatin treatment (n=3, Mean±SD). (FIG. 1B) Schematic diagram of TRDMT1 and TRDMT1$^{G155V}$ mutant. (FIG. 1C) WB of TRDMT1 in GFP-tagged TRDMT1$^{WT}$, TRDMT1 $C_{79A}$ or TRDMT1$^{G155V}$ stably expressed TRDMT1 KO 293 cells. (FIG. 1D) The ubiquitination level of TRDMT1 in GFP-TRDMT1$^{G155V}$ or TRDMT1$^{WT}$ stably expressed 293 cells. Indicated cell lines were treated with or without 20 μM MG132 for 6 h before protein extraction. (FIG. 1E) WB of TRDMT1 in U2OS cells treated with 100 μg/ml CHX with or without 20 μM MG132 for the indicated time. (FIG. 1F) Dot blot analysis of $m^5C$ in mRNA of TRDMT1 KO 293 cells with stable expression of GFP-tagged TRDMT1$^{WT}$, TRDMT1$^{C79A}$ or TRDMT1$^{G155V}$ γ-H2AX staining in GFP-tagged TRDMT1$^{WT}$ or TRDMT1$^{G155V}$ transfected TRDMT1 KO U2OS-TRE cells. Cells were irradiated with 6 Gy IR and stained with γ-H2AX at the indicated time point, numbers of γ-H2AX foci in each cell (FIG. 1G) and the frequency of 100 cells with γ-H2AX foci (FIG. 1H) were counted in each experiment (n=3, Mean±SD).

(FIG. 2A) GFP-TRDMT1 stably expressed 293 cells were immunoprecipitated by anti-GFP and washed with sodium chloride concentrations at 150 mM or 300 mM. E3 ligases identified from mass spectrometry by pulling down by GFP-TRDMT1 under each wash condition and numbers of unique peptides of E3 ligases are indicated. (FIG. 2B) 293 TRDMT1 KO cells stably expressing GFP-tagged TRDMT$^{WT}$ and TRDMT1$^{G155V}$ were pulled with anti-GFP and immunoblotted with anti-ubiquitin. Cells were treated with 20 μM MG132 for 6 h before pulling down. (FIG. 2C) IP of GFP-TRDMT1 and TRIM28. 293 Cells stably expressing GFP-TRDMT1 were pulled down by anti-GFP and immunoblotted with anti-TRIM28. (FIG. 2D) U2OS-TRE cells co-transfected TA-KR/TA-Cherry/tetR-KR/tetR-Cherry with or without GFP-TRDMT1 plasmid were exposed to light for 30 min for KR activation and allowed to recover for 30 min before fixation. Recruitment of TRIM28 with anti-TRIM28 antibody at each indicated site is shown. Quantification of the frequency of cells in 50 cells with GFP-TRDMT1 or TRIM28 foci from three independent experiments (n=3, Mean±SD). (FIG. 2E) WB of TRDMT1 and TRIM28 and the survival rate of WT cells and TRDMT1 KO U2OS cells with or without siTRIM28 after 2 Gy IR treatment.

(FIG. 3A) U2OS-TRE cells transfected with TA-KR and GFP-TRDMT1 following with treatment described in 2D. The fold increase of intensity of GFP-TRDMT1 WT or GFP-TRDMT1$^{G155V}$ at sites of TA-KR was shown (n=3, 10 cells per replicate, Mean±SD). (FIG. 3B) TRDMT1 KO U2OS cells were transfected with TA-KR and GFP-TRDMT1$^{WT}$/GFP-TRDMT1$^{G155V}$ following with treatment with 2D and stained for $m^5C$ and RAD51 or RAD52. Quantification of RAD51 and RAD52 at TA-KR sites. (n=3, 50 cells per replicate, Mean±SD).

(FIG. 4A) 293 TRDMT1 KO cells were transfected with GFP-tagged TRDMT1$^{WT}$, TRDMT1$^{G155V}$ TRDMT1$^{K251R}$ and TRDMT1$^{G155V+K251R}$ mutants, respectively. Cells were pulled with anti-GFP and immunoblotted with anti-Ubi. (FIG. 4B) The survival rate of U2OS-TRE TRDMT1 KO cells and U2OS-TRE TRDMT1 KO cells transfected with TRDMT1$^{WT}$, TRDMT1$^{G155V}$ TRDMT1$^{K25WR}$ after Cisplatin treatment at the indicated dose. (FIG. 4C) Quantification of RAD52 (n=3, 50 cells per replicate, Mean±SD) and RAD51 at TA-KR sites. (n=20, Mean±SD).

(FIG. 4E) WB of the U2OS cells transfected with TRDMT1 mutants in FIG. 4B.

(FIG. 5A) Lv-shTRDMT1 or Lv-NC transfected SKOV3 cells were subcutaneously injected into BALB/c nude mice, a week after injection, Cisplatin (5 mg/kg) or saline was injected into the center of the xenograft tumors twice per week for 3 consecutive weeks. (FIG. 5B) Representative images of tumors in xenografts transfected with LV-shTRDMT1/LV-NC with saline or Cisplatin treatment. (FIG. 5C) Tumor size of SKOV3 subcutaneous xenograft tumors (n=6, Mean±SD). (FIG. 5D)

WB for TRDMT1 in tumor tissues collected from mice in each group (Tissues from six tumors in the same group were mixed into one sample). (FIG. 5E) IHC of TRDMT1 and KI-67 expression in ovarian cancer tissues of patients who were platinum-sensitive (PFS>6) and —resistant (PFS<6) Staining was assessed and scored on a scale of 0 (<5% staining) to 4 (>75% staining) in G. Quantification of IHC staining (n=38, PFS>6, n=24; PFS<6, n=14) was shown.

(FIG. 6A) SCE WT cells were transfected with TA-KR and were cultured with 2.5 μM/L compound YW-1842 or not for 6 hours, $m^5C$ (n=3, 50 cells per replicated, Mean±SD) was stained and quantified. DR-GFP (FIG. 6B) or EJ5-GFP (FIG. 6C) cells were pre-treated with 2.5 μM/L compound YW-1842 for 6 h or TRDMT1 siRNA for 48 h, or DMSO. Then the cells were transfected with NLS-I-SceI plasmid to induce DSB. The efficiency of HR (FIG. 6B) or NHEJ (FIG. 6C) was analyzed by flow-cytometry (n=3, Mean f SD). (FIG. 6D) After seeding, MCF-7, HCC1954, and HCC1937 cells were pre-treated with or without 2.5 μM/L compound YW-1842 for 6 h, then cultured with chemotherapy drugs (1 μM/L Cisplatin; 1 μM/L ATRi AZ20; 10 μM/L ATMi KU55933; 1 μM/L PARPi Olaparib for 10 days. The survival rate of these cells was analyzed (n=3, Mean±SD). (FIG. 6E) TRDMT1 KO U2OS cells were transfected with GFP-$TRDMT1^{WT}$ or GFP-$TRDMT1^{G155V}$ with or without 2.5 μM/L compound YW-1842, the survival rate of these cells after IR or Cisplatin was shown (n=3, Mean±SD).

(FIG. 6F) U2OS or MCF7 cells were treated with or without compound YW-1842 at the indicated concentration. The survival rate of these cells was shown (n=3, Mean±SD). (FIG. 6G) SCE WT cells were transfected with TA-KR and were cultured with 2.50/1 YW-1842 or not for 6 hours, γ-H2AX (n=3, 50 cells per replicated, Mean±SD) were stained and quantified.

(FIG. 7A) IC50 of four DDR drugs (Olaparib, Cisplatin, Temozolomide and Camptothecin) and RNA seq of breast cancer cell line (n=49) from GDSC and CCLE, respectively were used for Pearson correlation analysis. Cluster was evaluated by PCA. Dimensionally reduced plot is shown the correlated genes in which Pearson correlation coefficients value >0.4, p value <0.05 from each indicated drug group. Venn plot of correlated genes from each indicated drug treated group are shown on the right. Plot showed 152 common hits. (FIG. 7B) Scheme of screening using DDR derived bioinformatical analysis and cancer relevant gene expression are shown on top. Plot of 152 common top hits of the results in FIG. 1A are shown. The y-axis indicates the mean r value of the correlation results of using the four DDR drugs and the x-axis indicates the expression of the correlated genes in breast cancer over the baseline level. Baseline is expression median value in normal tissue. Top seven hits highly expressed in breast cancers are listed. (FIG. 7C) Expression of SYCP2 in 29 types of tumors. Expression data was obtained from TCGA and GTEx. Data from TCGA was transferred to TPM to normalize gene expression. (FIG. 7D) Expression of SYCP2 in breast cancer compared to normal breast tissues using TCGA database (FIG. 7E) Expression level analysis of SYCP2 in different cancer cell lines using the data from CCLE. (FIG. 7F) Median expressions of meiosis genes and cohesion complex genes in 29 types tumors and the normal tissue from TCGA database.

(FIG. 8A) The 2D plot of correlation r value between SYCP2 expression and IC50 of Cisplatin, Etoposide and TOPI inhibitor in breast cancer cell lines using TCGA database is shown on the left. 3D plot of correlation r value between SYCP2 expression and IC50 of Olaparib, Recuparib, and Telozoparib in breast cancer cell lines is shown on the right. The corresponding 2D plot and the calculated r-value/p-value for each drug are shown and indicated. (FIG. 8B) Pearson correlation between expression of SYCP2 and IC50 of 251 drugs (from GDSC) involved in indicated pathways in breast cancer cell lines. RNA seq data of cell lines were from CCLE. Patients' expression data were from TCGA. p values in correlation study were determined by using Pearson correlation analysis. (FIG. 8C) Fold changes of expression levels of SYCP2 family in PAPRi sensitive and PARPi resistant subclones from the dataset GSE86394 in GEO database.

(FIG. 9A) Cell survival rate of HeLa and MDAMB231 via colony forming assay with the treatment of 211M, 4 μm, 6 μM, 8 μM, 16 μM of Olaparib (n=3, mean+/−S.D.). Western blot of SYCP2 overexpression in HeLa and MDA-MB-231 is shown in the left. (FIG. 9B) Cell survival rate of HeLa via colony forming assay with the treatment of 1 μM, 2 μm, 3 μM of Olaparib (n=3, mean+/−S.D.). Western blot of SYCP2 knockdown in Hela is shown in the left. (FIG. 9C) Scheme of Xenograft design using intraperitoneal injection of MBA-MD-231 into successful developed mouse model with virus-associated SYCP2 knockdown and control groups is shown in the left. PARPi was injected every 2 days after day 7. The graph is shown the recorded tumor size of each tested group with PARPi treatment or saline at each treatment day. (FIG. 9D). Numbers of SYCP2 IR induced foci (IRIF) colocalizing with γH2AX in MDAMB231 and HeLa cells. Cells were fixed and counted for foci numbers after 2 Gy IR followed up indicated recovery time (t=0 hr, 12 hr, 24 hr, and 48 hr) (n=30, mean+/−S.D). (FIG. 9E). Scheme of DR-GFP reporter HR assay (left). Relative HR frequency in U2OS DR-GFP cells expressed with SYCP2-OE, and siBRCA1 or siSYCP2. (FIG. 9F). Schematic mechanism of HR repair after DSBs is shown at left. Kinetics of DDR of GFP-NBS1, GFP-RPA, and GFP-SYCP2 in U2OS cells after laser microirradiation. Fold increase of mean intensity at sites of irradiation compared to mean intensity of nucleus expression is quantified (n=5, mean+/−SD). (FIG. 9G). Numbers of RAD51 IRIF in siCtrl and siSYCP2 treated MDAMB231 and U2OS cells after 2 Gy IR and 1 hour recovery were counted (n=20, +/SD).

(FIG. 10A) The schematic mechanism of HR in the absence of BRCA1/2 for RAD51 loading with the help of SYCP2. RAD51 IRIF in BRCA1 mutant breast cancer cell lines after 2 Gy IR and 1 hour recovery with or without siSYCP2. Numbers of RAD51 foci per cell in siCtrl and siSYCP2 were quantified (n=20). The frameshift mutation of BRCA1 in cell line HCC1954 and HCC1937 is listed in the right. (FIG. 10B) The frequency of BRCA1 and SYCP2 IRIF colocalizing with γ-H2AX in U2OS cells after 2 Gy IR and recovery of 1 hour. Western blot of BRCA1 and SYCP2 knockdown and RAD51 expression level was shown in the left. (FIG. 10C) Comparison of SYCP2 RNA expression (CCLE database) in BRCA1/2 mutant and wildtype breast cancer cell lines. The analysis is normalized to Fragments Per Kilobase Million (FPKM). (FIG. 10D) Plot of correlation between SYCP2 expression and IC50 of Olaparib in groups of BRCA WT vs. mutant cells (left), high BRCA1 vs. low BRCA1 (right). p values and r values were determined by using Pearson correlated analysis. This analysis is based on TCGA database. (FIG. 10E) Cell survival rate of six breast cancer cell lines (ZR-75-30, MCF7, HCC-1954, HCC-1937, MDA-MB-468 and MDA-MB-231) via colony forming assay with the treatment of 0 μM, 0.1 μm, 1Mm, 10 μM and 100 μM of Olaparib. Three independent experiments were done (mean+/−S.D.). The six cell lines are categorized by the expression levels of SYCP2 and BRCA.

FIGS. 11A-11I show SYCP2 binds RAD51 and promotes HR through the KR domain. (FIG. 11A) U2OS-TRE cells transfected with TA-KR under the siCtrl/siSYCP2/siBRCA1/siBRCA2 transfected conditions were light activated for 15 min, recovered for 30 min, and stained with anti-RAD51. Fold increase of RAD51 foci at sites of KR compared background was quantified (n=10, mean+/−SD). The schematic mechanism of SYCP2 in TC-HR is shown on the right. (FIG. 11B) Scheme of SYCP2 deletion and truncation constructs ΔM1, M1 and M2. (The homologies of SYCP2L region are indicated in gray.) The fragments are labeled in the amino acid order. U2OS cells overexpressed with different SYCP2 fragments shown at top were transfected with CRISPR/Cas9-sg LMNA, LMNA-mClover, and mCherry plasmids. The fraction of mClover-positive cells in the mCherry-positive population were counted (n=30, Mean±SD). GFP-M1 and other deletion constructs were transfected into U2OS cells. (FIG. 11C) Immunoprecipitation was done with G-protein beads with conjugated anti-GFP in GFP-M1/vector transfected 293 cells. The RAD51 levels was incubated with anti-RAD51(ab63801). (FIG. 11D) Schematic of three mutants design of changing KR residues in M1 domain of SYCP2 was shown on top. Immunoprecipitation results of using G-protein beads with conjugated anti-GFP in 2KRAA/5KRAA mutants transient transfected 293 cells were shown below. The RAD51 levels was incubated with anti-RAD51(ab63801). (FIG. 11E) Numbers of IRIF of M1 wildtype and three mutants transfected U2OS cells after 2 Gy IR and 1 hour recovery were counted in the left (n=20, +/−SD). (FIG. 11F) The representative images of recruitment of GFP-M1, 2KRAA, 5KRAA and 11KRAA before and after 100 msec laser microirradiation in U2OS cells. (FIG. 11G) The recruitment of M1 wildtype and three mutants at TA-KR sites. The transfected cells were light activated for 10 minutes and recovered for 30 minutes. Fold increase of the foci at sites of KR compared background was quantified (n=10, mean+/−SD). (FIG. 11H) mClover-HR reporter (CRISPR/Cas9-sg LMNA, LMNA-mClover) showed the HR frequency of M1 domain and three mutants. (n=20, +/−SD).

(FIG. 12A) Expression of SYCP2 in breast cancer samples from TCGA database (n=1217). The corresponding status of Tumor stages, pathology stages, lymph node stage and Her2 levels are indicated as the labeled colors. (FIG. 12B). Violin plot of SYCP2 expression in PAM50 subtypes of breast cancer. (LumA n=618, LumB n=156, TNBC n=62, Normal n=113. (FIG. 12C) The analysis of Gene copy number variants, DNA methylation levels and somatic mutations with corresponding SYCP2 express levels in different cancer types using the TCGA database. (FIG. 12D) The DNA methylation levels of randomly selected two loci (cg22214414 and cg07347645) at intron 1 of SYCP2 indicated from schematic chart at top were measured. The heatmap showed the correlation between SYCP2 expression from low to high and DNA methylation levels at cg22214414 and cg07347645. The data was collected from TCGA (n=309). (FIG. 12E) The relative DNA methylation levels at two randomly selected loci shown from 6C of breast tumors compared to the adjacent normal breast tissue. The data was collected from TCGA (n=309).

(FIG. 13A). Summarization of subtypes of breast cancer patients in a Sacituzumab Govitecan (IMMU-132) clinical trial group. Patients were divided to high SYCP2 group and low SYCP2 group by IHC of SYCP2. IHC staining of SYCP2 expression in patient tumor tissues from the IMMU-132 clinical trial group. Representative images were shown. Cutoff value is median. Numbers of patients' response as Partial Response (PR) or Stable Disease (SD) in low SYCP2 group and high SYCP2 group in IMMU clinical trial are shown. (FIG. 13B) Kaplan-Meier curves of patients' overall survival and progression free survival in FIG. 13A. (FIG. 13C) Overall survival curves of 1095 patients from TCGA. Cutoff value is median. R value and p value were calculated by COX survival analysis. (FIG. 13D) The scheme of the role of SYCP2 in DDR drug resistance in breast cancer. SYCP2 in drug resistant clones recruited critical HR factors in both canonical HR and TC-HR, which helped cancer cells survived from anti-cancer treatments and further expanded, leading to a bad prognosis.

(FIG. 14A) Survival rate of HR proficient (HR+) HST578 cancer cells with and without siBRCA1 and/or TRDMT1i YW-1842 at indicated dose. The survival rate of these cells was analyzed (n=3, Mean±SD). (FIG. 14B) Survival rate of MBAMD231 (HR+) and HCC1937 (HRD) cells. The survival rate of these cells was analyzed (n=3, Mean±SD). (FIG. 14C) Cell survival rate in different cancer cell lines via colony-forming assay with the treatment of Imatinib at indicated dose (n=3, mean+/−S.D.). Cell lines are listed in order with the expression level from SYCP2high to SYCP2low.

DETAILED DESCRIPTION OF THE INVENTION

Figures 1A, 1B, 1C, 1D:
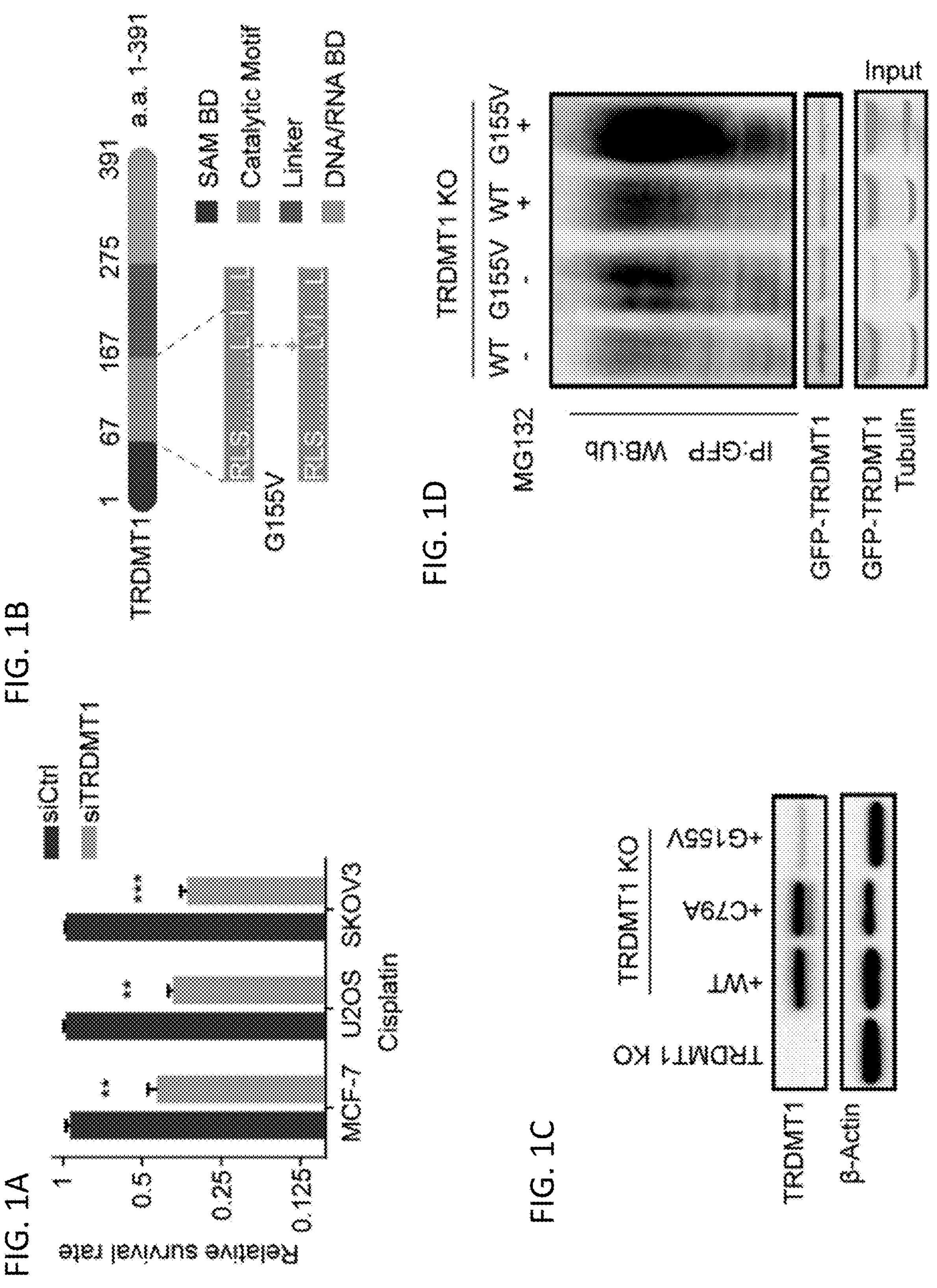
FIGS. 1A-H show that TRDMT1$^{G155V}$ is highly ubiquitinated in cells.

Disclosed herein are compositions and methods to identify and treat patients suffering from cancer that can benefit from cancer drugs that target the DNA damage response (DDR). As demonstrated in the Examples that follow, bioinformatic analysis of gene expression in breast tumors and other cancer cell lines resulted in the identification of a diagnostic panel to enlarge the patient population that can received treatment with DNA damaging agents, such as DNA-damaging drugs or DNA repair inhibitors, or treatment with DNA damaging agents in combination with sensitizers for the DNA damaging agent. Moreover, the Examples also demonstrate that RNA methyltransferase inhibitors can be used alone or in combination with additional therapeutic agents, such as DNA damaging agents, to treat patients suffering from cancer.

The DDR is a collection of mechanisms that allow cells to combat the threats posed by DNA damage and can include mechanisms for the identification, signaling, or repair of DNA damage. A fundamental feature of cancer is genome instability. Most carcinogens operate by generating DNA damage and causing mutations. Moreover, inherited DDR defects commonly predispose to cancer, contribute to a mutator phenotype of many malignancies, and may allow tumor-cell survival and proliferation despite enhanced mutation rates and genome instability.

Other than surgery, the most prevalent cancer treatments are the administration of DNA damaging agents, such as radiotherapy and chemotherapies, that function by generating DNA damage or inhibiting DNA repair. The DNA damaging agents may include poly(ADP-ribose) polymerase (PARP) inhibitors (e.g., olaparib, rucaparib, niraparib, or talazoparib), ATM serine/threonine kinase (ATM) inhibitors, ATR Serine/threonine-protein kinase (ATR) inhibitors, radiotherapy and radiomimetics (e.g., ionizing radiation or bleomycin), monofunctional alkylators (e.g., alkylsulphonates, nitrosourea compounds, or temozolomide), bifunctional alkylators (e.g., nitrogen mustard, Mitomycin C, or Cisplatin), antimedtabolites (e.g., 5-Fluorouracil (5FU), thiopurines, or folate analogs), topoisomerase inhibitors, including topoisomerase I (Topo I) and II (Topo II) inhibitors (e.g., Camptothecins (Topo I), Etoposide (Topo II), anthracyclines, such as Doxorubicin, Epirubicin, or Daunorubicin (Topo II)), replication inhibitors (e.g., Aphidicolin or Hydroxyurea), and the like. Although such therapies generate dose-limiting toxicities in normal tissues, they are often efficacious. In part, this reflects most cancer cells being DDR-impaired and proliferating more rapidly than most normal cells. Nevertheless, DNA repair provides a common mechanism for cancer-therapy or drug resistance. Thus methods to overcome drug resistance or alternatives to the use of DNA damaging agents are needed.

The present technology provides for compositions for use in treatment of cancers, methods for treating patients in need of such treatment, biomarkers for cancer diagnosis, biomarkers predictive of drug response or resistance, and prognostic markers for patient outcome. These and other aspects of the technology will be further described below.

One aspect of the invention provides for a RNA methyl transferase inhibitor. The RNA methyltransferase inhibitor may be used alone or in combination with another therapeutic agent for the treatment of subject in need thereof. In some embodiments, the RNA methyltransferase may sensitize the subject to therapy with the additional therapeutic agent.

The RNA methyltransferase inhibitor may be a compound of Formula I (I)

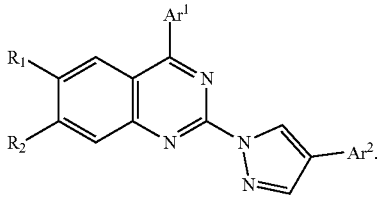

where $R_1$ and $R_2$ may be independently selected from hydrogen; unsubstituted or substituted, unbranched or branched, saturated or unsaturated, acyclic or cyclic $C_1$-$C_6$ alkyl; hydroxide; an unsubstituted or substituted, unbranched or branched, saturated or unsaturated, acyclic or cyclic $C_1$-$C_6$ alkoxy; an unsubstituted or substituted, unbranched or branched, saturated or unsaturated, acyclic or cyclic $C_1$-$C_6$ amino; an unsubstituted or substituted aryl; or an unsubstituted or substituted heteroaryl. $Ar^1$ and $Ar^2$ may be independently selected from an unsubstituted or substituted aryl or an unsubstituted or substituted heteroaryl.

In some embodiments, one or both of $R_1$ and $R_2$ may be the unsubstituted or substituted, unbranched or branched, saturated or unsaturated, acyclic or cyclic $C_1$-$C_6$ alkoxy. In particular embodiments, one or both of $R_1$ and $R_2$ may be methoxy.

In some embodiments, one or both of $R_1$ and $R_2$ may be hydrogen.

In some embodiments, one or both of $R_1$ and $R_2$ may be an unsubstituted or substituted, unbranched or branched, saturated or unsaturated, acyclic or cyclic $C_1$-$C_6$ amino. In a particular embodiment, one or both of $R_1$ and $R_2$ may be a substituted piperazine group.

In some embodiments, one or both of $R_1$ and $R_2$ may an unsubstituted or substituted, unbranched or branched, saturated or unsaturated, acyclic or cyclic $C_1$-$C_6$ alkyl.

In some embodiments, one or both of $R_1$ and $R_2$ may be hydroxide.

In some embodiments, one or both of $R_1$ and $R_2$ may be an unsubstituted or substituted aryl or heteroaryl.

In some embodiments, $Ar^1$ is an unsubstituted aryl or heteroaryl. Suitably, the unsubstituted aryl or heteroaryl may be a thiophene, phenyl, quinolone, pyridine, furan, or the like. In particular embodiment, $Ar^1$ is an unsubstituted thiopehen.

In some embodiments, the $Ar^1$ is a substituted aryl or heteroaryl. Suitably, the unsubstituted aryl or heteroaryl may be a thiophene, phenyl, quinolone, pyridine, furan, or the like. In some embodiments, the substituent may be selected from an alkyl, an alkoxyl, an amino, a sulfonyl, a carbonyl group, and the like.

In some embodiment $Ar^2$ is a substituted aryl or heteroaryl. Suitably, the substituent may be a sulfonyl, including alkylsulfonyls and aminosulfonyls and the like. In particular embodiments, the substituted aryl is a sulfonyl substituted phenyl, including without limitation a methyl sunfonyl substituted phenyl. In particular embodiment, $Ar^2$ is an methylsulfonyl substituted phenyl.

In some embodiments $Ar^2$ is an unsubstituted awl or heteroaryl. In particular embodiments, the unsubstituted heteroaryl is a pyridine.

Exemplary RNA methyltransferase inhibitors include those shown in Table 1.

TABLE 1

Exemplary RNA methyltransferase inhibitors.

| Example | Structure |
| --- | --- |
| 1 | 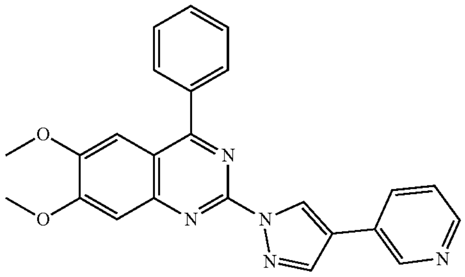 [SMILES: COc1cc2nc(-n3cc(-c4cccnc4)cn3)nc(-c3ccccc3)c2cc1OC] |
| 2 | 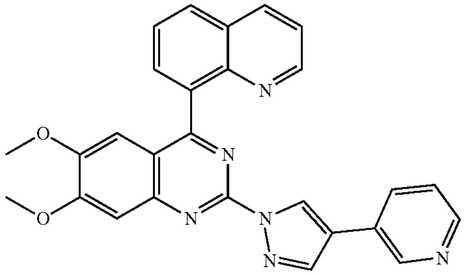 [SMILES: COc1cc2nc(-n3cc(-c4cccnc4)cn3)nc(-c3cccc4cccnc34)c2cc1OC] |
| 3 | 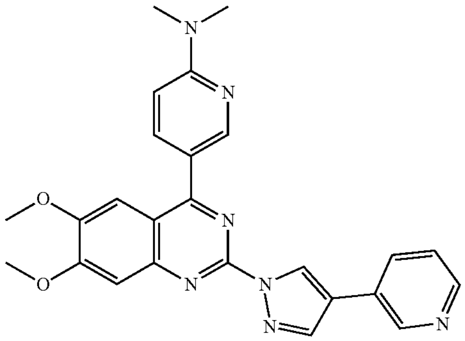 [SMILES: COc1cc2nc(-n3cc(-c4cccnc4)cn3)nc(-c3ccc(N(C)C)nc3)c2cc1OC] |
| 4 | 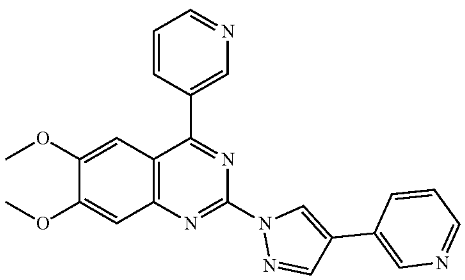 [SMILES: COc1cc2nc(-n3cc(-c4cccnc4)cn3)nc(-c3cccnc3)c2cc1OC] |

TABLE 1-continued
| Exemplary RNA methyltransferase inhibitors. | |
|---|---|
| Example | Structure |
| 5 | 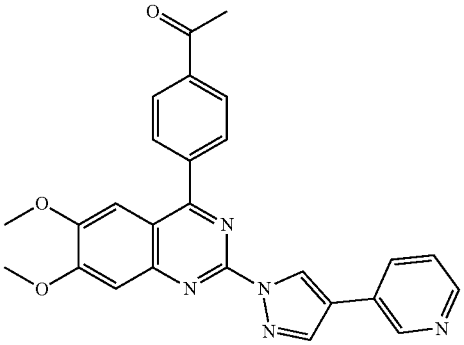 [SMILES: COc1cc2nc(-n3cc(-c4cccnc4)cn3)nc(-c3ccc(C(C)=O)cc3)c2cc1OC] |
| 6 | 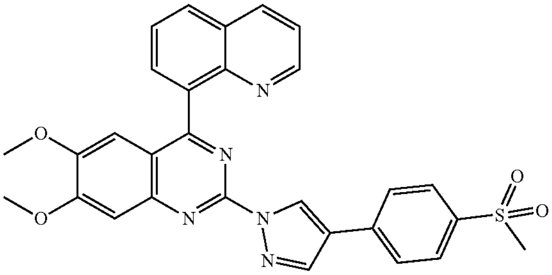 [SMILES: COc1cc2nc(-n3cc(-c4ccc(S(C)(=O)=O)cc4)cn3)nc(-c3cccc4cccnc34)c2cc1OC] |
| 7 | 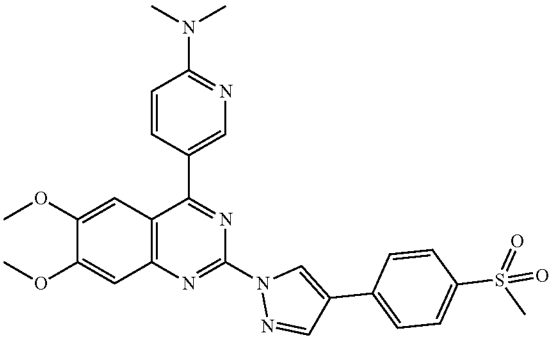 [SMILES: COc1cc2nc(-n3cc(-c4ccc(S(C)(=O)=O)cc4)cn3)nc(-c3ccc(N(C)C)nc3)c2cc1OC] |
| 8 | 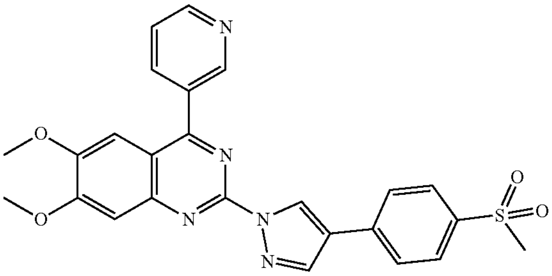 [SMILES: COc1cc2nc(-n3cc(-c4ccc(S(C)(=O)=O)cc4)cn3)nc(-c3cccnc3)c2cc1OC] |
| 9 | 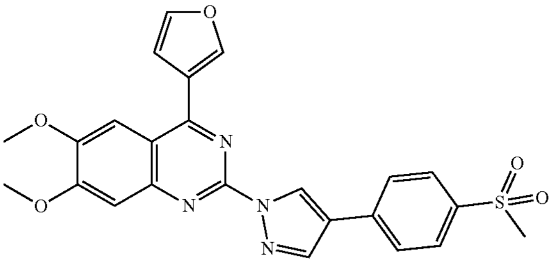 [SMILES: COc1cc2nc(-n3cc(-c4ccc(S(C)(=O)=O)cc4)cn3)nc(-c3ccoc3)c2cc1OC] |

TABLE 1-continued
| Exemplary RNA methyltransferase inhibitors. | |
|---|---|
| Example | Structure |
| 10 (YW-1842) | 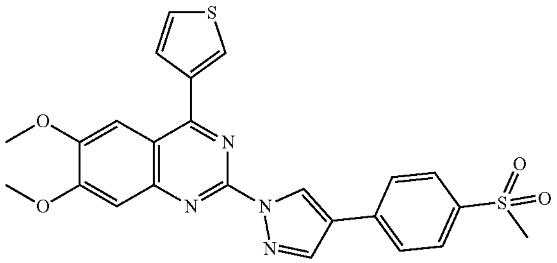 [SMILES: COc1cc2nc(-n3cc(-c4ccc(S(C)(=O)=O)cc4)cn3)nc(-c3ccsc3)c2cc1OC] |
| 11 | 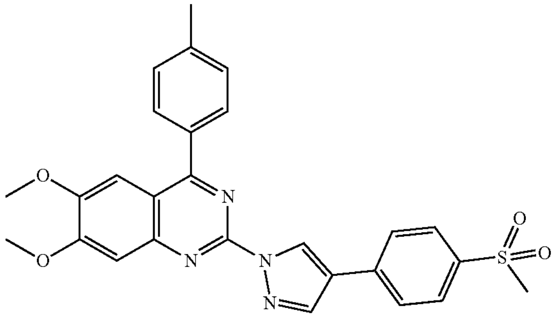 [SMILES: COc1cc2nc(-n3cc(-c4ccc(S(C)(=O)=O)cc4)cn3)nc(-c3ccc(C)cc3)c2cc1OC] |
| 12 | 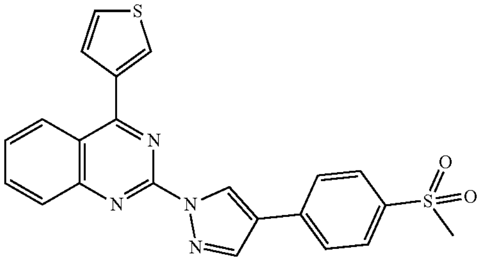 [SMILES: CS(=O)(=O)c1ccc(-c2cnn(-c3nc(-c4ccsc4)c4ccccc4n3)c2)cc1] |
| 13 | 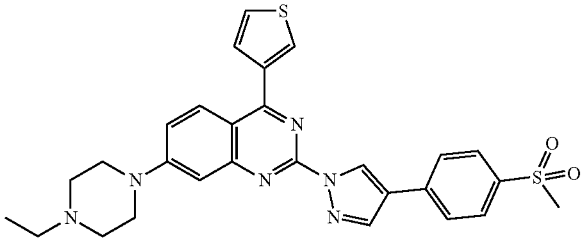 [SMILES: CCN1CCN(c2ccc3c(-c4ccsc4)nc(-n4cc(-c5ccc(S(C)(=O)=O)cc5)cn4)nc3c2)CC1] |
| 14 | 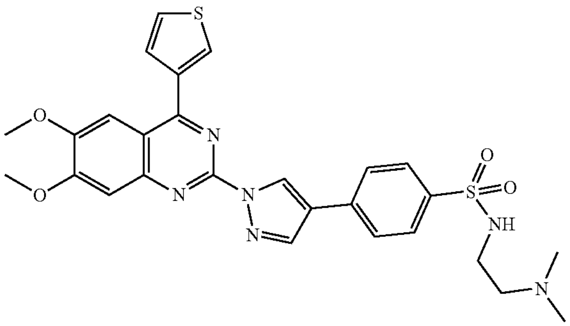 |

TABLE 1-continued

| Exemplary RNA methyltransferase inhibitors. | |
|---|---|
| Example | Structure |
| 15 | 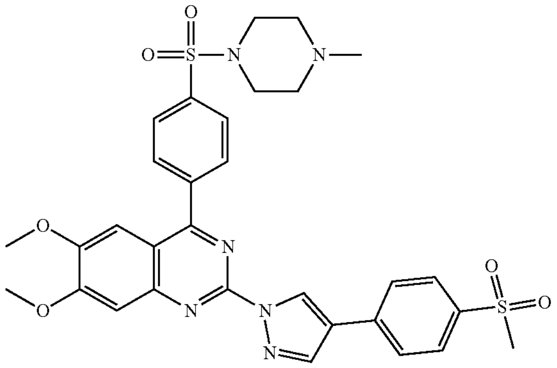 |
| 16 | 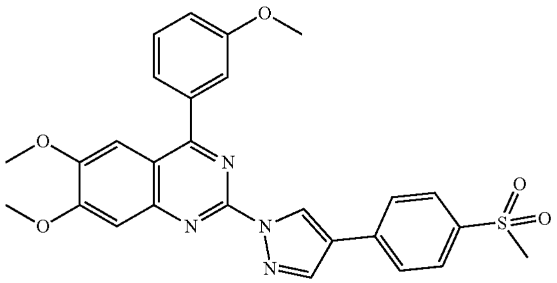 |

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as $C_1$-$C_{12}$ alkyl, $C_1$-$C_{10}$-alkyl, and $C_1$-$C_6$-alkyl, respectively. Representative alkoxyl groups include methyl, ethyl, tert-butyl and the like.

The term "alkylene" refers to a diradical of an alkyl group. An exemplary alkylene group is $—CH_2CH_2—$.

The term "haloalkyl" refers to an alkyl group that is substituted with at least one halogen. For example, $—CH_2F$, $—CHF_2$, $—CF_3$, $—CH_2CF_3$, $—CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxyl" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$-alkenyl, $C_2$-$C_{10}$-alkenyl, and $C_2$-$C_6$-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as $C_2$-$C_{12}$-alkynyl, $C_2$-$C_{10}$-alkynyl, and $C_2$-$C_6$-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a diradical of an cycloalkyl group.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 $C_x$-$C_x$ nomenclature where x is an integer specifying the number of ring atoms. For example, a $C_3$-$C_7$ heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines, wherein substituents may include, for example, alkyl, cycloalkyl, heterocyclyl, alkenyl, and aryl.

The terms "alkoxyl" or "alkoxy" are art-recognized and refer to an alkyl group, as defined above, having an oxygen radical attached thereto. Representative alkoxyl groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

An "epoxide" is a cyclic ether with a three-atom ring typically include two carbon atoms and whose shape approximates an isosceles triangle. Epoxides can be formed by oxidation of a double bound where the carbon atoms of the double bond form an epoxide with an oxygen atom. The term "carbonyl" as used herein refers to the radical —C(O)—.

The term "carboxamido" as used herein refers to the radical —C(O)NRR', where R and R' may be the same or different. R and R' may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereo isomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Compositions comprising substantially purified stereoisomers, epimers, or enantiomers, or analogs or derivatives thereof are contemplated herein (e.g., a composition comprising at least about 90%, 95%, or 99% pure stereoisomer, epimer, or enantiomer.)

Methods of preparing RNA methyltransferase inhibitors are also provided. The compounds may be prepared by (a) providing a quinazoline (int. A) of formula int. A

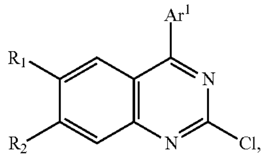

providing an arylpyrozole (int. B) of formula int. B

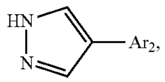

and contacting the quinazoline (int. A) with the arylpyrozole (int. B) under conditions effective in preparing the RNA methyltransferase inhibitor. Suitably, the method may prepare any of the RNA methyltransferases described herein.

Scheme 1 further illustrates the method for preparing the RNA methyltransferases described herein SCHEME 1. Preparation of TRDMT1 inhibitors.

a

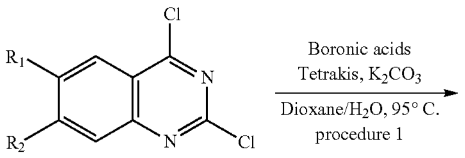

SM

-continued

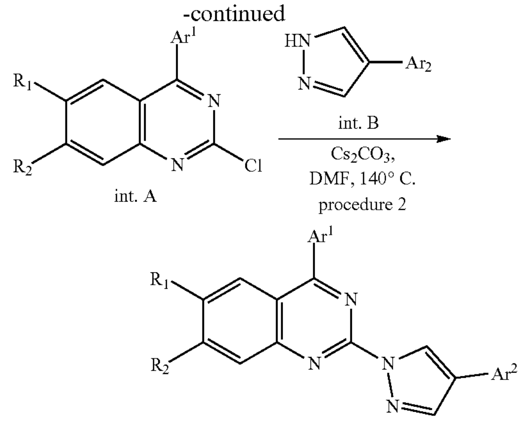

Final compound b

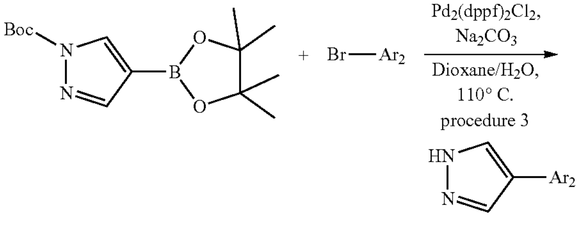

int. B

General procedure step 1 may include the following. A mixture of starting material (SM) (1.0 mmol), boronic acid (1.0 mmol), and $K_2CO_3$ (2.0 mmol) in dioxane (4.0 mL) and water (1.0 mL) were degassed by $N_2$ for 10 min. $Pd(PPh_3)_4$ (0.03 mmol) was added in one portion and the mixture was degassed for another 5 min. The resulted suspension was stirred under $N_2$ atmosphere and the reaction process was monitored by LC-MS. After the consumption of SM was observed, the reaction mixture was allowed to cool to room temperature and separated between ethyl acetate and water. The organic layer was washed with water and brine, dried over sodium sulfate and concentrated to run column (Hexane/ethyl acetate=4/1) to get the desired product.

General procedure step 2 may include the following. A mixture of int. A, int. B (0.2 mmol), and $Cs_2CO_3$ (0.3 mmol) in DMF (1.0 mL) was heated to 140° C. under microwave irradiation for 30 min. After the consumption of int. A was observed, the reaction mixture was concentrated to run column (DCM/MeOH=20/1) to get the desired product.

General procedure step 3 may include the following. A mixture of tert-butyl 4-(4,4,5,5-tetramethyl-1,3,2-dioxaborolan-2-yl)-1H-pyrazole-1-carboxylate (3.4 mmol), bromide (3.3 mmol), and $Na_2CO_3$ (2.0 mmol) in dioxane (20.0 mL) and water (5.0 mL) were degassed by $N_2$ for 10 min. $Pd(dppf)_2Cl_2$ (0.03 mmol) was added in one portion and the mixture was degassed for another 10 min. The resulted suspension was stirred under Na atmosphere and the reaction process was monitored by LCMS. After the consumption of bromide was observed, the reaction mixture was allowed to cool to room temperature and separated between ethyl acetate and water. The organic layer was washed with water and brine, dried over sodium sulfate and concentrated to run column (DCM/MeOH=20/1) to get the desired product.

Exemplary methods for preparing compounds are further provided in the Examples.

The compounds disclosed and utilized in the methods disclosed herein may be formulated as pharmaceutical compositions that include an effective amount of one or more RNA methyltransferases as disclosed herein and one or more pharmaceutically acceptable carriers, excipients, or diluents.

The compounds for use according to the methods disclosed herein may be administered as a single compound or a combination of compounds. For example, an RNA methyltransferase inhibitor may be administered as a single compound or in combination with another compound that treats cancer or that has a different pharmacological activity. In some embodiments, the pharmaceutical composition may further include an effective amount of a DNA damaging agent. In other embodiments, the pharmaceutical composition comprising the effective amount of RNA methyltransferase inhibitor may be intended for co-administration with a second pharmaceutical composition comprising the effective amount of DNA damaging agent.

The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 μM.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Pharmaceutical compositions comprising the compounds may be adapted for administration by any appropriate route, for example by the oral (including buccal or sublingual), rectal, nasal, topical (including buccal, sublingual or transdermal), vaginal, parenteral (including subcutaneous, intramuscular, intravenous or intradermal), or pulmonary route. Such formulations may be prepared by any method known in the art of pharmacy, for example by bringing into association the active ingredient with the carrier(s) or excipient (s). Examples of pharmaceutical compositions for oral administration include capsules, syrups, concentrates, powders and granules.

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases. The particular counter-ion forming a part of any salt of a compound disclosed herein may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The compounds described herein may be used for methods of treatment. In particular, the compounds may be used for methods of treatment of a cancer. In some embodiments, the methods of treatment may include the administration of a sensitizing agent, such as an RNA methyltransferase inhibitor, in combination with the administration of a DNA damaging agent. Use of the sensitizing agent may overcome resistance to treatment with the DNA damaging agent alone. In other embodiments, the methods of treatment may include administration of an RNA methyltransferase inhibitor alone.

As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein, a "subject" may be interchangeable with "patient" or "individual" and means an animal, which may be a human or non-human animal, in need of treatment. A "subject in need of treatment" may include a subject having a disease, disorder, or condition that is responsive to therapy with a sensitizing agent in combination with a DNA damaging agent. In some embodiments, the patent may be have a disease, disorder, or condition that is responsive to therapy with the RNA methyltransferase inhibitor alone or in combination with a DNA damaging agent. For example, a "subject in need of treatment" may include a subject having a cell proliferative disease, disorder, or condition such as cancer. In some embodiments, the cancer may be a breast cancer, an ovarian cancer, an esophageal cancer, a stomach cancer, a colon cancer, a lung cancer, a skin cancer, a prostate cancer, a head and neck cancer, a bone cancer, a kidney cancer, a urinary tract cancer, a bladder cancer, a pancreatic cancer, a pediatric cancer, or a blood cancer.

As used herein the term "effective amount" refers to the amount or dose of the compound that provides the desired effect. An effective amount may be provided as a single or multiple doses to the subject. The disclosed methods may include administering an effective amount of the disclosed compounds (e.g., as present in a pharmaceutical composition) for treating a cell proliferative disease or disorder, such as a cancer.

In some embodiments, the effective amount of the one or more therapeutic agents is effective in decreasing tumor volume. In some embodiments, tumor volume may decrease by 5%, 10%, 20%, 30%, 40%, 50%, 60%, 70%, 80%, 90% or more.

In some embodiments, the effective amount of the one or more therapeutic agents is effective in killing cancerous cells. In some embodiments, 5%, 10%, 20%, 30%, 40%, 50%, 60%, 70%, 80%, 90% or more or cancerous cells may be killed.

In some embodiments, the effective amount of the one or more therapeutic agents is effective in inhibiting the growth or proliferation cancerous cells. In some embodiments, growth or proliferation of cancerous cells are inhibited by %, 10%, 20%, 30%, 40%, 50%, 60%, 70%, 80%, 90% or more when compared to an untreated control.

In some embodiments, the effective amount of the one or more therapeutic agents is effective in increasing the rate of survival or prolonging survival of subjects administered the one or more therapeutic agents in comparison to comparable subjects that are not administered the one or more therapeutic agents. In some embodiments, the rate of survival may increase by 5%, 10%, 20%, 30%, 40%, 50%, 60%, 70%, 80%, 90% or more. In some embodiments, the survival may be prolonged by 5%, 10%, 20%, 30%, 40%, 50%, 60%, 70%, 80%, 90% or more.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

One aspect of the technology includes sensitizers to DNA damaging agents that can target the DDR to overcome cancer-therapy or improve therapeutic outcomes. In some embodiments, the subject in need of a treatment may include a subject having a disease, disorder, or condition associated with the overexpressed TRDMT1 protein or that is in need of disruption or inhibition of TRDMT1. In some embodiments, the subject in need of treatment has a cancer associated with upregulated TRDMT1 expression or TRDMT1 activity. A cancer associated with upregulated TRDMT1 expression or TRDMT1 activity is a cancer or sample thereof that exhibits statistically elevated levels of TRDMT1 expression or TRDMT1 activity when compared to cancerous or non cancerous samples that exhibit normal or near normal levels. In some embodiments, the cancer may be a cancer associated with upregulated TRDMT1 expression or upregulated TRDMT1 activity. Exemplary cancers that may have upregulated TRDMT1 expression or upregulated TRDMT1 activity include breast cancer, ovarian cancer, esophageal cancer, stomach cancer, and colon cancer.

The RNA methyltransferase inhibitors disclosed herein are effective in inhibiting the activity of an RNA methyltransferase such as TRMDT1. This allows for the sensitization of subjects or cells to DNA damaging agents. As a result, the RNA methyltransferase inhibitors are effective for use in methods for the treatment of cancer, inhibiting the growth or proliferation of cells, or for the killing of cells when combined with a DNA damaging agent.

The RNA methyltransferase inhibitors disclosed herein may be utilized for killing or inhibiting the growth or proliferation of a cell by contacting any of the RNA methyltransferase inhibitors as described herein with the cell and further contacting the cell with a DNA damaging agent. Suitably, the methods are effective in killing or inhibiting the growth or proliferation of a variety of cancer cells, including, without limitation, breast cancer, ovarian cancer, esophageal cancer, stomach cancer, colon cancer, or the like.

In some embodiments, the cell is a cell having upregulated TRDMT1 expression or upregulated TRDMT1 activity. Suitably, the method may comprise inhibiting the activity of TRDMT1. This may be accomplished by contacting the cell with an effective amount of any of the RNA methyltransferase inhibitors described herein.

As used herein, a sensitizer or sensitizing agent is any compound or composition that improves or increases the activity, decreases resistance to, or improves a therapeutic outcome of another compound or composition when used in combination with the sensitizer.

Although the molecular mechanisms of how TRDMT1 is regulated at sites of damage and contributes to drug response in cancer was not known, the RNA methyltransferase TRDMT1 catalyzes 5-methylcytosine ($m^5C$) on nascent RNA and contributes to transcription coupled homologous recombination (HR). As demonstrated in the Examples that follow, the TRDMT1 G155V mutation leads to an enhanced response to DNA damaging platinum treatment. The TRDMT1 G155V mutation leads to TRDMT1 degradation via hyper poly-ubiquitination. Moreover E3 ligase, TRIM28, triggers the poly-ubiquitination of TRDMT1 after damage. TRIM28 responds to DNA damage at the transcribed region as well as TRDMT1 and targets Lysine 251 (K251) of TRDMT1, which is adjacent to Glycine 155 in three-dimensional structure for poly-ubiquitination. The depletion of TRIM28 and abrogation of K251 or G155 of TRDMT1 sensitize cells to a variety set of DNA damage agents. $TRDMT1^{G155V}$ also leads to decreased mRNA $m^5C$ formation and impaired HR, which subsequently contributes to increased sensitivity to Cisplatin in vitro and in vivo. Low TRDMT1 expression sensitizes cells to Cisplatin, meanwhile, a subset of tumors exhibit upregulated TRDMT1. Importantly, high TRDMT1 expression is correlated with Cisplatin/Platinum-resistance in ovarian cancer tissues. Methyltransferase inhibitors may functionally suppresses mRNA $m^5C$ formation and effectively enhances the sensitivity of $TRDMT1^{high}$ tumor cells to DNA damage in a TRDMT1-dependent manner. Thus, the amount of TRDMT1 at sites of DNA damage is tightly regulated in cells for efficient repair and cell survival. The findings demonstrated in the Examples reveal a novel function for TRDMT1 promoted $m^5C$ RNA methylation in regulating therapeutic resistance, and demonstrate the unique potential of TRDMT1 inhibitors in clinical therapies.

RNA methyltransferases postranscriptionally modify their RNA substrate by adding a methyl group onto the substrate. RNA methyltransferases may methylate the N6 and N1 positions in adenine, pseudouridylation, and methylate carbon 5 in cytosine ($m^5C$). However, knowledge about RNA:$m^5C$ methyltransferases (RCMTs) and the consequences of RNA $m^5C$ modification were still extremely limited.

tRNA-aspartic acid methyltransferase 1(TRDMT1) was identified as a highly conserved cytosine-C5 methyltransferase that introduced the C38 methylation of tRNA-Asp in many species. TRDMT1 was verified to contribute to mRNAs methylation. TRDMT1 is essential in oxidative stress and heat shock induced tRNA cleavage, and is involved in resistance to 5-AZA by directly binding hnRNPK. Using KillerRed (KR), which releases 02 in a light-inducible manner to cause single-strand breaks and double-strand breaks (DSBs) at specific sites in the genome and locally activates DNA repair pathways, the Examples demonstrate that DNA damage-induced and TRDMT1 mediated-mRNA $m^5C$ is required for the efficient repair of DSBs by promoting transcription coupled homologous recombination (TC-HR). These findings indicate an important role of TRDMT1 in cell survival after damage.

How TRDMT1 is regulated in cells after damage is not understood. Cytosine analogs azacytidine and decitabine have been developed as DNA methyltransferases (DNMTs) inhibitors for epigenetic cancer therapy, but their use was limited owing to poor bioavailability and toxicities. Although all of the human RNMTs are members of the S-Adenosylmethionine (AdoMet or SAM)-dependent methyltransferase superfamily, as are the protein lysine/arginine methyltransferases (PKMTs/PRMTs) and DNMTs, for which potent and selective inhibitors have been approved; however, to date, there are no known inhibitors of RNA methyltransferases (RNMTs) beyond the reaction product S-Adenosylhomocysteine (AdoHcy, or SAH) and the universal nucleoside analog sinefungin.

The relevance of TRDMT1 expression, suppression, and its mutation in the treatment response of cancer is described herein. Somatic mutation of the TRDMT1 G155V reveals the molecular mechanisms of how TRDMT1 regulation and TRDMT1 mediated HR contribute to drug resistance in ovarian cancer. With the mass spectrometry analysis, there is evidence that the TRDMT1 G155V mutant is highly polyubiquitinated via the E3 ligase TRIM28, also named KAP-1. Lysine 251 (K251) of TRDMT1, which is adjacent to Glycine 155 in the three-dimensional protein structure, is targeted for polyubiquitination. The depletion of TRIM28 and abrogation of K251 or G155 of TRDMT1 sensitize cells to a variety set of DNA damage agents. Together, due to excessive TRDMT1 degradation in TRDMT1 G155V mutated cells, TRDMT1 loss of function leads to inefficient repair and contributes to increased sensitivity of cancer cells. Given the role of TDRMT1 in DNA damage repair, a potent inhibitor for the RNA methyltransferase allows for new methods for treating cells with agents that damage DNA.

One aspect of the technology includes the use of RNA methyltransferase inhibitors overcome cancer-therapy resistance or improve therapeutic outcomes. As demonstrated in the Examples, the RNA methyltransferases inhibitors described herein are effective in killing cells that have upregulated SYCP2 expression or upregulated SYCP2 activity. In some embodiments, the subject in need of a treatment may include a subject having a disease, disorder, or condition associated with the overexpressed SYCP2 proteins or that is in need of disruption or inhibition of SYCP2. In some embodiments, the subject in need of treatment has a cancer associated with upregulated SYCP2 expression or SYCP2 activity. A cancer associated with upregulated SYCP2 expression or SYCP2 activity is a cancer or sample thereof that exhibits statistically elevated levels of SYCP2 expression or SYCP2 activity when compared to cancerous or non-cancerous samples that exhibit normal or near normal levels. In some embodiments, the cancer may be a cancer associated with upregulated SYCP2 expression or upregulated SYCP2 activity. Exemplary cancers that may have upregulated SYCP2 expression or upregulated SYCP2 activity include breast cancer, ovarian cancer, esophageal cancer, stomach cancer, colon cancer, lung cancer, skin cancer, prostate cancer, head and neck cancer, bone cancer, kidney cancer, urinary tract cancer, bladder cancer, and pancreatic cancer.

The RNA methyl transferases disclosed herein may be utilized for killing or inhibiting the growth or proliferation of a cell by contacting any of the RNA methyltransferase inhibitors as described herein with the cell. Suitably, the methods are effective in killing or inhibiting the growth or proliferation of a variety of cancer cells, including, without limitation, breast cancer, ovarian cancer, esophageal cancer, stomach cancer, colon cancer, lung cancer, skin cancer, prostate cancer, head and neck cancer, bone cancer, kidney cancer, urinary tract cancer, bladder cancer, pancreatic cancer, and the like.

As described in the Examples, upregulated SYCP2 expression or activity can be associated with DNA damaging agent resistance. As demonstrated in the Examples that follow, Synaptonemal Complex Protein 2 (SYCP2), a component of the meiotic synaptonemal complex, is ectopically expressed in breast cancer and other cancers and associates with broad resistance to DDR-targeted drugs. Surprisingly, however, the RNA methyltransferase inhibitors described herein are effective in killing cancer cells that are resistant to DDR-targeted drugs, such as PARPi. SYCP2 overexpression correlates with poor prognosis in breast cancer patients and with decreased survival in a clinical trial of antibody-conjugated topoisomerase I inhibitor. SYCP2 overexpression is sufficient to enhance homologous recombination (HR) and confer drug resistance. Mechanistically, SYCP2 promotes RAD51 localization to DNA breaks by interacting with RAD51 through a BRC-like domain. SYCP2 promotes HR independently of BRCA1 and, as a result, SYCP2 is a BRCA-independent determinant of DNA damage sensitivity. Thus, SYCP2, which enhances HR, is a biomarker for breast cancer diagnosis, a predictor of drug response, a prognostic marker for patient outcome, and a target in breast cancer therapy.

As further demonstrated below, upregulated expression of SYCP2 is a marker for diagnosis and prognostication. SYCP2 is associated with resistance to a panel of DNA damaging agents. The expression levels of SYCP2 in cancer cells strongly correlated with the resistance to DNA damaging agents, such as PARP inhibitors. The levels of SYCP2-based diagnostic panel correlate with resistance to DDR-targeted drugs. SYCP2-based diagnostic panel is a biomarker for poor prognosis and drug resistance in cancer patients. Cancer patients and cells with upregulation of SYCP2-based diagnostic panel show enhanced HR and resistance to DNA damaging agents, such as PARPi and other DNA damaging agent independently of BRCA1.

As demonstrated in the Examples, the RNA methyltransferases inhibitors described herein are effective in killing cells that are HR deficient. A HR proficient cancer is a cancer or sample thereof that exhibits normal or near normal levels of homologous recombination DNA repair activity. In other embodiments, the subject has a cancer that is HR deficient. A HR deficient cancer is a cancer or sample thereof that exhibits statistically decreased levels of HR DNA repair activity when compared to HR proficient cancers. In some embodiments, the cancer may be a HR deficient cancer. Exemplary cancers that may be HR deficient include breast cancer, ovarian cancer, prostate cancer, pancreatic cancer, colon cancer, lung cancer, pediatric cancer, and blood cancer.

The RNA methyl transferases disclosed herein may be utilized for killing or inhibiting the growth or proliferation of a cell by contacting any of the RNA methyltransferase inhibitors as described herein with the cell. Suitably, the methods are effective in killing or inhibiting the growth or proliferation of a variety of cancer cells, including, without limitation, breast cancer, ovarian cancer, prostate cancer, pancreatic cancer, colon cancer, lung cancer, pediatric cancer, blood cancer, and the like.

Another aspect of the invention includes methods of diagnosing cancer or predicting drug response or patient outcomes. This allows for the identification of subjects eligible for treatment with the methods described herein. As used herein, a "subject eligible for treatment" is a subject that would be expected to benefit from treatment with a method disclosed herein because they exhibit one or more indicia that allow for prediction of a positive drug response or patient outcome. In contrast, a subject not eligible for treatment is a subject that would not be expected to benefit from treatment with a method disclosed herein because they exhibit one or more indicia that allow for prediction of a negative or neutral drug response or patient outcome. In some embodiments, a negative or neutral drug response or patent outcome would be resistance or likelihood of induced resistance to a proposed therapy.

Methods for diagnosing or predicting drug response or patient outcomes may comprise obtaining a sample from a subject. The sample may be any suitable biological sample for making the desired determination. Samples include without limitation cellular, tissue, biopsy, or fluid samples that may be obtained from a subject by methods known in the art. In some embodiments, the desired determination is the level of expression or activity of a protein, such as TRDMT1 or SYCP2 in a sample. In other embodiments, the proficiency for HR may be determined. The level of expression or activity of a protein or proficiency may be suitably determined by methods described herein or others known in the art.

In some embodiments, it will be determined that the expression or activity of TRDMT1 or SYCP2 is upregulated. As used herein, upregulated means that amount of the TRDMT1 or SYCP2 expressed or is activity is elevated in a cell, tissue, or tumor in a statistically significant amount and downregulated means that the TRDMT1 or SYCP2 expressed or is activity is lower in a cell, tissue, or tumor in a statistically significant amount. In some embodiments, the statistically significant difference is determined between different cell, tissue, or tumor types or is determined between healthy or diseased cells or tissues, such as between healthy tissue and a tumor. The term "ectopic expression" or "ectopically expressed" may indicate that the marker is up- or downregulated as well depending on context.

In some embodiments, determination of SYCP2 expression or activity, TRDMT1 expression or activity, or HR proficiency may be used either on its own or in in any combination to guide treatment with an RNA methyl transferase, a DNA damaging agent, or a combination thereof or to select patients that may be treated with an RNA methyl transferase and/or a DNA damaging agent.

If the levels of expression or activity of a protein are upregulated, suggesting that the subject will be resistant to treatment with a DNA damaging agent or prognosis will be poor, treatment may be augmented with a sensitizing agent. Suitably, the sensitizing agent may be a RNA methyltransferase inhibitor but other compounds may also be used to improve or increase activity, decrease resistance to, or improve a therapeutic outcome when the DNA damaging agent is administered to the patent.

For some subjects, the level of expression or activity of SYCP2 may be upregulated. Because SYCP2 expression is associated with resistance to DDR-targeted drugs, alternative approaches for treating subjects are suggested. In some embodiments, determination of upregulated expression or activity of SYCP2 may be used to determine eligibility for or whether to administer a SYCP2 effective therapy. A SYCP2 effective therapy is a therapy that alleviate symptoms, eliminate the causation of resultant symptoms either on a temporary or permanent basis, and/or to prevent or slow the appearance or to reverse the progression or severity of resultant symptoms of the named disease or disorder associated with upregulated expression or activity of SYCP2. The SYCP2 effective therapy may lower expression or inhibit activity of SYCP2. In some embodiments, the SYCP2 effective therapy is the administration of any of the RNA methyltransferase inhibitors described herein alone or in combination with one or more additional therapeutic agents, including DNA damaging agents.

For some subjects, the level of expression or activity of TRDMT1 may upregulated. Because TRDMT1 expression is associated with resistance to DDR-targeted drugs, alternative approaches for treating subjects may be suggested. In some embodiments, determination of upregulated expression or activity of TRDMT1 may be used to determine eligibility for or whether to administer a TRDMT1 effective therapy. A TRDMT1 effective therapy is a therapy that alleviate symptoms, eliminate the causation of resultant symptoms either on a temporary or permanent basis, and/or to prevent or slow the appearance or to reverse the progression or severity of resultant symptoms of the named disease or disorder associated with upregulated expression or activity of TRDMT1. The TRDMT1 effective therapy may lower expression or inhibit activity of TRDMT1. In some embodiments, the TRDMT1 effective therapy is the administration of any of the RNA methyltransferase inhibitors described herein alone or in combination with one or more additional therapeutic agents, including DNA damaging agents.

For some subjects, the subject may have a HR deficient cancer. In some embodiments, determination HR proficiency may be used to determine eligibility for whether to administer a HR effective therapy. A HR effective therapy is a therapy that alleviate symptoms, eliminate the causation of resultant symptoms either on a temporary or permanent basis, and/or to prevent or slow the appearance or to reverse the progression or severity of resultant symptoms of the named disease or disorder is associated with HR deficiency. In some embodiments, the HR effective therapy is the administration of any of the RNA methyltransferase inhibitors described herein alone or in combination with one or more additional therapeutic agents, including DNA damaging agents.

Thus, diagnostic panel used to determine of expression or activity of SYCP2, TRDMT1, or HR proficiency may enlarge the subset of cancer patients, including those with or without HR deficiency and/or BRCA mutations, eligible for treatment with DNA damaging agents. This may allow for the administration of DNA damaging agents on their own or in combination with sensitizing agents, such as any of the RNA methyltransferase inhibitors described herein. Moreover, the methods and diagnostic panels may also be used to discriminate patients with possible resistance to such DNA damaging agents so that alternative therapies may be used. The alternative therapy may include administration of RNA methyltransferase inhibitors on their own.

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Example 1: 6,7-dimethoxy-4-phenyl-2-(4-(pyridin-3-yl)-1H-pyrazol-1-yl)quinazoline

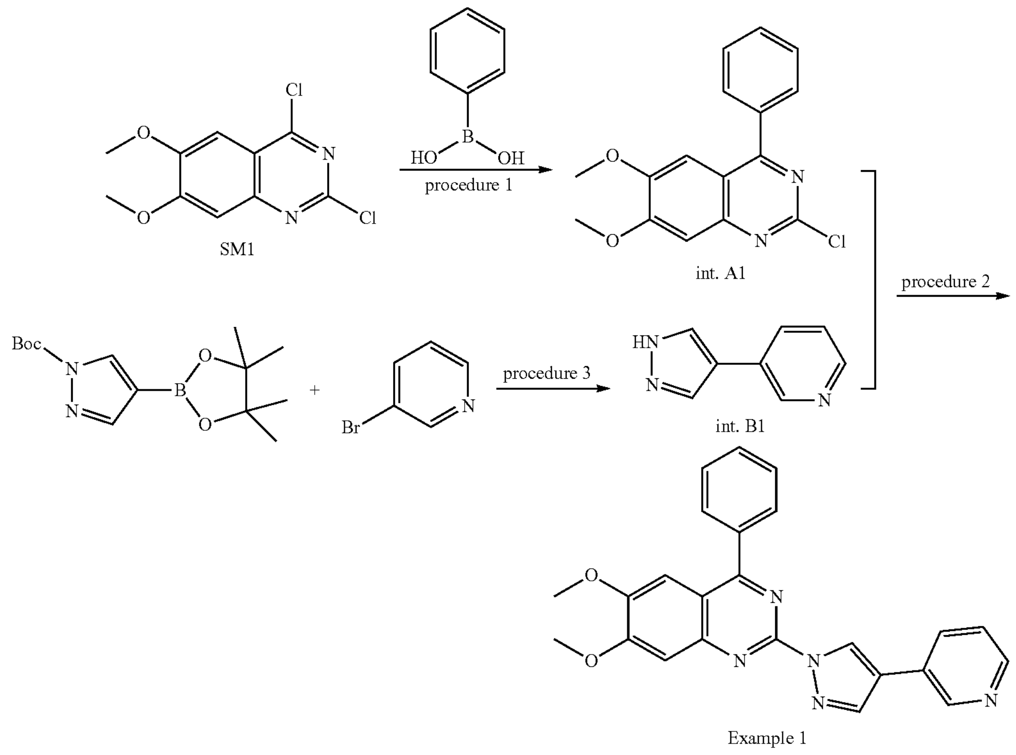

Int. A1 was prepared from 2,4-dichloro-6,7-dimethoxyquinazoline (SM1) and phenylboronic acid following general procedure 1, beige solid (yield 60%). $^1H$ NMR (400 MHz, $CDCl_3$) δ 7.75-7.70 (m, 2H), 7.55-7.49 (m, 3H), 7.27 (s, 1H), 7.26 (s, 1H), 4.01 (s, 3H), 3.85 (s, 3H).

Int. B1 was prepared from tert-butyl 4-(4,4,5,5-tetramethyl-1,3,2-dioxaborolan-2-yl)-1H-pyrazole-1-carboxylate and 3-bromopyridine following general procedure 3, beige solid (yield 58%). $^1H$ NMR (400 MHz, DMSO-$d_6$) δ 13.08 (s, 1H), 8.87 (s, 1H), 8.38 (d, J=4.4 Hz, 1H), 8.32 (s, 1H), 8.02 (s, 1H), 7.98 (dt, J=7.9, 1.6 Hz, 1H), 7.36 (dd, J=7.9, 4.8 Hz, 1H).

Example 1 was prepared from int. A1 and int. B1 following general procedure 2, yellow solid (yield 40%). $^1H$ NMR (400 MHz, $CDCl_3$+10% $CD_3OD$) δ 9.02 (d, J=0.9 Hz, 1H), 8.79-8.77 (m, 1H), 8.39 (dd, J=4.8, 1.5 Hz, 1H), 8.11 (t, J=0.9 Hz, 1H), 7.90-7.86 (m, 1H), 7.81-7.77 (m, 2H), 7.58-7.53 (m, 3H), 7.47 (s, 1H), 7.31 (dd, J=7.9, 4.9 Hz, 1H), 7.28 (s, 1H), 7.26 (s, 1H), 4.03 (s, 3H), 3.84 (s, 3H).

Example 2: 6,7-dimethoxy-2-(4-(pyridin-3-yl)-1H-pyrazol-1-yl)-4-(quinolin-8-yl)quinazoline

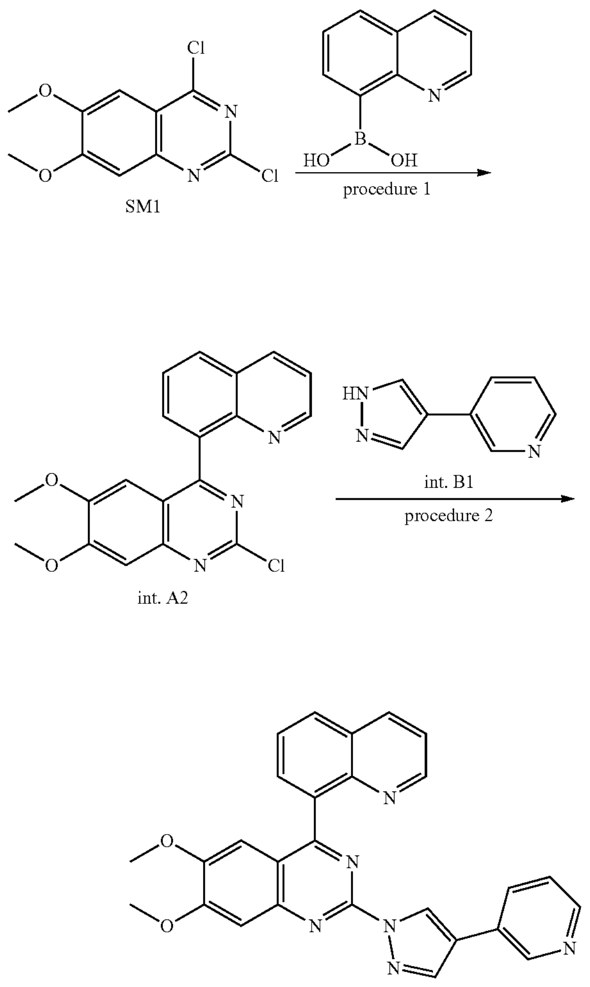

SM1 int. A2

Example 2

Int. A2 was prepared from 2,4-dichloro-6,7-dimethoxyquinazoline (SM1) and quinolin-8-ylboronic acid following general procedure 1, beige solid (yield 61%). $^1$H NMR (400 MHz, $CDCl_3$) δ 8.81 (dd, J=4.2, 1.8 Hz, 1H), 8.28 (dd, J=8.3, 1.8 Hz, 1H), 8.04 (dd, J=8.2, 1.4 Hz, 1H), 7.90 (dd, J=7.1, 1.4 Hz, 1H), 7.74 (dd, J=8.1, 7.2 Hz, 1H), 7.46 (dd, J=8.3, 4.2 Hz, 1H), 7.26 (s, 1H), 6.62 (s, 1H), 4.06 (s, 3H), 3.57 (s, 3H).

Example 2 was prepared from int. A2 and int. B1 following general procedure 2, yellow solid (yield 45%). $^1$H NMR (400 MHz, $CDCl_3$) δ 9.03 (s, 1H), 8.86 (d, J=1.8 Hz, 1H), 8.81 (dd, J=4.1, 1.7 Hz, 1H), 8.47 (dd, J=4.7, 1.3 Hz, 1H), 8.29 (dd, J=8.3, 1.7 Hz, 1H), 8.14 (s, 1H), 8.06 (dd, J=8.2, 1.2 Hz, 1H), 7.95 (dd, J=7.1, 1.3 Hz, 1H), 7.88-7.83 (m, 1H), 7.79-7.73 (m, 1H), 7.55 (s, 1H), 7.46 (dd, J=8.3, 4.2 Hz, 1H), 7.28 (dd, J=7.9, 4.8 Hz, 1H), 6.63 (s, 1H), 4.07 (s, 3H), 3.56 (s, 3H).

Example 3: 5-(6,7-dimethoxy-2-(4-(pyridin-3-yl)-1H-pyrazol-1-yl)quinazolin-4-yl)-N,N-dimethylpyridin-2-amine

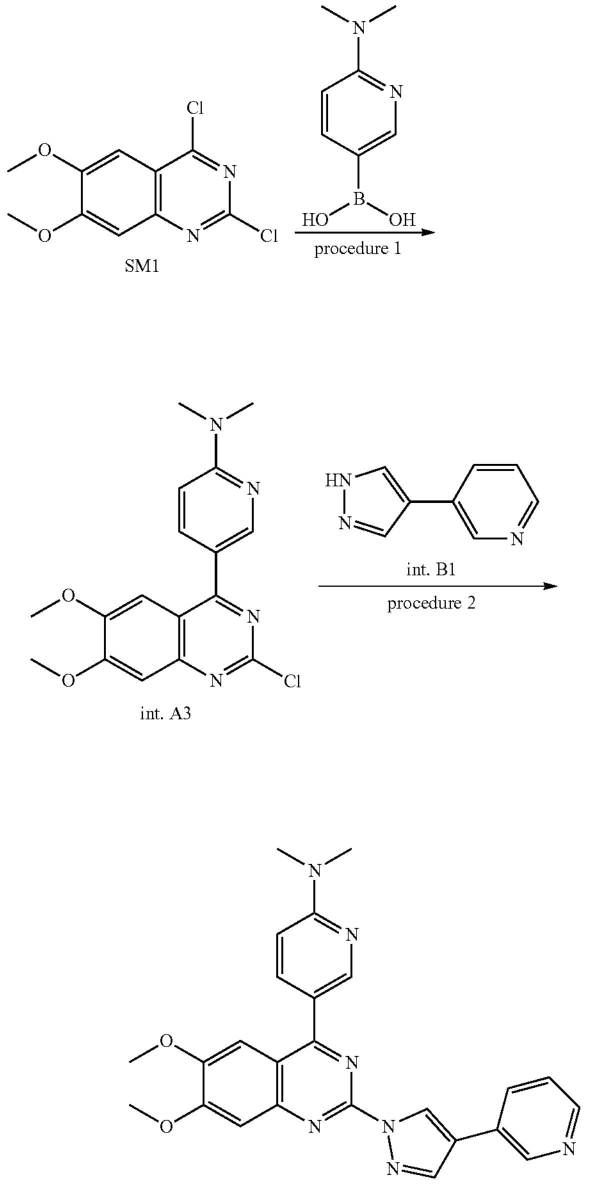

SM1 int. A3

Example 3

Int. A3 was prepared from 2,4-dichloro-6,7-dimethoxyquinazoline (SM1) and (6-(dimethylamino)pyridin-3-yl)boronic acid following general procedure 1, beige solid (yield 63%). $^1$H NMR (400 MHz, $CDCl_3$) δ 7.74 (d, J=8.7 Hz, 2H), 7.46 (s, 1H), 7.23 (s, 1H), 6.80 (d, J=8.7 Hz, 2H), 4.02 (s, 3H), 3.91 (s, 3H), 3.05 (s, 6H).

Example 3 was prepared from int. A3 and int. B1 following general procedure 2, yellow solid (yield 40%). $^1$H NMR (400 MHz, $CDCl_3$) δ 9.05 (s, 1H), 8.90 (s, 1H), 8.76 (s, 1H), 8.51 (d, J=4.4 Hz, 1H), 8.15 (s, 1H), 8.09 (d, J=8.6 Hz, 1H), 7.90 (d, J=7.7 Hz, 1H), 7.53 (s, 1H), 7.45 (s, 1H), 7.33 (dd, J=7.5, 4.9 Hz, 1H), 6.72 (d, J=8.8 Hz, 1H), 4.06 (s, 3H), 3.97 (s, 4H), 3.23 (s, 6H).

Example 4: 6,7-dimethoxy-4-(pyridin-3-yl)-2-(4-(pyridin-3-yl)-1H-pyrazol-1-yl)quinazoline

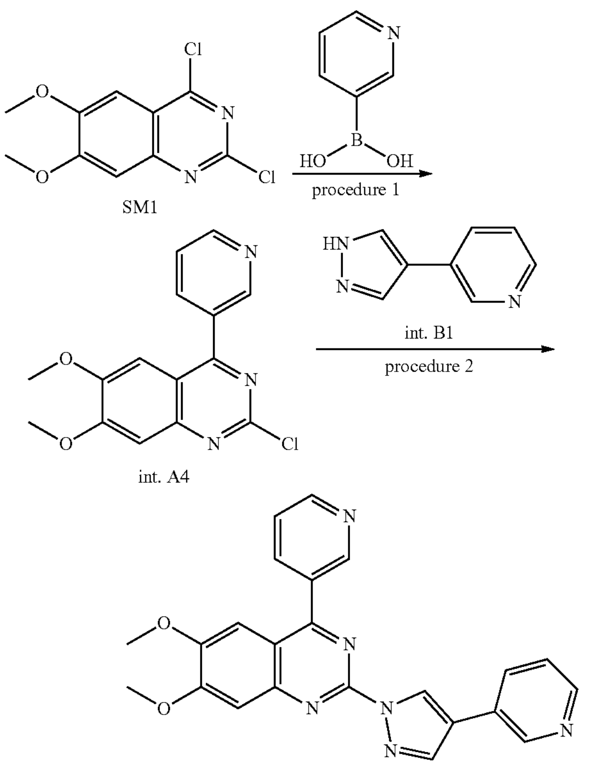

Example 4

Int. A3 was prepared from 2,4-dichloro-6,7-dimethoxy-quinazoline (SM1) and pyridin-3-ylboronic acid following general procedure 1, beige solid (yield 65%). $^1$H NMR (400 MHz, $CDCl_3$) δ 8.82 (d, J=4.8 Hz, 1H), 8.17 (d, J=6.7 Hz, 1H), 7.80 (s, 1H), 7.60-7.54 (m, 1H), 7.51 (s, 1H), 7.23 (s, 1H), 4.06 (s, 3H), 3.91 (s, 3H).

Example 4 was prepared from int. A4 and int. B1 following general procedure 2, yellow solid (yield 44%). $^1$H NMR (400 MHz, $CDCl_3$+10% $CD_3OD$) δ 9.01 (s, 2H), 8.80 (s, 1H), 8.76 (d, J=5.0 Hz, 1H), 8.41 (d, J=4.8 Hz, 1H), 8.21 (d, J=7.8 Hz, 1H), 8.13 (s, 1H), 7.91 (d, J=8.0 Hz, 1H), 7.58 (dd, J=7.6, 5.2 Hz, 1H), 7.50 (s, 1H), 7.34 (dd, J=7.8, 5.1 Hz, 1H), 7.18 (s, 1H), 4.05 (s, 3H), 3.88 (s, 3H).

Example 5: 1-(4-(6,7-dimethoxy-2-(4-(pyridin-3-yl)-1H-pyrazol-1-yl)quinazolin-4-yl)phenyl)ethanone

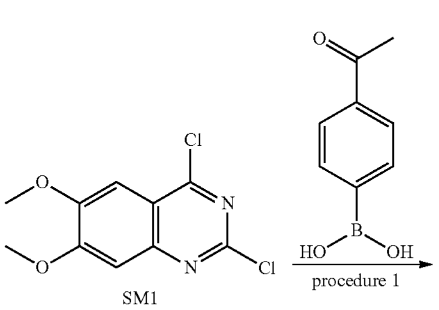

SM1

-continued

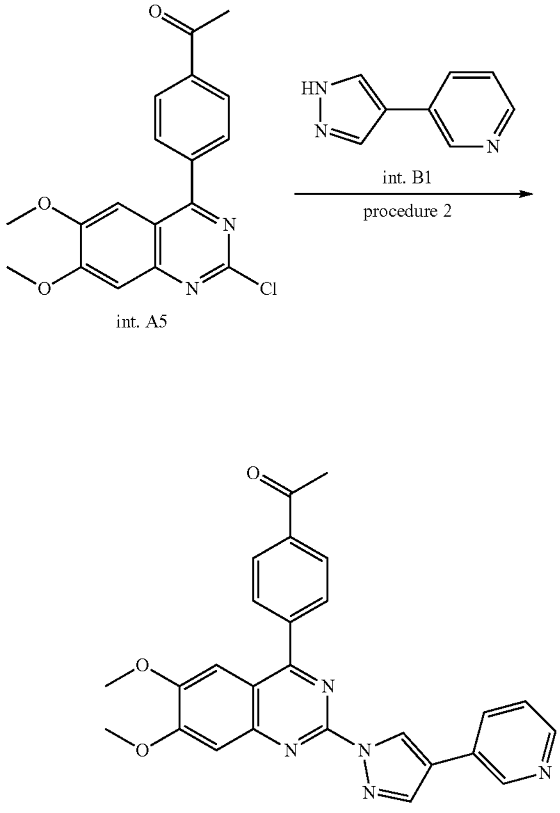

Example 5

Int. A3 was prepared from 2,4-dichloro-6,7-dimethoxy-quinazoline (SM1) and (4-acetylphenyl)boronic acid following general procedure 1, beige solid (yield 74%). $^1$H NMR (400 MHz, $CDCl_3$) δ 8.15 (d, J=8.2 Hz, 2H), 7.88 (d, J=8.2 Hz, 2H), 7.35 (s, 1H), 7.21 (s, 1H), 4.08 (s, 3H), 3.90 (s, 3H), 2.70 (s, 3H).

Example 5 was prepared from int. A5 and int. B1 following general procedure 2, yellow solid (yield 47%). $^1$H NMR (400 MHz, $CDCl_3$+10% $CD_3OD$) δ 9.01 (s, 1H), 8.79 (s, 1H), 8.40 (d, J=4.9 Hz, 1H), 8.16-8.12 (m, 3H), 7.91 (d, J=8.1 Hz, 3H), 7.49 (s, 1H), 7.33 (dd, J=7.7, 5.0 Hz, 2H), 7.19 (s, 1H), 4.05 (s, 3H), 3.85 (s, 3H), 2.67 (s, 3H).

Example 6: 6,7-dimethoxy-2-(4-(4-(methylsulfonyl)phenyl)-1H-pyrazol-1-yl)-4-(quinolin-8-yl)quinazoline

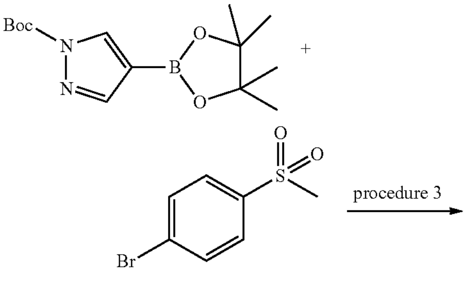

-continued

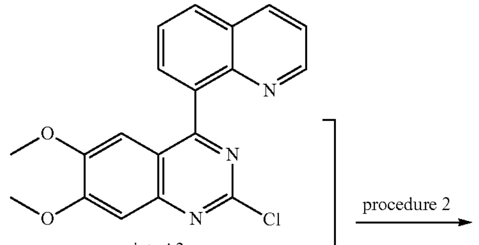

int. A2

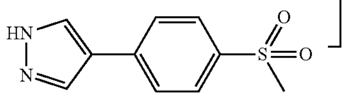

int. B2

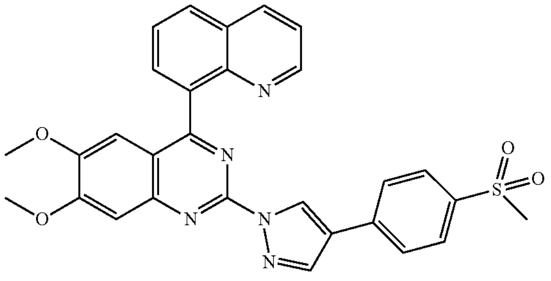

Example 6

Int. B2 was prepared from tert-butyl 4-(4,4,5,5-tetramethyl-1,3,2-dioxaborolan-2-yl)-1H-pyrazole-1-carboxylate and 1-bromo-4-(methylsulfonyl)benzene following general procedure 3, beige solid (yield 58%). $^1$H NMR (400 MHz, DMSO-$d_6$) δ 13.14 (s, 1H), 8.40 (s, 1H), 8.08 (s, 1H), 7.87 (s, 4H), 3.20 (s, 3H).

Example 6 was prepared from int. A2 and int. B2 following general procedure 2, yellow solid (yield 50%). $^1$H NMR (400 MHz, $CDCl_3$) δ 9.08 (s, 1H), 8.81 (d, J=2.6 Hz, 1H), 8.30 (d, J=8.3 Hz, 1H), 8.18 (s, 1H), 8.07 (d, J=8.1 Hz, 1H), 7.93 (dd, J=11.4, 7.8 Hz, 3H), 7.76 (t, J=7.5 Hz, 3H), 7.55 (s, 1H), 7.46 (dd, J=8.2, 4.1 Hz, 1H), 6.63 (s, 1H), 4.07 (s, 3H), 3.57 (s, 3H), 3.05 (s, 3H).

Example 7: 6,7-dimethoxy-2-(4-(4-(methylsulfonyl)phenyl)-1H-pyrazol-1-yl)-4-(quinolin-8-yl)quinazoline

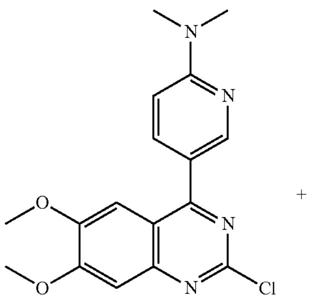

int. A3

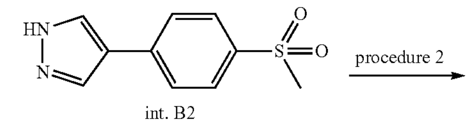

int. B2

-continued

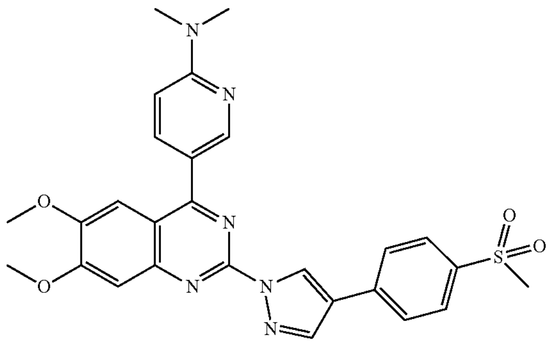

Example 7

Example 7 was prepared from int. A3 and int. B2 following general procedure 2, yellow solid (yield 50%). $^1$H NMR (400 MHz, $CDCl_3$) δ 9.09 (s, 1H), 8.76 (s, 1H), 8.18 (s, 1H), 8.08 (dd, J=8.9, 2.3 Hz, 1H), 7.95 (d, J=8.3 Hz, 2H), 7.79 (d, J=8.3 Hz, 2H), 7.52 (s, 1H), 7.44 (s, 1H), 6.71 (d, J=8.9 Hz, 1H), 4.06 (s, 3H), 3.96 (s, 3H), 3.22 (s, 6H), 3.07 (s, 3H).

Example 8: 6,7-dimethoxy-2-(4-(4-(methylsulfonyl)phenyl)-1H-pyrazol-1-yl)-4-(pyridin-3-yl)quinazoline

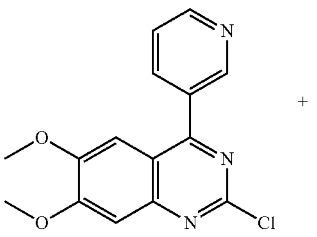

int. A4

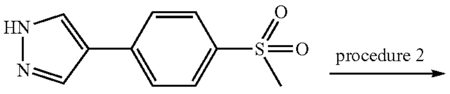

int. B2

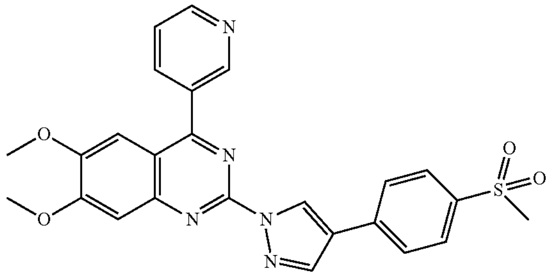

Example 8

Example 8 was prepared from int. A3 and int. B2 following general procedure 2 yellow solid (yield 61%). $^1$H NMR (400 MHz, $CDCl_3$) δ 9.10 (d, J=1.8 Hz, 1H), 9.08 (s, 1H), 8.84 (dd, J=4.8, 1.3 Hz, 1H), 8.24-8.18 (m, 2H), 7.96 (d, J=8.3 Hz, 2H), 7.80 (d, J=8.3 Hz, 2H), 7.59 (dd, J=7.8, 4.9 Hz, 1H), 7.55 (s, 1H), 7.24 (s, 1H), 4.08 (s, 3H), 3.92 (s, 3H), 3.07 (s, 3H).

Example 9: 4-(furan-3-yl)-6,7-dimethoxy-2-(4-(4-(methylsulfonyl)phenyl)-1H-pyrazol-1-yl)quinazoline

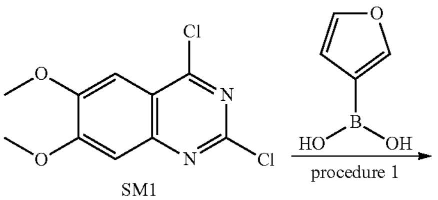

SM1

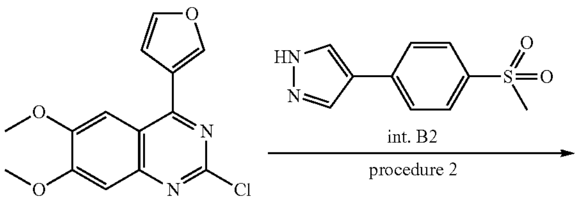

int. A6

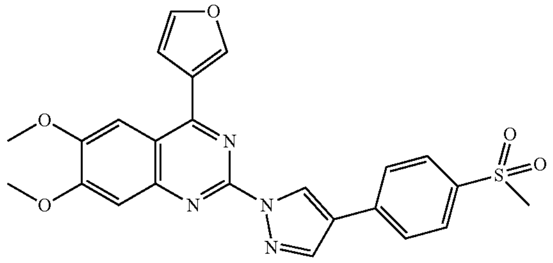

Example 9

Int. A6 was prepared from 2,4-dichloro-6,7-dimethoxy-quinazoline (SM1) and furan-3-ylboronic acid following general procedure 1, beige solid (yield 71%). $^1$H NMR (400 MHz, $CDCl_3$) δ 8.14-8.12 (m, 1H), 7.65-7.62 (m, 1H), 7.47 (s, 1H), 7.30 (s, 1H), 7.05-7.02 (m, 1H), 4.06 (s, 3H), 4.01 (s, 3H).

Example 9 was prepared from int. A6 and int. B2 following general procedure 2, yellow solid (yield 50%). $^1$H NMR (400 MHz, $CDCl_3$) δ 9.07 (s, 1H), 8.20 (d, J=7.7 Hz, 2H), 7.96 (d, J=8.3 Hz, 2H), 7.80 (d, J=8.3 Hz, 2H), 7.67 (s, 1H), 7.50 (s, 2H), 7.12 (s, 1H), 4.06 (s, 3H), 4.01 (s, 3H), 3.08 (s, 3H).

Example 10: 6,7-dimethoxy-2-(4-(4-(methylsulfonyl)phenyl)-1H-pyrazol-1-yl)-4-(thiophen-3-yl)quinazoline

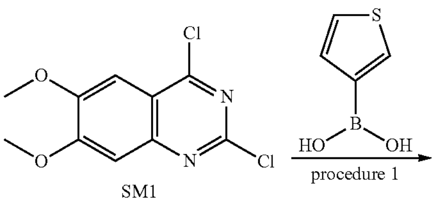

SM1

-continued

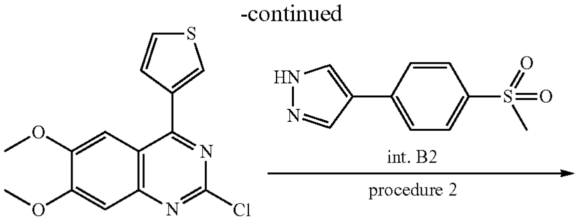

int. A7

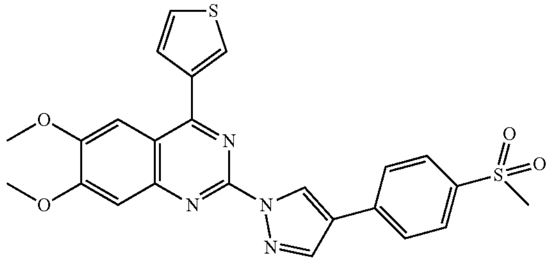

Example 10

Int. A7 was prepared from 2,4-dichloro-6,7-dimethoxy-quinazoline (SM1) and thiophen-3-ylboronic acid following general procedure 1, beige solid (yield 77%). $^1$H NMR (400 MHz, $CDCl_3$) δ 7.96 (d, J=3.0 Hz, 1H), 7.63 (d, J=5.0 Hz, 1H), 7.54 (dd, J=5.0, 3.0 Hz, 1H), 7.49 (s, 1H), 7.31 (s, 1H), 4.06 (s, 3H), 3.98 (s, 3H).

Example 10 was prepared from int. A7 and int. B2 following general procedure 2, yellow solid (yield 60%). $^1$H NMR (400 MHz, DMSO-$d_6$) δ 9.39 (s, 1H), 8.55 (dd, J=2.8, 1.2 Hz, 1H), 8.48 (s, 1H), 8.11 (d, J=8.5 Hz, 2H), 7.97-7.91 (m, 3H), 7.87 (dd, J=5.0, 2.9 Hz, 1H), 7.61 (s, 1H), 7.45 (s, 1H), 4.04 (s, 3H), 3.96 (s, 3H), 3.25 (s, 3H). $^{13}$C NMR (101 MHz, DMSO-$d_6$) δ 160.87, 156.59, 150.71, 150.01, 149.88, 140.82, 138.62, 138.09, 136.73, 130.23, 129.30, 127.66 (2C), 127.29, 127.21, 126.08 (2C), 122.58, 116.16, 106.67, 104.13, 56.36, 55.70, 43.61. LC-MS: $[M+H]^+$ 493.4

Example 11: 6,7-dimethoxy-2-(4-(4-(methylsulfonyl)phenyl)-1H-pyrazol-1-yl)-4-(p-tolyl)quinazoline

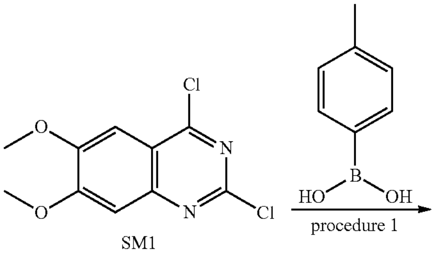

SM1

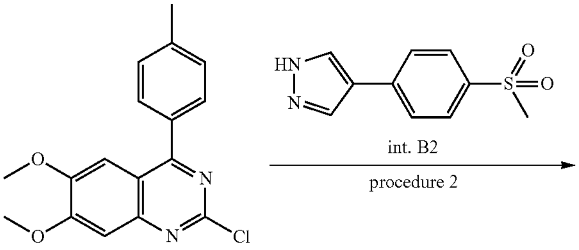

int. A8

-continued

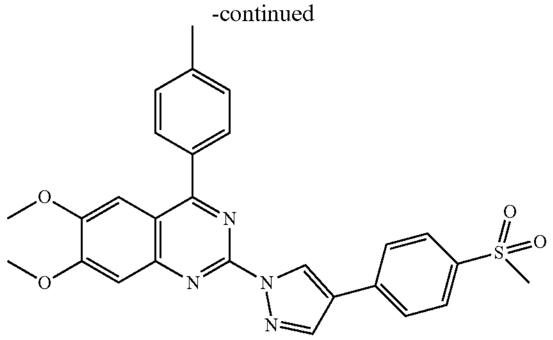

Example 11

Int. A8 was prepared from 2,4-dichloro-6,7-dimethoxy-quinazoline (SM1) and p-tolylboronic acid following general procedure 1, beige solid (yield 72%). $^1$H NMR (400 MHz, $CDCl_3$) δ 7.96 (d, J=3.0 Hz, 1H), 7.63 (d, J=5.0 Hz, 1H), 7.54 (dd, J=5.0, 3.0 Hz, 1H), 7.49 (s, 1H), 7.31 (s, 1H), 4.06 (s, 3H), 3.98 (s, 3H).

Example 11 was prepared from int. A8 and int. B2 following general procedure 2, yellow solid (yield 41%). $^1$H NMR (400 MHz, $CDCl_3$) δ 9.12 (s, 1H), 8.20 (s, 1H), 7.96 (d, J=8.4 Hz, 2H), 7.87-7.71 (m, 4H), 7.56 (s, 1H), 7.43 (d, J=7.9 Hz, 2H), 7.38 (s, 1H), 4.08 (s, 3H), 3.92 (s, 3H), 3.08 (s, 3H), 2.51 (s, 3H).

Example 12: 2-(4-(4-(methylsulfonyl)phenyl)-1H-pyrazol-1-yl)-4-(thiophen-3-yl)quinazoline

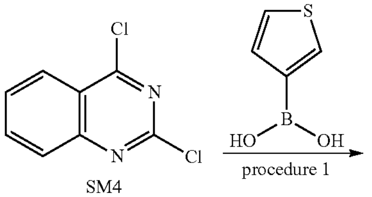

SM4

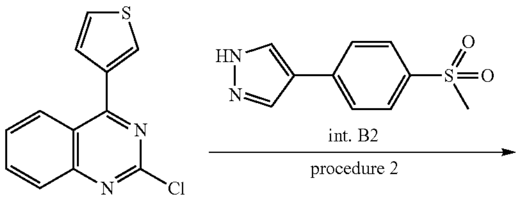

int. A9

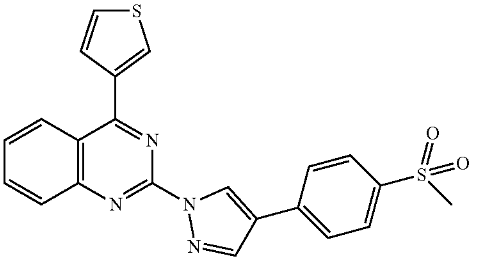

Example 12

Int. A9 was prepared from 2,4-dichloroquinazoline (SM4) and thiophen-3-ylboronic acid following general procedure 1, beige solid (yield 60%). $^1$H NMR (400 MHz, cdcl$_3$) δ 8.32 (d, J=8.5 Hz, 1H), 8.05-7.99 (m, 2H), 7.97-7.91 (m, 1H), 7.69-7.63 (m, 2H), 7.56-7.52 (m, 1H).

Example 12 was prepared from int. A9 and int. B2 following general procedure 2, yellow solid (yield 33%). $^1$H NMR (400 MHz, cdcl$_3$) δ 9.17 (s, 1H), 8.35 (d, J=8.4 Hz, 1H), 8.24 (s, 1H), 8.22 (d, J=8.5 Hz, 1H), 8.09-8.07 (m, 1H), 7.99 (d, J=7.2 Hz, 2H), 7.97-7.93 (m, 1H), 7.84 (d, J=8.1 Hz, 2H), 7.76 (d, J=5.0 Hz, 1H), 7.66-7.62 (m, 1H), 7.62-7.58 (m, 1H), 3.09 (s, 3H).

Example 13: 7-(4-ethylpiperazin-1-yl)-2-(4-(4-(methylsulfonyl)phenyl)-1H-pyrazol-1-yl)-4-(thiophen-3-yl)quinazoline

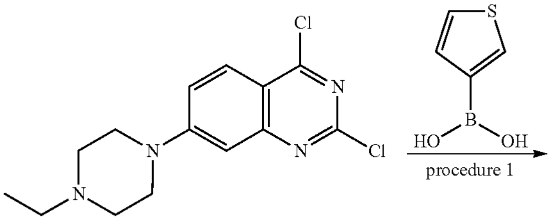

SM5

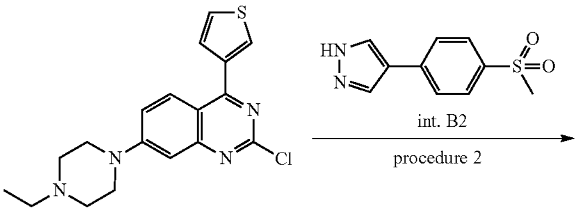

int. A10

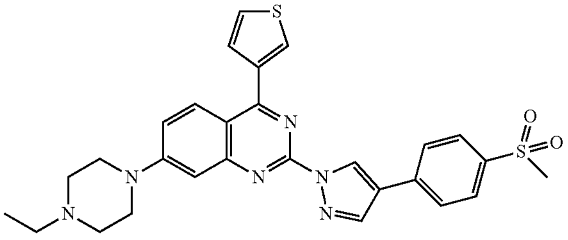

Example 13

Int. A10 was prepared from 2,4-dichloro-7-(4-ethylpiperazin-1-yl)quinazoline (SM5) and thiophen-3-ylboronic acid following general procedure 1, beige solid (yield 40%). LC-MS: 359.

Example 15 was prepared from int. A10 and int. B2 following general procedure 2, yellow solid (yield 33%). $^1$H NMR (400 MHz, cdcl$_3$) δ 9.12 (s, 1H), 8.20 (s, 1H), 8.13 (d, J=9.5 Hz, 1H), 7.97 (d, J=6.7 Hz, 3H), 7.82 (d, J=6.8 Hz, 2H), 7.70 (d, J=5.0 Hz, 1H), 7.58-7.53 (m, 1H), 7.38 (s, 1H), 7.25 (s, 1H), 3.58 (m, 4H), 3.09 (s, 3H), 2.69 (m, 4H), 2.56 (m, 2H), 1.19 (t, J=7.1 Hz, 3H).

Example 14: 4-(1-(6,7-dimethoxy-4-(thiophen-3-yl)quinazolin-2-yl)-1H-pyrazol-4-yl)-N-(2-(dimethylamino)ethyl)benzenesulfonamide

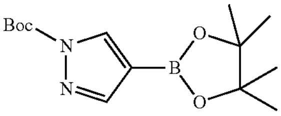

+

-continued

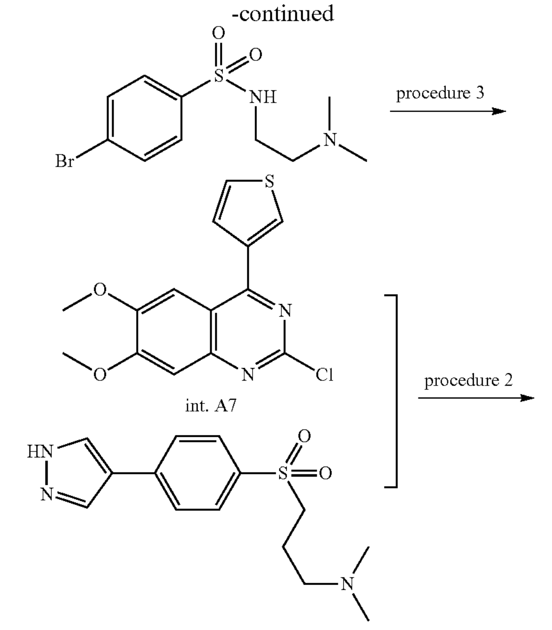

int. A7 int. B3

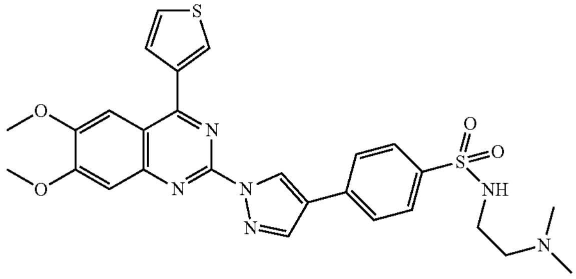

Example 14

Int. B1 was prepared from tert-butyl 4-(4,4,5,5-tetramethyl-1,3,2-dioxaborolan-2-yl)-1H-pyrazole-1-carboxylate and 4-bromo-N-(2-(dimethylamino)ethyl)benzenesulfonamide following general procedure 3, beige solid (yield 74%). $^{1}$H NMR (400 MHz, cdcl$_3$) δ 7.93 (s, 2H), 7.86 (d, J=7.2 Hz, 2H), 7.63 (d, J=8.1 Hz, 2H), 3.03-2.97 (m, 2H), 2.35 (t, J=5.6 Hz, 2H), 2.09 (s, 6H).

Example 14 was prepared from int. A7 and int. B3 following general procedure 2, yellow solid (yield 33%). $^{1}$H NMR (400 MHz, cdcl$_3$) δ 9.09 (s, 1H), 8.20 (s, 1H), 8.03 (s, 1H), 7.92 (d, J=6.7 Hz, 2H), 7.77 (d, J=6.7 Hz, 2H), 7.73 (d, J=4.5 Hz, 1H), 7.60 (s, 1H), 7.55 (s, 1H), 7.55 (s, 1H), 4.09 (s, 3H), 4.00 (s, 3H), 3.07 (t, J=5.1 Hz, 2H), 2.46 (t, J=5.0 Hz, 2H), 2.19 (s, 6H).

Example 15: 6,7-dimethoxy-4-(4-((4-methylpiperazin-1-yl)sulfonyl)phenyl)-2-(4-(4-(methylsulfonyl)phenyl)-1H-pyrazol-1-yl)quinazoline

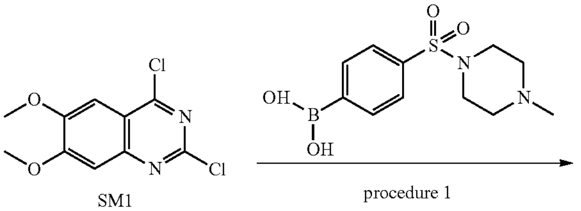

SM1

-continued

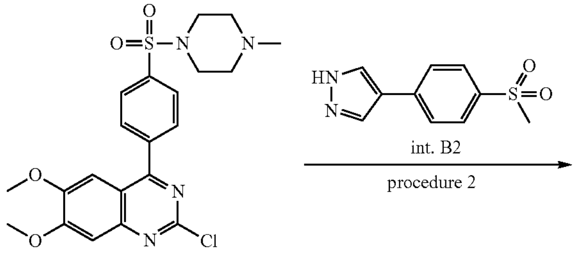

int. A11

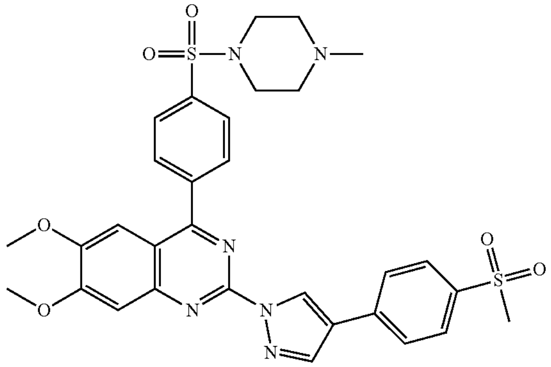

Example 15

Int. All was prepared from 2,4-dichloro-6,7-dimethoxyquinazoline (SM1) and (4-((4-methylpiperazin-1-yl)sulfonyl)phenyl)boronic acid following general procedure 1, beige solid (yield 62%). LC-MS: 463.

Example 17 was prepared from int. All and int. B2 following general procedure 2, yellow solid (yield 47%). $^{1}$H NMR (400 MHz, cdcl$_3$) δ 9.11 (d, J=0.8 Hz, 1H), 8.23 (d, J=0.8 Hz, 1H), 8.01 (s, 4H), 7.98 (d, J=8.5 Hz, 2H), 7.84 (d, J=8.5 Hz, 2H), 7.59 (s, 1H), 7.19 (s, 1H), 4.10 (s, 3H), 3.94 (s, 3H), 3.26 (m, 4H), 3.09 (s, 3H), 2.66 (m, 4H), 2.43 (s, 3H).

Example 16: 6,7-dimethoxy-4-(3-methoxyphenyl)-2-(4-(4-(methylsulfonyl)phenyl)-1H-pyrazol-1-yl)quinazoline

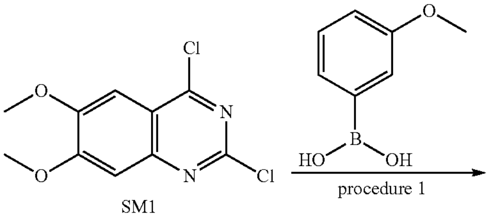

SM1

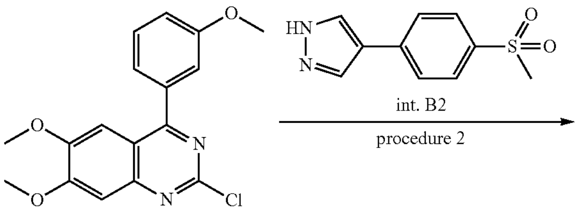

int. A12

-continued

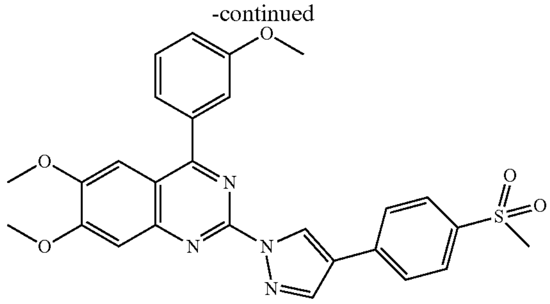

Example 16

Int. A12 was prepared from 2,4-dichloro-6,7-dimethoxyquinazoline (SM1) and (3-methoxyphenyl)boronic acid following general procedure 1, beige solid (yield 62%). 41 NMR (400 MHz, cdcl$_3$) δ 7.47 (t, J=7.9 Hz, 1H), 7.35-7.28 (m, 4H), 7.10 (dd, J=8.3, 1.6 Hz, 1H), 4.06 (s, 3H), 3.91 (s, 3H), 3.89 (s, 3H).

Example 16 was prepared from int. A12 and int. B2 following general procedure 2, yellow solid (yield 35%). $^1$H NMR (400 MHz, cdcl$_3$) δ 9.12 (d, J=0.8 Hz, 1H), 8.21 (d, J=0.8 Hz, 1H), 7.97 (d, J=8.5 Hz, 2H), 7.81 (d, J=8.5 Hz, 2H), 7.57 (s, 1H), 7.56-7.51 (m, 1H), 7.43-7.39 (m, 1H), 7.38 (dd, J=2.5, 1.5 Hz, 1H), 7.37 (s, 1H), 7.15 (ddd, J=8.3, 2.6, 0.9 Hz, 1H), 4.08 (s, 3H), 3.92 (m, 6H), 3.08 (s, 3H).

Example 17. TRIM28 Mediated Poly-ubiquitination of TRDMT1 Renders Drug Resistance

TRDMT1$^{G155V}$ Mutant is Highly Poly-ubiquitinated

TRDMT1 was found consistently up-regulated in hundreds of tumor samples listed in the COSMIC database and more than 90 somatic mutations in TRDMT1 have been identified in tumors of various tissue types, while little is known regarding how its mutations influence tumorigenesis and affect treatment response in cancer. TRDMT1-mediated mRNA m$^5$C formation promoted HR in the transcribed genome. The role of TRDMT1 raises the possibility that TRDMT1-regulated mRNA m$^5$C modification might be involved in resistance to other damage agents utilizing HR to repair damage. Cisplatin induces DNA cross-linking and subsequent DSBs and utilizes HR for repair. Enhanced sensitivities of cells treated with siTRDMT1 to cisplatin were observed in multiple cell lines including U2OS, breast cancer cell line MCF-7, and ovarian cancer cell line SKOV3 (FIG. 1A), confirming that downregulation of TRDMT1 increases the sensitivity of tumor cells to Cisplatin.

Figure 1E:
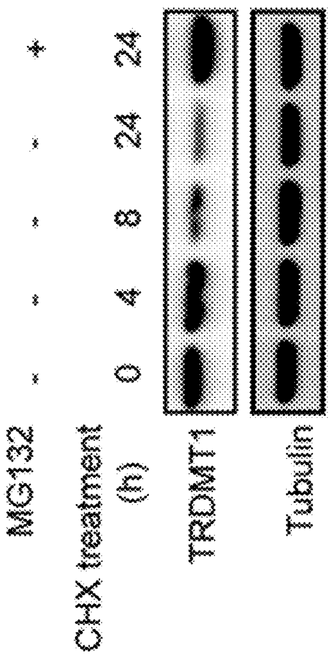
Figure 1F:
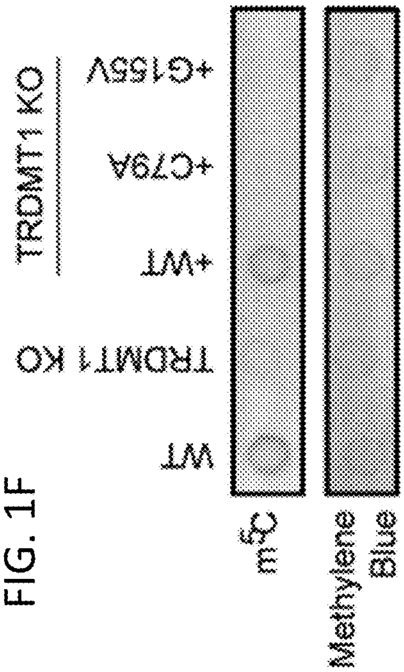
Figure 1G:
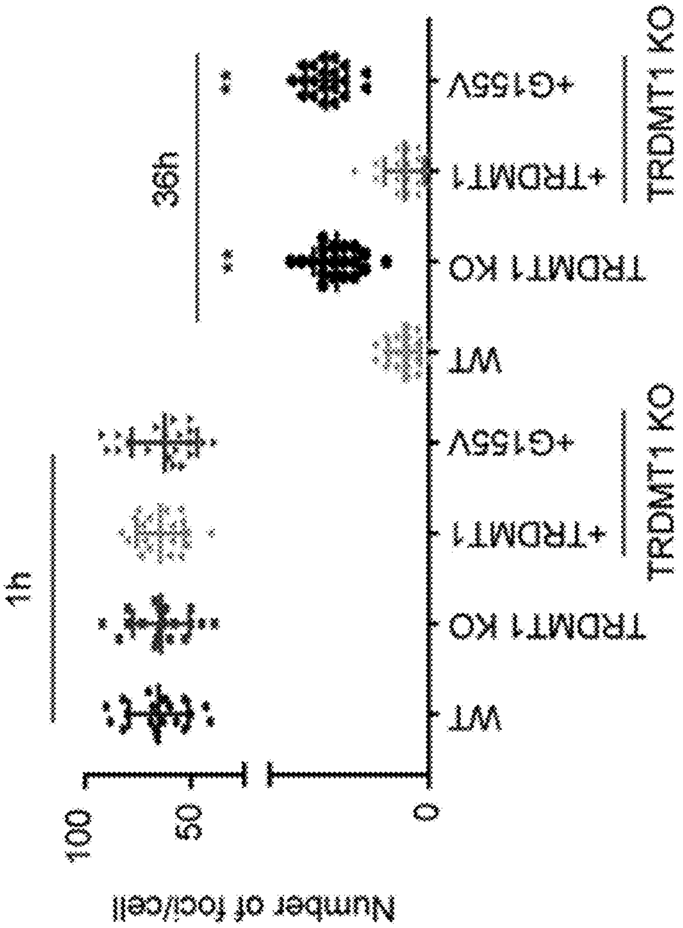
Figure 1H:
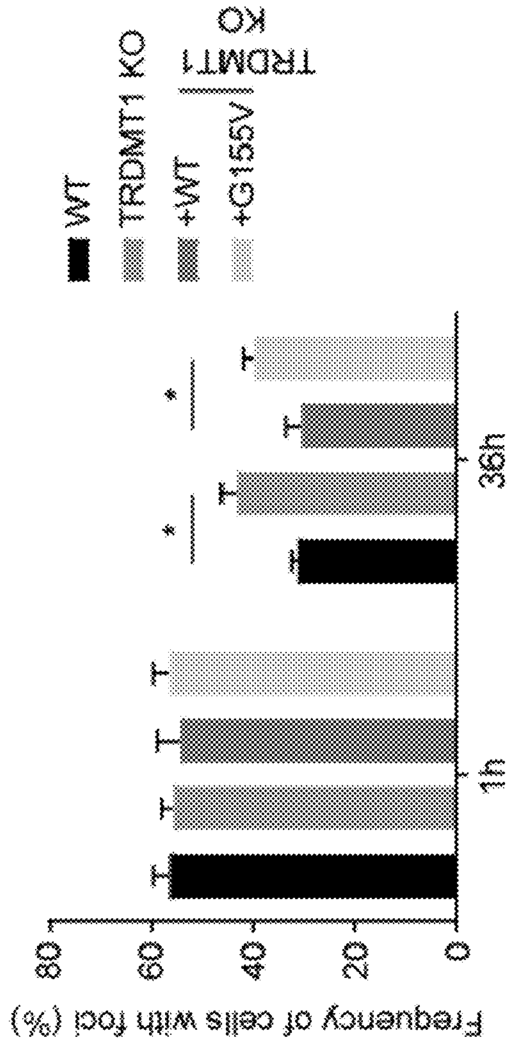
Figure 1I:
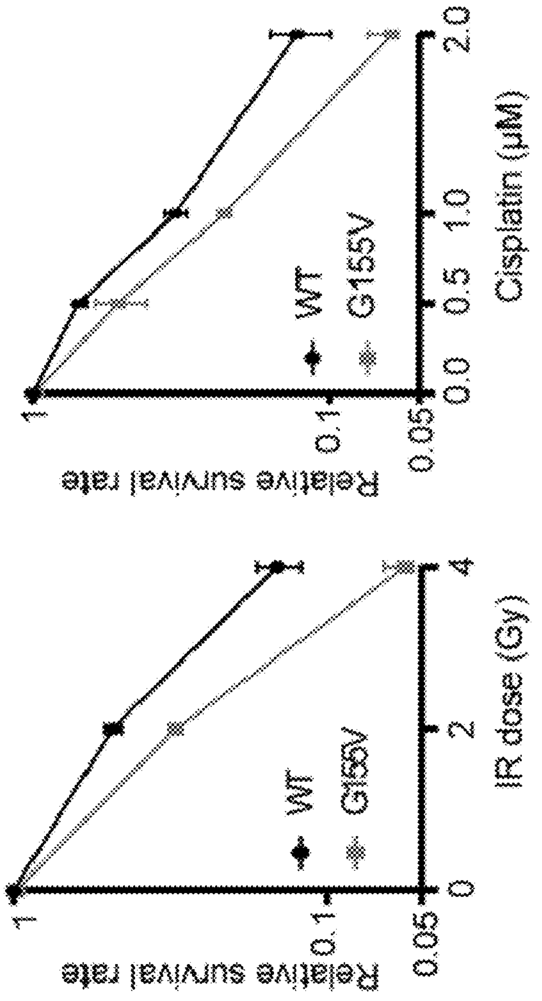
(FIG. 1I) The survival rate of the cells after IR or Cisplatin in GFP-tagged TRDMT1$^{WT}$ or TRDMT1$^{G155V}$ transfected TRDMT1 KO U2OS-TRE cells (n=3, Mean±SD). Statistical analysis was done with the Student-t-test, *: p<0.05; : p<0.01; *: p<0.001; ****: p<0.0001 for all the figures.

G155 is a hotspot of somatic cancer mutations, especially in ovarian cancer, which locates on the back-side, right in front of motif VIII of TRDMT1 (FIG. 1B). The Cancer Genome Atlas (TCGA)-13-0720 reveals that a patient bearing TRDMT1$^{G155V}$ mutation is a super responder to the primary Platinum treatment, displaying a complete response to Cisplatin treatment and exhibiting a better prognosis. Eventually, the patient had almost a year longer overall survival time compared with the patients at the same clinical stage (stage III). Cancer mutations may reduce the stability of the protein, alter its localization or affect the methylation activity of RNA substrates. Comparing with stably expressed TRDMT1$^{WT}$ and TRDMT1$^{C79A}$, a methyltransferase catalytic deficiency mutant, the protein level of TRDMT1 was consistently low in TRDMT1$^{G155V}$ stably expressed 293 TRDMT1 KO cell line (FIG. 1C). To understand the low expression of TRDMT1 is due to protein instability or degradation, we examined the ubiquitination level of TRDMT1 in TRDMT1$^{WT}$ or TRDMT1$^{G155V}$ stable expressed 293 TRDMT1 KO cells. The poly-ubiquitination level was significantly higher in TRDMT1$^{G155V}$ stable expressed cell line (FIG. 1D). In cells, degradation of TRDMT1 was through MG132 mediated poly-ubiquitination degradation (FIG. 1E). TRDMT1 is an mRNA m5C writer at sites of transcribed damage and studies indicate the m$^5$C in mRNA is required for damage removal in nucleus and drug-resistance of cells. The level of m$^5$C in mRNA extraction was decreased in TRDMT1$^{G155V}$ stably expressed TRDMT1 KO 293 cell line compared to WT (FIG. 1F). γH2AX clearance was delayed at sites of damage (FIG. 1G, FIG. 1H) and the survival rates of both Cisplatin and IR treated cells were decreased in TRDMT1$^{G155V}$ compared to TRDMT1$^{WT}$ expressed TRDMT1 KO cells (FIG. 1I). These results indicate that insufficient repair capacity of G155V-mutated TRDMT1 contributes to cell death after damage.

Figure 2A:
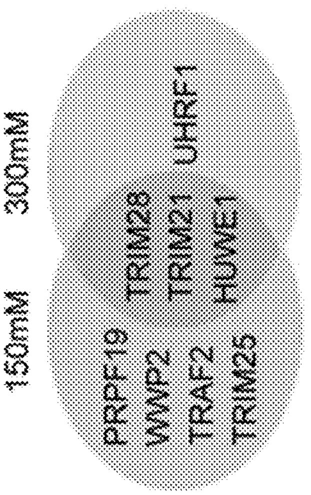
FIGS. 2A-2E show that TRDMT1 is ubiquitinated by E3 ligase TRIM28 at sites of DNA damage.
Figure 2B:
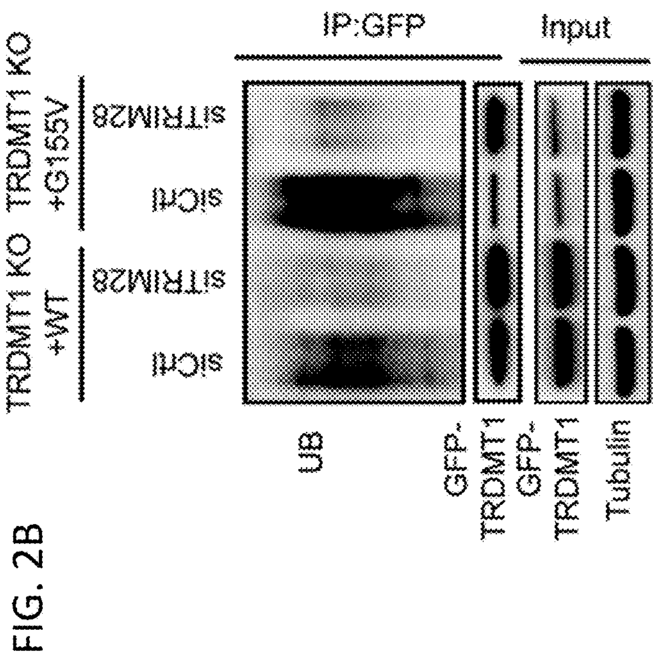
Figure 2C:
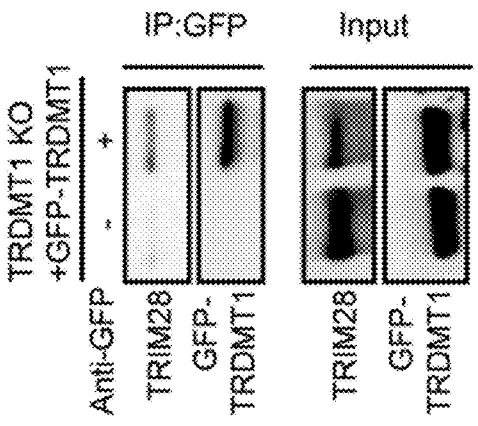
Figure 2D:
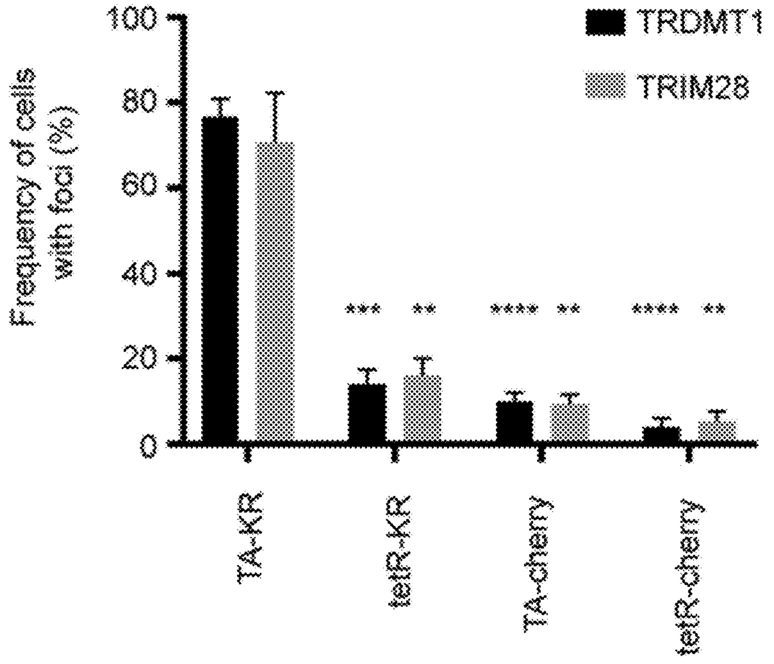
Figure 2E:
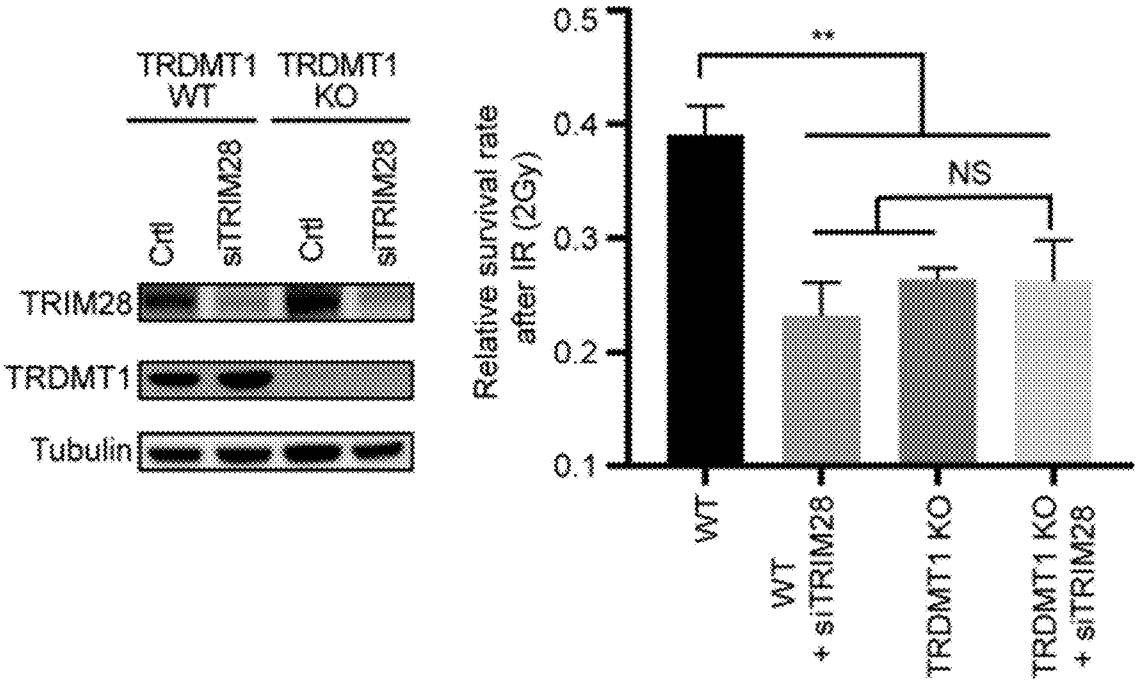

TRDMT1 is Ubiquitinated by TRIM28 at Transcriptionally Active Sites of DNA Damage To understand how TRDMT1 is regulated via ubiquitination, we tried to identify the E3 ligases. We pulled down TRDMT1 and performed the mass spectrometry analysis to determine its interacting proteins. Among them, we listed all E3 ligases pulled down by TRDMT1 after washing with sodium chloride at either 150 mM or 300 mM concentration (FIG. 2A). In the E3 ligases pool pulled down by TRDMT1, TRIM28 was the only E3 ligase detected under both washing conditions, and the number of peptides was significantly increased compared to the control group (FIG. 2A). TRIM28, also named KAP-1, is known to be involved in the upstream of recruitment of repair proteins of DSBs via modulating chromatin relaxation. We knocked down TRIM28 and found the ubiquitination level of TRDMT1 was indeed significantly decreased in TRDMT1$^{WT}$ and further decreased in TRDMT1$^{G155V}$ stably expressed TRDMT1 KO 293 cells (FIG. 2B), suggesting that TRIM28 is the E3 ligase for TRDMT1. Moreover, the interaction between TRIM28 and TRDMT1 was confirmed using TRIM28 in IP (FIG. 2C). To pursue the putative link between mRNA m$^5$C modification and DNA damage response regulated by TRDMT1, we used KillerRed (KR), a light-excitable and superoxide-releasing chromophore, to conditionally generate local DSBs at a genomic locus in U2OS Tet Response Element (TRE) cells. When a fusion protein of KR and the transcription activator VP16 (TA-KR) is expressed in these cells, it binds to the array and activates transcription locally, upon light activation, TA-KR releases free radicals intensively at the specific locus of the genome and induces DSBs at the locus. In this system, TA-KR represents the sites DSBs in the transcribed genome; tetR-KR represents sites of damage without transcription; TA-cherry represents actively transcribed sites without damage; and tetR-cherry is the maker of TRE integration without damage and active transcription. We found that both TRDMT1 and TRIM28 were preferentially recruited at sites of TA-KR but not at sites of tetR-KR, TA-cherry, and tetR-cherry (FIG. 2D), indicating that TRDMT1 and TRIM28 are enriched at transcribed damage sites. Knocking down TRIM28 in TRDMT1 KO cells did not further sensitize cells to Cisplatin and IR compared to single KD or KO of single gene, indicating that TRIM28 facilitates repair of DSBs in a TRDMT1-dependent manner (FIG. 2E).

Figure 3A:
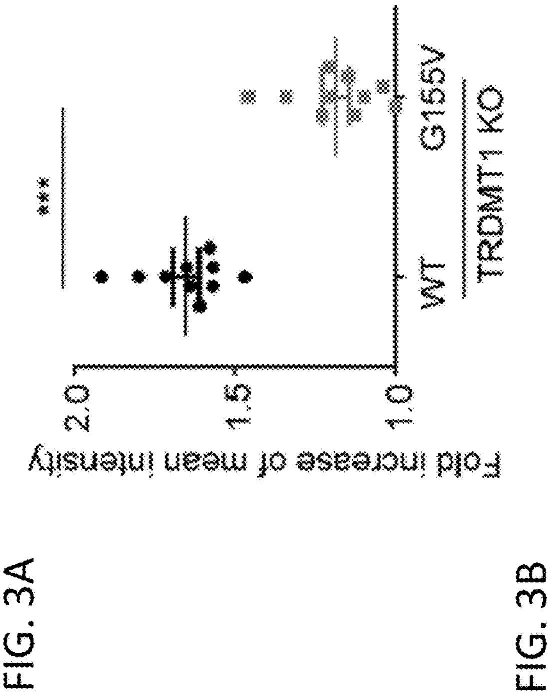
FIGS. 3A-3B show TRDMT1$^{G155V}$ expression diminishes $m^5C$ and the response of repair factors at damage sites.
Figure 3B:
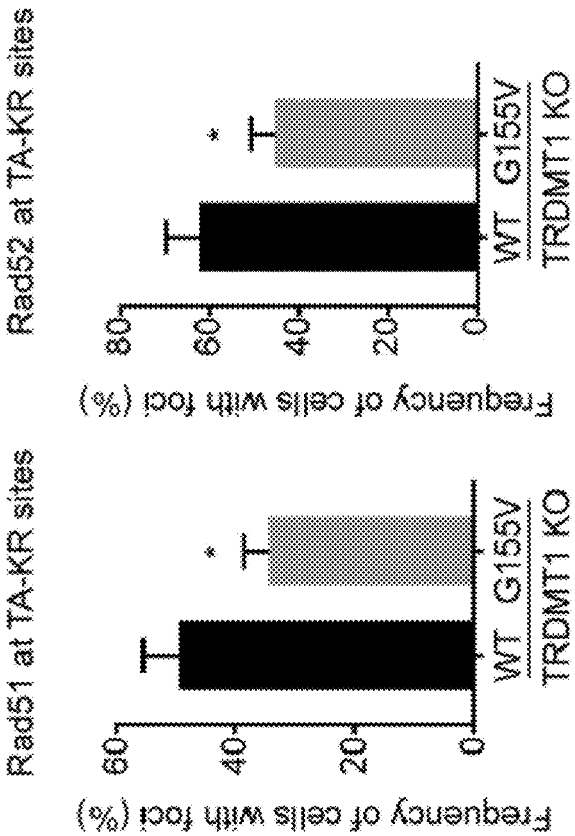

Having shown that both TRDMT1 and TRIM28 are recruited to damage sites of the transcribed genome, we examined the damage response of TRDMT1$^{G155V}$ mutant. The TRDMT1$^{G155V}$ foci intensity was significantly decreased at the TA-KR site in TRDMT1 U2OS-TRE cells compared to TRDMT1$^{WT}$(FIG. 3A). This is reasonable since TRDMT1$^{G155V}$ mutant degraded much faster in cells (FIG. 1D). Since TRDMT1 is a "writer" of $m^5C$ in mRNA during the DNA damage response, not surprisingly, TRDMT1$^{G155V}$ failed to restore the local $m^5C$ level in U2OS-TRE (FIG. 3D). Notably, in contrast to TRDMT1', TRDMT1$^{G155V}$ failed to restore the recruitment of RAD51 and RAD52 at damage sites, which are critical factors of TC-HR, at TA-KR sites in U2OS-TRE TRDMT1 KO cells (FIG. 3D). These results indicate that the complete response to Cisplatin treatment of TRDMT1$^{G155V}$ bearing patient might due to defective DNA repair for DSBs.

Ubiquitination of TRDMT1 at its K251 is Required for Cell Survival after Damage

Figure 4A:
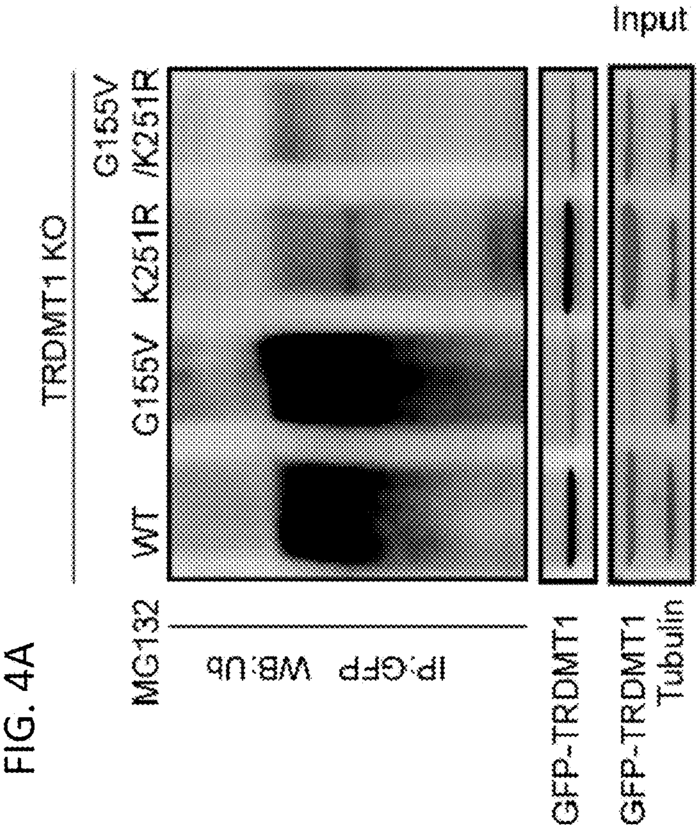
FIGS. 4A-4C show Ubiquitination of TRDMT1 at its K251 is required for cell survival.
Figure 4B:
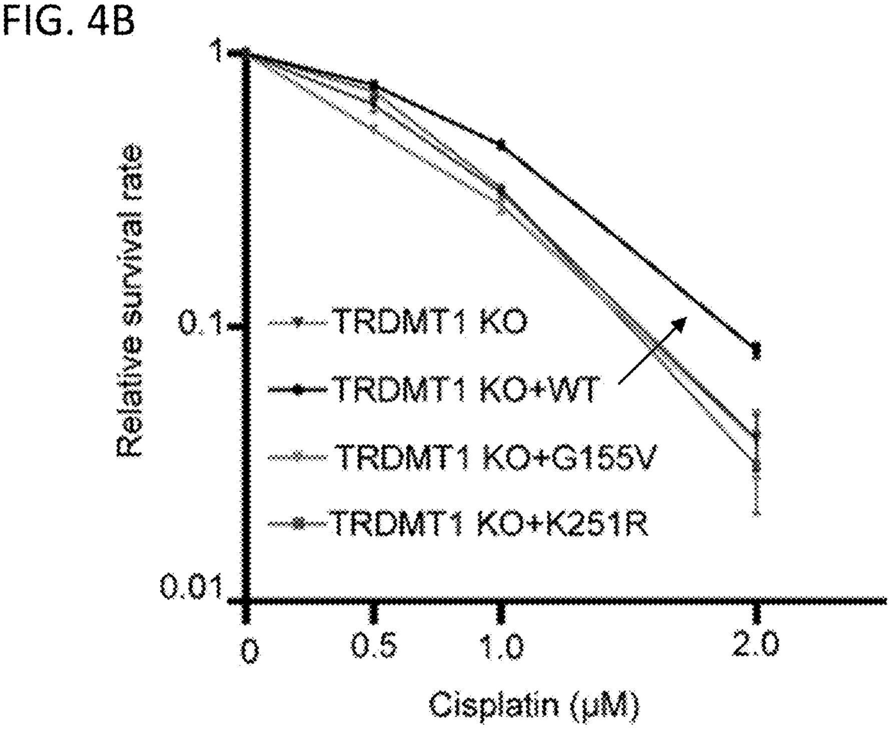
Figure 4C:
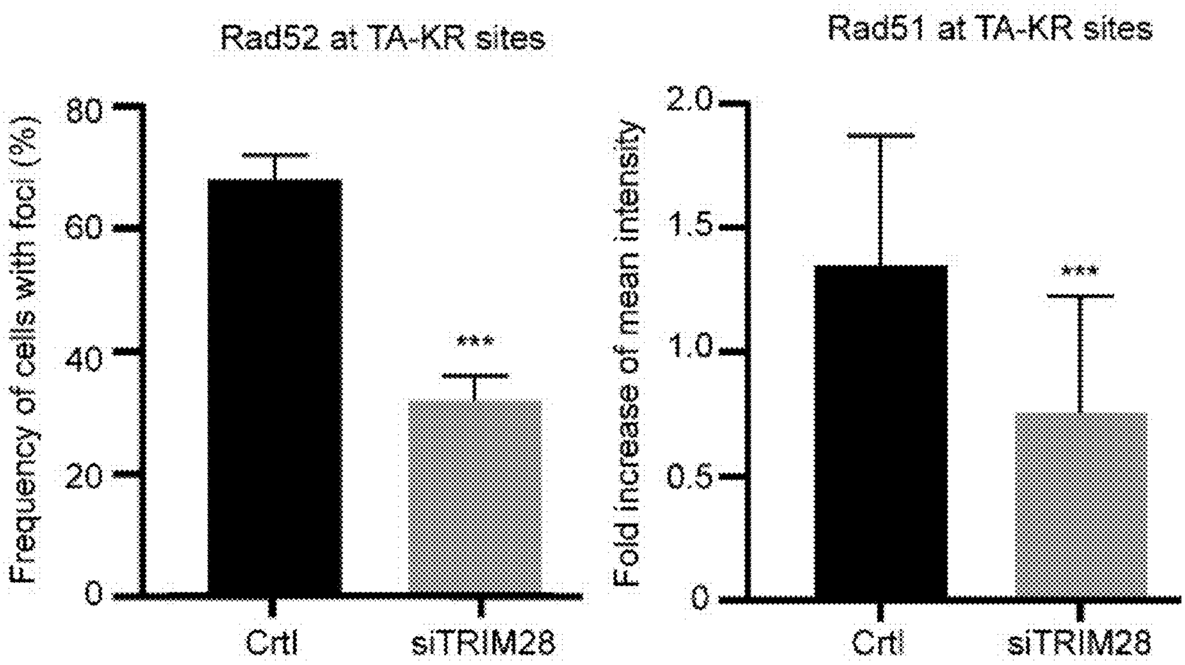
Figure 4D:
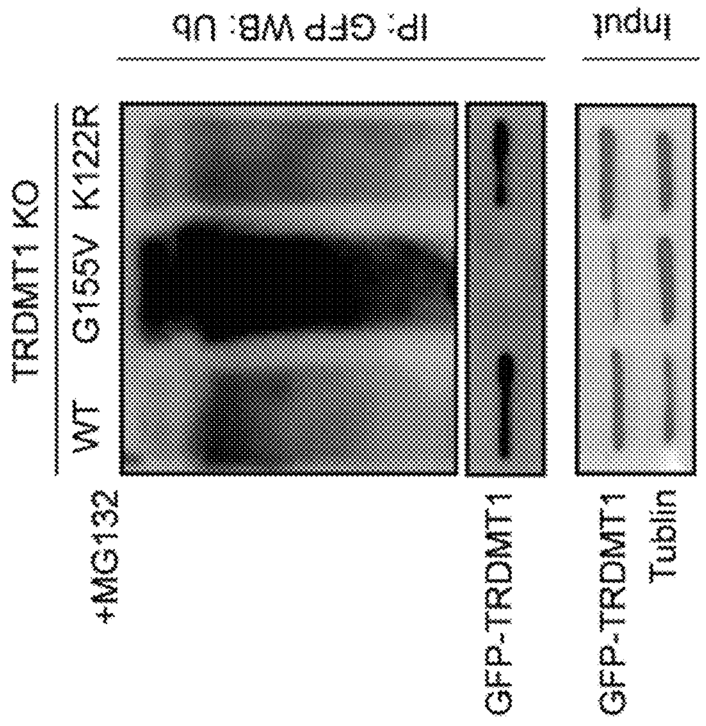
FIGS. 4D-4E show lysine K122R mutant did not alter the level of ubiquitination of TRDMT1 (FIG. 4D) 293 TRDMT1 KO cells were transfected with GFP-tagged TRDMT1$^{WT}$ TRDMT1$^{G155V}$ or TRDMT1$^{K122R}$ Cells were pulled with anti-GFP and immunoblot with anti-Ub.

The ubiquitin must be attached to a lysine site of a substrate. Given that TRIM28 co-localizes and is required poly-ubiquitination TRDMT1, we tried to determine the ubiquitination site of TRDMT1. There are 25 lysine residues in TRDMT1. The fact that TRDMT1$^{G155V}$ is highly ubiquitinated prompts us to search any lysine residues near to the glycine 155. By analyzing the crystal structure of TRDMT1 from the database (uniprot.org), we found that lysine 251 is the nearest lysine site to glycine 155. We constructed GFP-tagged TRDMT1$^{WT}$, TRDMT1$^{G155V}$ TRDMT1$^{K251R}$ and TRDMT1$^{G155V/K251R}$ mutants and transfected them into TRDMT1 KO U2OS-TRE cells. We found that both TRDMT1$^{K251R}$ and TRDMT1$^{G155V/K251R}$ exhibited decreased the ubiquitination of TRDMT1 (FIG. 4A). The level of ubiquitination of TRDMT1$^{G155V/K251R}$ was decreased further compared to that of TRDMT1$^{K251R}$ (FIG. 4A), supporting the idea that G155V mutant leads to exposure of lysine K251 to be targeted for ubiquitination. In contrast, mutation of another lysine 122, K122R, which is located far away from G155, did not alter the level of ubiquitination of TRDMT1 (FIG. 4D).

Figure 4E:
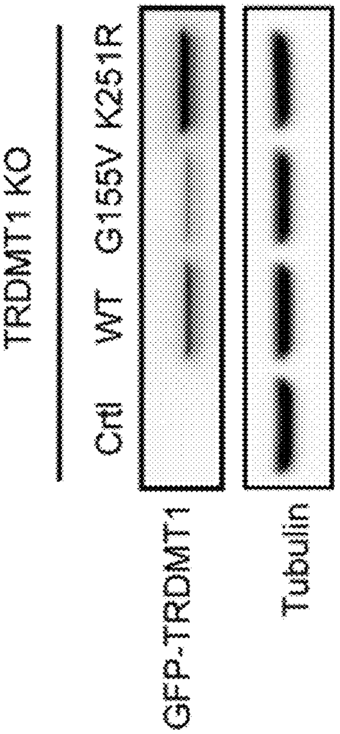

To confirm the role of K251 mediated polyubiquitination in DNA repair, we measured the cell survival after damage. TRDMT1$^{K251R}$ expressed cells were as sensitive as TRDMT1 KO cells to Cisplatin compared to TRDMT1$^{wt}$ expressed TRDMT1 KO cells (FIG. 4B, FIG. 4E). Thus, either hyper-ubiquitination or loss of ubiquitination of TRDMT1 could sensitize the cells to DNA damage. Interestingly, siTRIM28 also decreased the recruitment of Rad52 and Rad51 at TA-KR sites (FIG. 4C), indicating that level of TRDMT1 at sites of DNA damage is tightly regulated for repair progression and cell survival.

Reduced TRDMT1 Expression Contributes to Cisplatin Sensitization In Vivo.

Figure 5A:
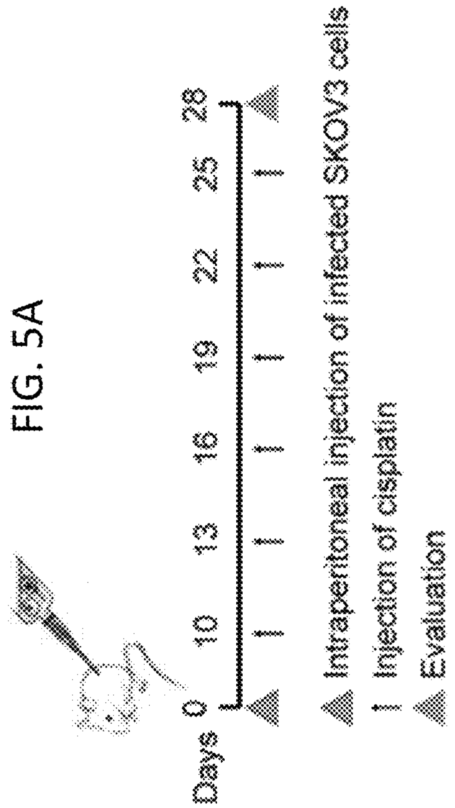
FIGS. 5A-5E show reduced TRDMT1 expression renders Cisplatin sensitization in vivo.
Figure 5B:
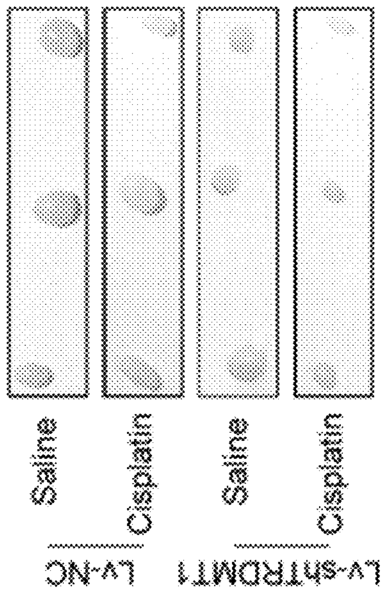
Figure 5D:
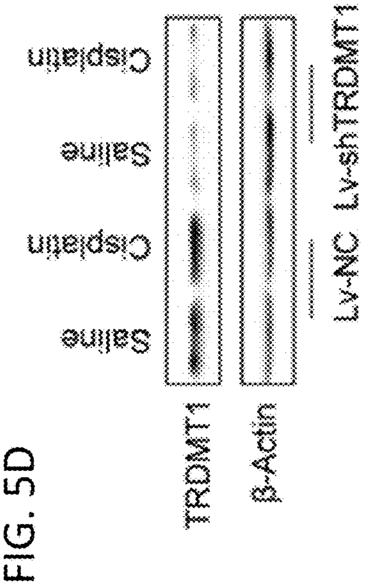
Figure 5E:
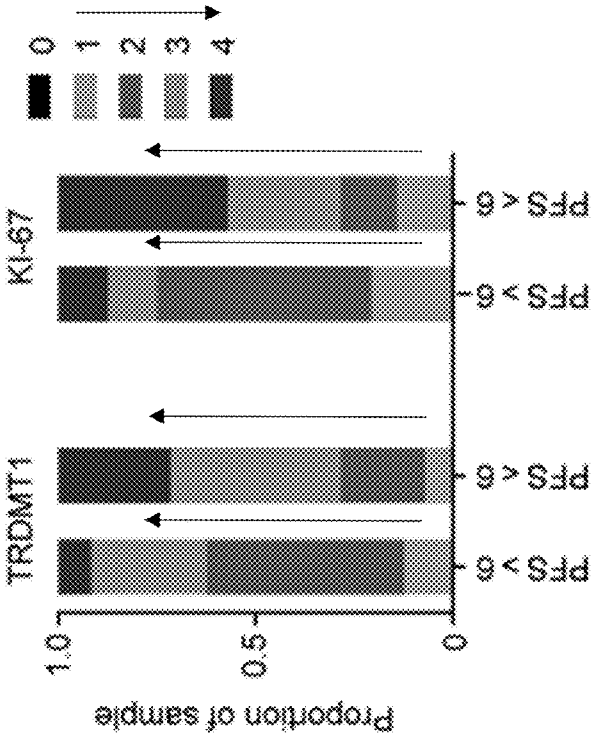
Figure 5C:
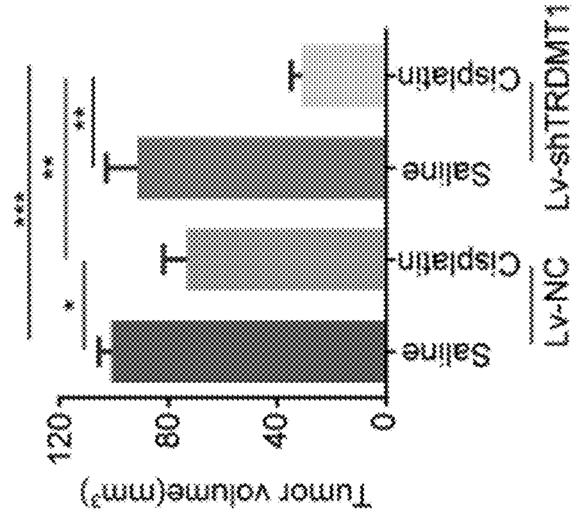

Given that TRDMT1 suppression leads to increased Cisplatin and IR sensitivity in cells, we validated the role of TRDMT1 in drug resistance in vivo, using a model of epithelial ovarian cancer (EOC) by subcutaneous injection of SKOV3 cells which were infected with lentiviruses (LV) carrying TRDMT1-RNAi (Lv-shTRDMT1) or NC-RNAi (Lv-NC) was established (FIG. 5A). There were no significant differences in tumor size were detected between TRDMT1-depleted tumors and the control tumors, However, with cisplatin treatment, xenografts developed from Lv-shTRDMT1 infected SKOV3 cells grew statistically smaller (FIG. 5B-5D). In Lv-shTRDMT1 infected tumor tissue, we observed an overall decrease of $m^5C$. These results suggesting TRDMT1 depletion sensitizes EOC cells to Cisplatin, which correlates to the level of $m^5C$. To further explore the correlation between TRDMT1 and drug resistance, we quantified TRDMT1 and a marker of cell proliferation (Ki67) expression in primary EOC specimens derived from 38 EOC patients. TRDMT1 protein level and the number of Ki67-positive cells elevated in tumors from patients with progression-free survival (PFS)G6 months (clinically described as platinum-resistant), while their expression was decreased in tumors from patients with PFS>6 months (platinum-sensitive) (FIG. 5E), supporting that high TRDMT1 expression is correlated to enhanced drug resistance.

The TRDMT1 Inhibitor YW-1842 Affects $m^5C$ Induction and HR.

Figure 6A:
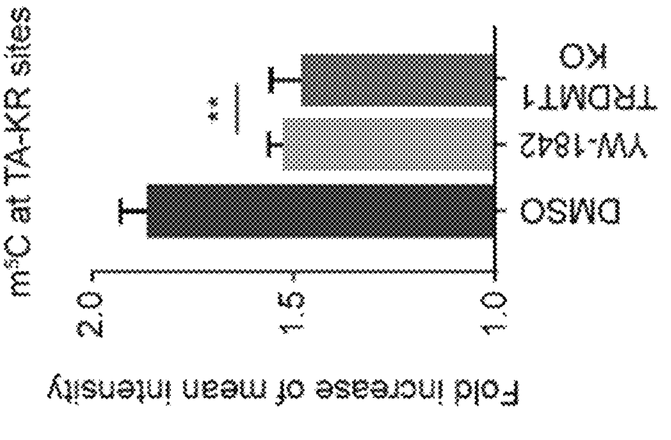
FIGS. 6A-6E show TRDMT1 Inhibitors specifically sensitizes cells to DNA damage agents.
Figure 6B:
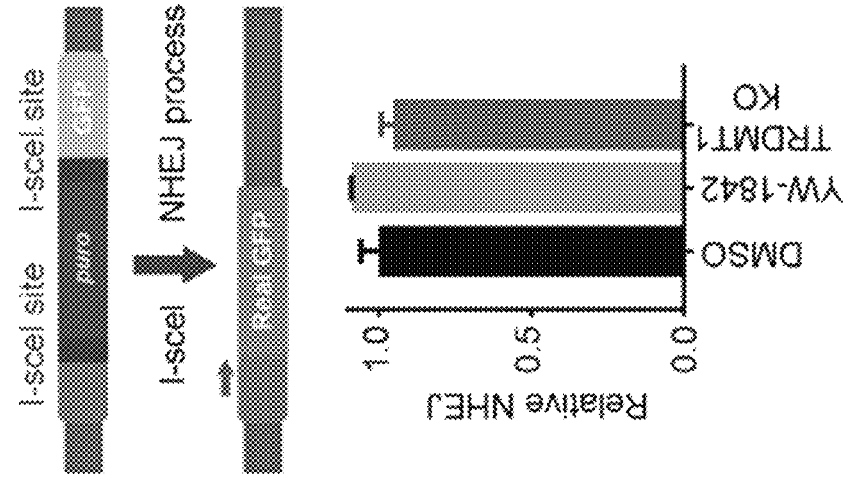
Figure 6C:
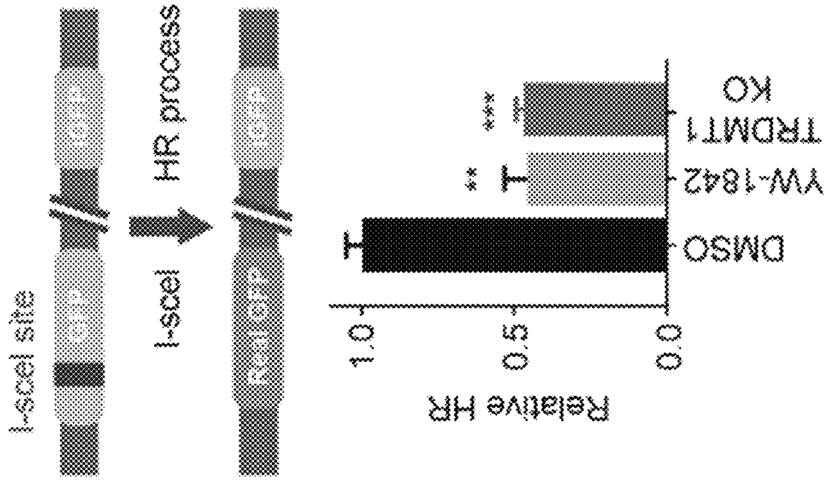
Figure 6D:
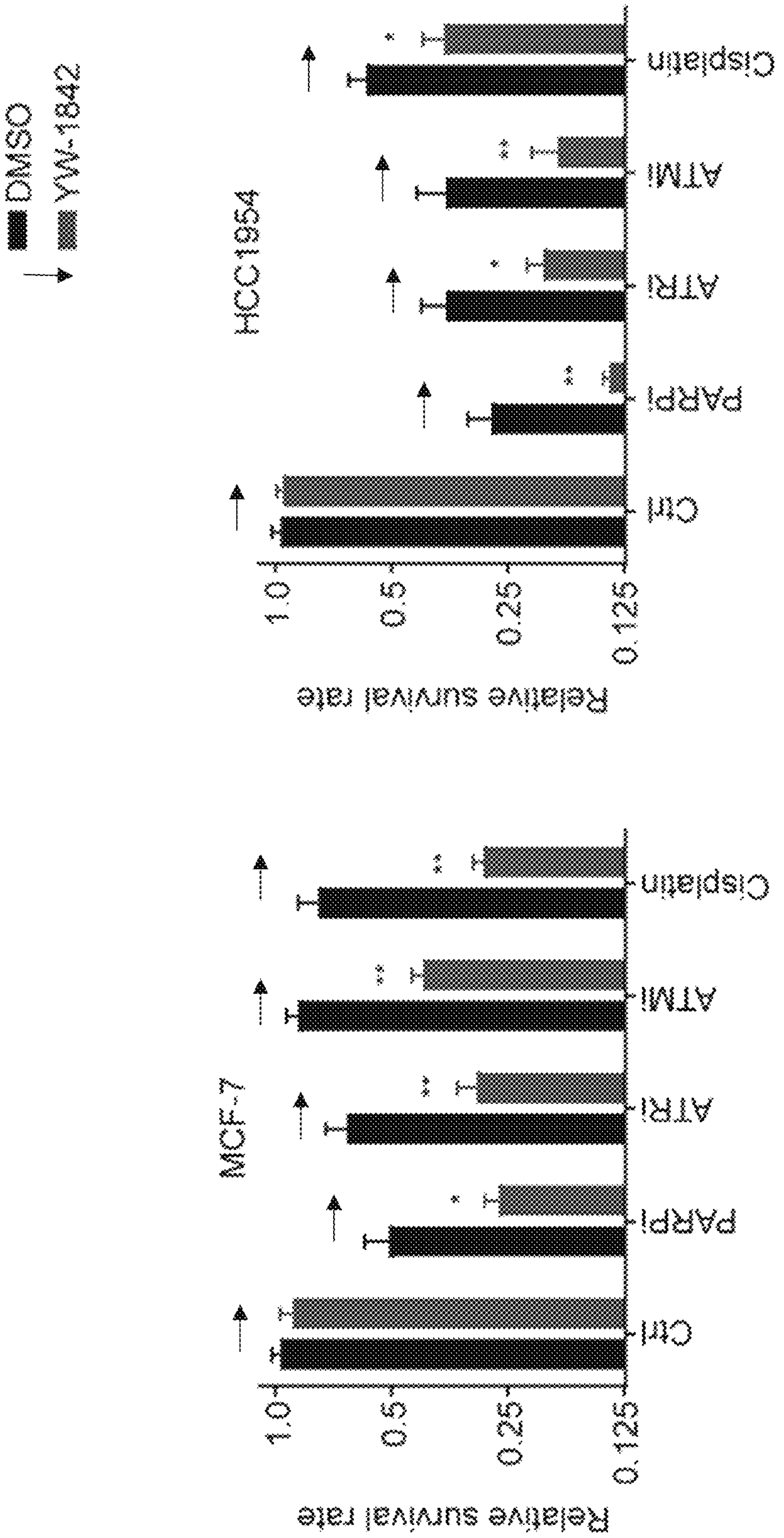
Figure 6E:
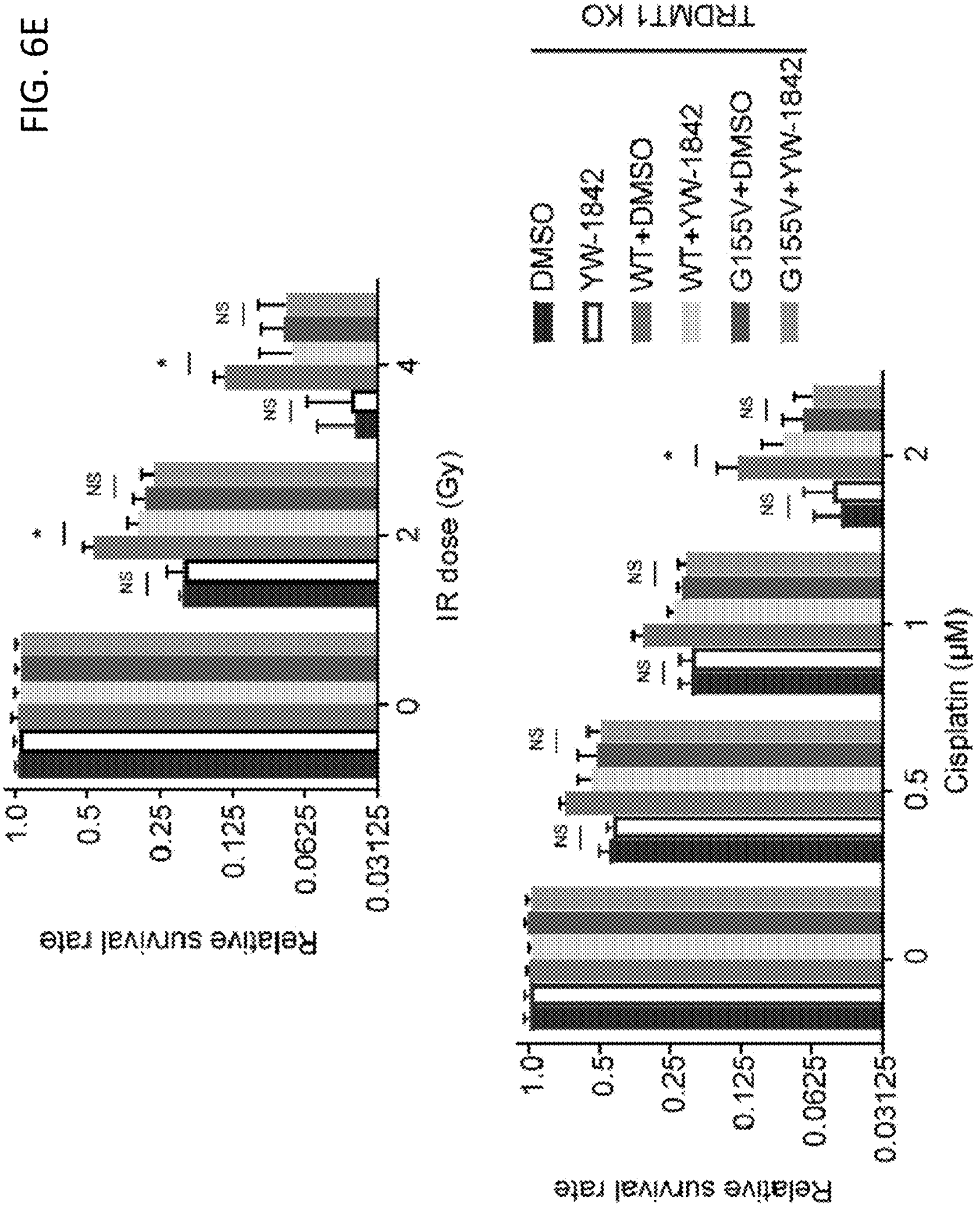
Figure 6F:
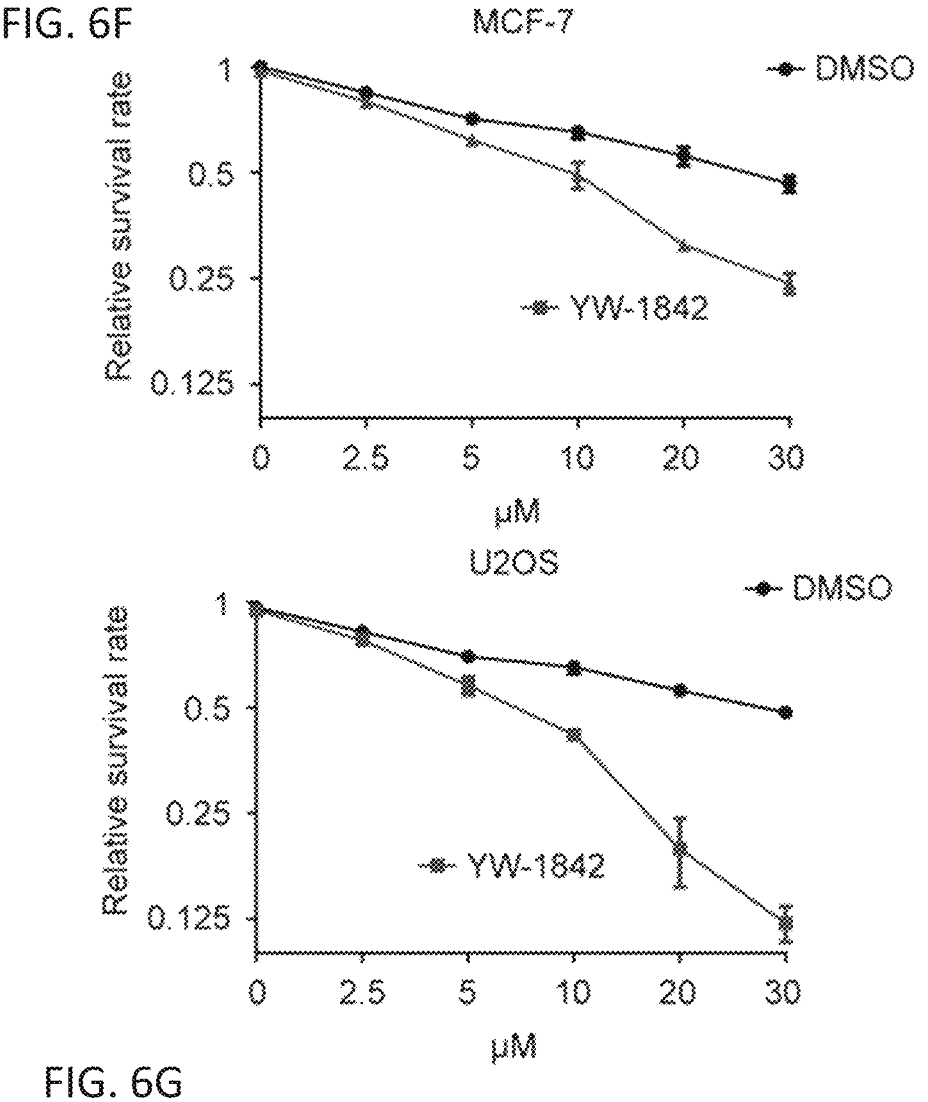
FIGS. 6F-6G show TRDMT1 inhibitor YW-1842 delays the repair of DSBs at the transcribed genome.
Figure 6G:
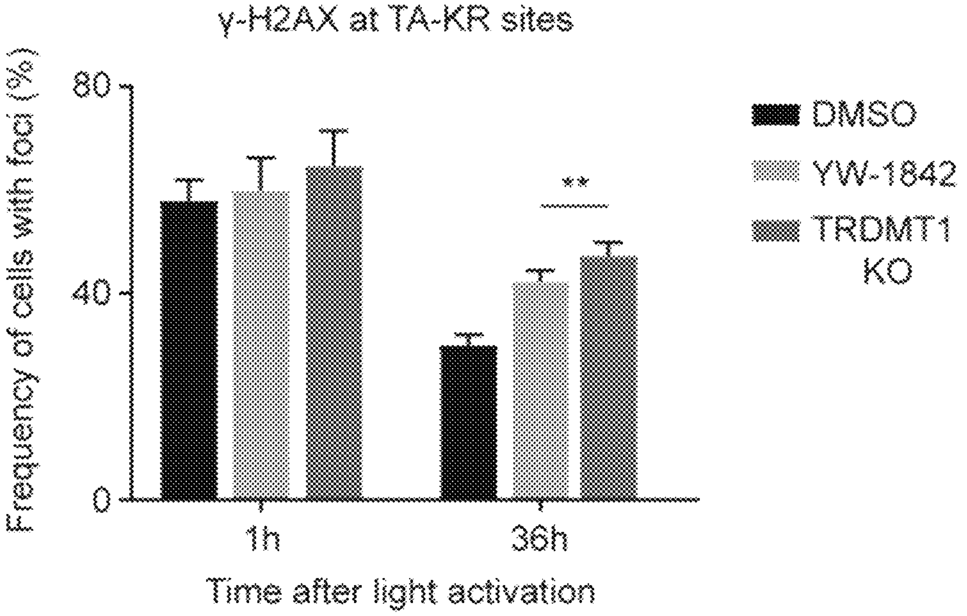
Figure 6H:
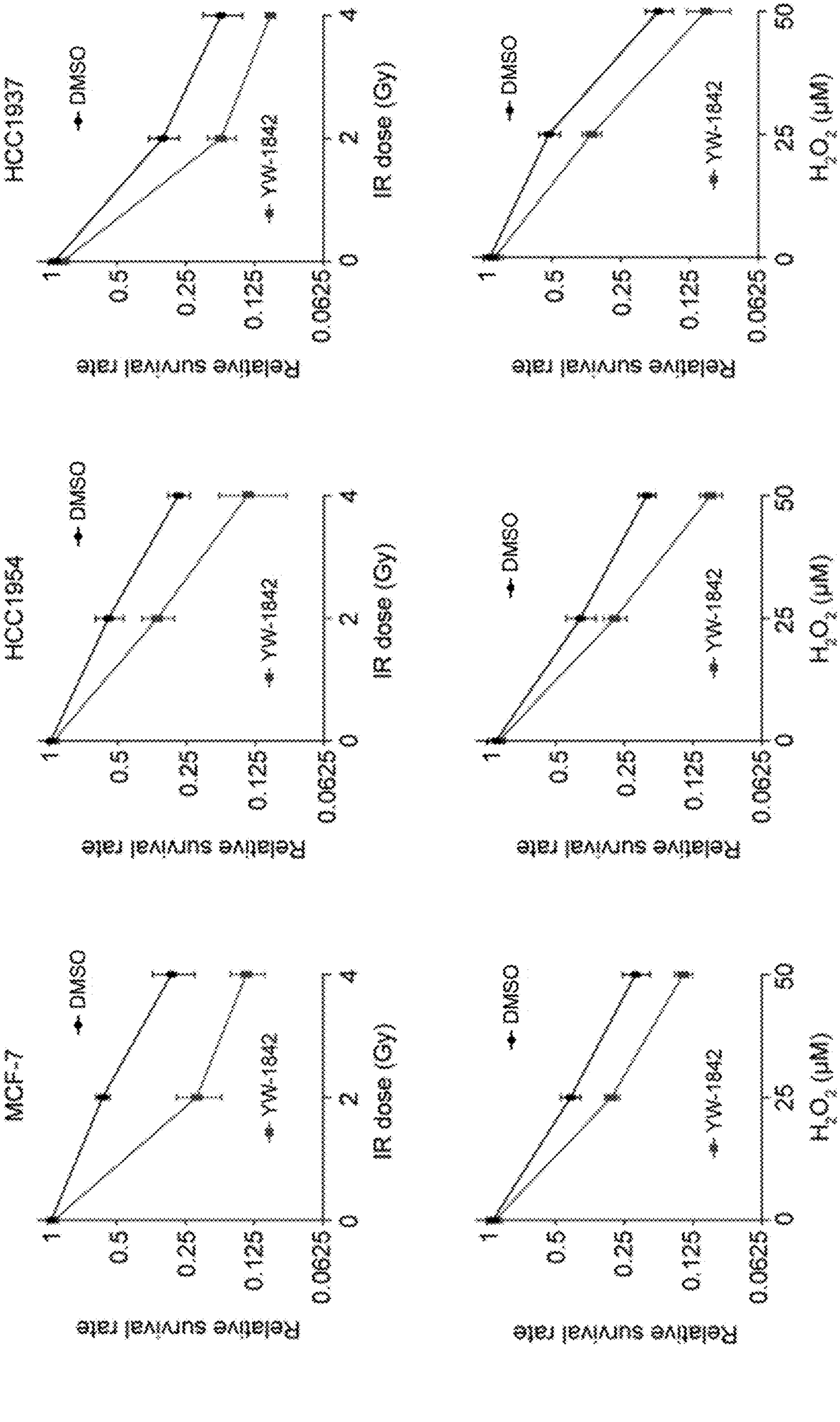
FIG. 6H shows TRDMT1 inhibitor YW-1842 sensitizes tumor cells to IR and $H_2O_2$. MCF-7, HCC1954, and HCC1937 cells were pre-treated with or without TRDMT1 inhibitor YW-1842 (2.5 μM) for 6 hrs, then the cells were exposed to IR or $H_2O_2$, and cultured for 7-14 days. The survival rate of these cells was analyzed (n=3, Mean±SD)

Under normal conditions, TRDMT1 transfers the methyl group from SAM to the fifth carbon atom of cytosine on RNA to produce $m^5C$ and SAM was converted to SAH[4]. Our current findings as described above suggested TRDMT1 is a promising target for cancer therapy based on its role in DNA repair. To identify a small molecule TRDMT1 inhibitor, an in-house compound library was screened, and a promising hit was discovered. Subsequent SAR optimization led to the identification of compound YW-1842, which exhibited-$m^5C$ inhibitory activity almost equivalent to TRDMT1 depletion at the contration of 2.5 μM/L (FIG. 6A). To rule out the possibility that YW-1842 is a cytotoxic drug, the antiproliferative effect of YW-1842 was measured and the compound did not prohibit cell proliferation at the concentration below 5 μM/L (FIG. 6H). DNA repair efficiency was also decreased with the compound as evidenced by a delayed clearance of γ-H2AX foci in cells after IR (FIG. 6I) with 2.5 μM/L YW-1842. Next, we used reporter assays to confirm the effects of YW-1842 on the HR-mediated repair of nuclease-generated DSBs at transcribed loci. Using the DR-GFP assay, we confirmed that YW-1842 diminished the repair of I-SceI-generated DSBs in comparison with DMSO treated group as well as siTRDMT1 (FIG. 6B). However, non-homologous end joining (NHEJ) showed no obvious changes in either TRDMT1 KD cells or the TRDMT1 wild type cells treated by compound YW-1842 (FIG. 6E). This observation is in line with our previous findings that TRDMT1 loss would not affect the efficiency of NHEJ. These data implicates YW-1842 is a potent inhibitor for TRDMT1.

Compound YW-1842 Sensitizes Tumor Cells to DNA Damage in a TRDMT1-Dependent Manner TRDMT1 plays a pivotal role in DNA repair by the HR pathway. Therefore, the inhibition of TRDMT1 activity may augment the cytotoxic effects of radiation and the DNA damaging agents, e.g. $H_2O_2$; Cisplatin; ATR inhibitor (ATRi) AZ20; ATMi KU55933; PARPi Olaparib. These DNA damaging agents cause comprehensive lesions, while DSBs accumulated by these agents are lethal to cells and could be repaired by the HR pathway. Importantly, Compound YW-1842 at 2.5 μM/L, which does not kill cells alone (FIG. 6I), sensitizes the cells to above DNA damaging agents compared to single treatment (FIG. 6D). Especially, YW-1842 at 2.5 μM demonstrated a strong synergy with a marketed drug PARPi Olaparib at 1 in a triple-negative breast cancer HCC 1954 cell lines (FIG. 6D). Moreover, when YW-1842 was combined with IR, a clear sensitivity enhancement for IR was exhibited (FIG. 6H). The combination of YW-1842 with $H_2O_2$ also decreased the survival rate of all the three cell lines compared to DMSO (FIG. 6H). Lastly, we tested the effect of YW-1842 after damage in TRDMT1 KO cells expressing TRDMT1$^{WT}$ or TRDMT1$^{G155V}$. Compound YW-1842 does not sensitize TRDMT1 KO, while TRDMT1$^{WT}$ expression rescued the sensitivity of TRDMT1 KO cells to either IR or Cisplatin, indicating that the effect of YW-1842 is dependent on TRDMT1 expression (FIG. 6D). Consistently, TRDMT1$^{G155V}$ expression did not rescue the sensitivity of TRDMT1 KO cells to either IR or Cisplatin, supporting our findings that the depletion of TRDMT1 due to TRDMT1$^{G155V}$-induced hyper ubiquitination renders the drug sensitivity in the patient (FIG. 6D). These findings strengthen the notion that concurrent modulation of TRDMT1 may be a therapeutically effective adjunctive treatment with chemotherapy or radiotherapy for patients who harbor TRDMT1-upregulated tumors.

Discussion

These Examples demonstrate the loss of TRDMT1 expression in cancer could lead to increased sensitivity of cancer cells to chemotherapy and/or radiotherapy due to inefficient DNA repair. The markedly reduced overall $m^5C$ methylation level in RNA and changes to the cancer cell physiology in TRDMT1 KO cells could be rescued by stable expression of TRDMT1$^{WT}$ but not the patient-derived mutant TRDMT1$^{G155V}$. This phenomenon was likely due to the loss of TRDMT1 via hyper-ubiquitination. When DNA damage is induced in the transcribed region, R loops are efficiently induced. Our previous study indicates that the DNA:RNA hybrids around SSBs and DSBs may recruit TRDMT1 and serve as its substrate. Once modified with $m^5C$, the DNA:RNA hybrids recruit RAD52 and RAD51 more efficiently for protecting the transcribed genome from damage. The E3 ligase TRIM28 is recruited by TRDMT1 and targets its lysine K251 for poly-ubiquitination, which is subsequently required for efficient repair progression. These Examples demonstrate that the amount of TRDMT1 at sites of DNA damage is tightly regulated in cells for efficient repair and cell survival.

TRDMT1 modifies tRNA in the cytoplasm; TRDMT1-dependent $m^5C$ sites has also been detected in mRNAs; biochemical fractionation experiments in *Drosophila* showed that TRDMT1 was mostly a cytoplasmic protein with a minor nuclear fraction tightly attached to the nuclear matrix; TRDMT1 was shown to exhibit nucleo-cytoplasmic shuttling in response to cellular stress. TRDMT1 carrying nuclear localization signal (NLS) localized to damage sites in the nucleus, and restored $m^5C$ formation and γ-H2AX clearance at the locus marked by TA-KR, supporting that the nuclear localization of TRDMT1 is important for DNA repair. In addition to RAD51, the repair of TA-KR-induced DSBs requires RAD52[14]. Here, we found TRDMT1$^{G155V}$ expression led to reduced mRNA $m^5C$ methylation and inefficient HR as evidenced by decreased recruitment of RAD51 and RAD52, and delayed disappearance of γ-H2AX foci at sites of DNA damage induced by TA-KR or IR compare to TRDMT1 WT transfection. In summary, G155V mutation significantly reduces the function of TRDMT1 in the face of DNA damage, which may weaken the function of TDRMT1 in DNA repair, further increase the instability of the genome, facilitating the lethality of chemotherapeutic drugs or radiation. Considering what we found, it is reasonable to speculate that TRDMT1 G155V variation may have therapeutic benefits for certain specific tumors, such as ovarian cancer.

Ubiquitination, a type of protein post-translational modification, plays an important role in protein degradation. Improperly ubiquitination may alter the particular protein level, and subsequently, impair the function of the protein. The E3 Ub ligases (E3s) mediate the final step of Ub transfer, which forms covalent bounds between the lysine residue of the substrate and the C-terminal carboxyl group of Ub. The E3s are critical since their strict control of both the efficiency and substrate specificity of the ubiquitination reaction. Here, we found the TRIM28 is the E3 ligase of TRDMT1. The TRIM28 not only mediates the ubiquitination of particular protein, but also mediates other biological processes, such as DNA damage repair, repression of transcriptional elongation, and cancer development. For ovary cancer, TRIM28 high expression was an independent predictor for ovarian cancer patients. It is also shown that TRIM28 plays a unique and essential role in transcriptional elongation. The Examples show that TRIM28 is specifically recruited to damage sites where TRDMT1 is enriched, indicating the unique role of TRIM28 in protecting the transcribed genome from damage. Either over-ubiquitination mutant G155V or loss of ubiquitination mutant K251R impairs cell survival to Cisplatin, suggesting that TRIM28-mediated TRDMT1 ubiquitination may largely contribute to tumor growth and drug resistance.

From an extensive drug discovery campaign, we identified a highly potent inhibitor YW-1842 that performed well in inhibiting TRDMT1 recruitment, $m^5C$ formation and HR efficiency at DNA damage sites, thus enhance the sensitivity of multiple DNA damage types. These findings further supported the notion that TRDMT1 inhibition-reduced RNA $m^5C$ methylation improved the efficacy of DNA damage-mediated therapeutic effects.

Importantly, TRDMT1 is upregulated in a subset of tumors and correlated with the poor prognosis of patients. Compound YW-1842 demonstrated high inhibitory activity. Taken together, our study demonstrated that TRDMT1 mediated DNA damage repair through mRNA $m^5C$ modification involving in the regulation of tumor therapy resistance, and made an important step toward the synthesis of potent, specific inhibitors for TRDMT1 for the treatment of patients suffering from cancer.

Material and Methods

Cell Culture and Transfection

U2OS, 293, MCF-7, SKOV3, HCC-1954, and HCC-1937 cells were cultured in DMEM with 10% (vol/vol) FBS in a controlled humidified atmosphere containing 5% $CO_2$ at 37° C. The U2OS-TRE cells used for the DART system were derived from the U2OS-263 cell line and the construction of U2OS TRDMT1 knockout (KO) cells has been described previously. Lipofectamine 2000 and Lipofectamine RNAiMax (Invitrogen) were used for plasmid and siRNA transfection, respectively, following a standard protocol. TRDMT1 siRNA was purchased from Invitrogen (siRNA ID: s4219, Cat #: 4392420). TRIM28 siRNA sequence is GCGGAAAUGUGAGCGUGUACACGCUCA-CAUUUCCG (SEQ ID NO: 1).

Plasmids

The TA-KR in pBroad3 plasmids were constructed as previously described[15]. The GFP spark-TRDMT1 was purchased from Sino biological (HG11224-ACG). The cDNAs of WT and mutated TRDMT1 (C79A, G155V, K251R, K122R, G155V/K251R) were then sub-cloned to the EGFP-C3 plasmid (Clontech), linked by EcoRI and BamHI for imaging experiments. Primers are shown in Table 2. The construction of NLS-GFP-RAD52 and NLS-I-SceI plasmids have been described previously[31].

TABLE 2

| Sequences of PCR Primers. | |
|---|---|
| Primer | Sequence |
| TRDMT1-F-EcoRI | CCGGAATTCTGATGGAGCCCCTGCGGGTG (SEQ ID NO: 2) |
| TRDMT1-R-BamH1 | CGCGGATCCTTATTCATATAAGATTTTGATTAG (SEQ ID NO: 3) |
| TRDMT1 K122R-F | CTTTTGGAAAATGTTAGAGGTTTTGAAGTATCT (SEQ ID NO: 4) |
| TRDMT1 K122R-R | AGATACTTCAAAACCTCTAACATTTTCCAAAAG (SEQ ID NO: 5) |
| TRDMT1 K251R-F | AGTGATCTCTCTGTGAGAATGCTAAAAGATTTT (SEQ ID NO: 6) |
| TRDMT1 K251R-R | AAAATCTTTTAGCATTCTCACAGAGAGATCACT (SEQ ID NO: 7) |
| TRDMT1 G155V-F | TTATCTCCAACCTCTCTTGTCATTCCAAATTCAAGGCTAC (SEQ ID NO: 8) |
| TRDMT1 G155V-R | GTAGCCTTGAATTTGGAATGACAAGAGAGGTTGGAGATAA (SEQ ID NO: 9) |

Cell Survival Assay

Approximately 500 U2OS/TRDMT1 KO U2OS/MCF-7/HCC1954/HCC1937 cells and TRDMT1 siRNA or GFP-TRDMT1 WT/G155V/K251R transfected cells were seeded in 6 cm dish with or without TRDMT1 inhibitors (2.5 μM/L). 6 hrs after seeding, cells were exposed to cisplatin (1134357, Sigma, 1 μM/L), ATMi (KU55933, C9867, Sigma, 1 μM/L), ATRi (AZ20, 57050, Selleck, 1 μM/L) or PARPi (Olaparib, AZD2461, Sigma, 1 μM/L) at indicated concentration or ionizing radiation (IR). After 7-14 days, colonies were fixed and stained with 0.3% crystal violet in methanol, and the number of colonies was counted manually.

Microscopy and Activation of KillerRed

The Olympus FV1000 confocal microscopy system (Cat. FIOPRDMYR-1, Olympus) and FV1000 software were used for the acquisition of images. Cells were cultured in 35 mm glass-bottom dishes (MatTek, P35GC-1.5-14-C) before observation. Activation of KR in bulky cells was completed by exposing cells to a 15 W Sylvania cool white fluorescent bulb for 25 min in a stage UVP (Uvland, CA). The intensity was measured by ImageJ 1.52i software.

Immunoprecipitation and LC/MS Analysis of GFP-TRDMT1

GFP-TRDMT1 stably expressed Flp-in 293 cells were treated with or without 2 mM $H_2O_2$ for 3 h before harvest as damaged and undamaged conditions. Wild-type 293 cells were used as control. The cell noodles were made in liquid nitrogen and then cryogenically milled into micron-sized particles to maximize the efficiency of solvent extraction of proteins. Two lysis buffer (20 mM HEPES, 0.5% TritonX-100 and protease inhibitors) with different salt concentrations (150 mM or 300 mM NaCl) were used to capture the protein interactions while preserving the extraction efficiency [Shi, Y. et al. A strategy for dissecting the architectures of native macromolecular assemblies. *Nat Methods* 12, 1135-8 (2015)]. Affinity purification of GFP-TRDMT1 from the whole cell lysates was carried out by an anti-GFP nanobody [Fridy, P. C. et al. A robust pipeline for rapid production of versatile nanobody repertoires. *Nat Methods* 11, 1253-60 (2014)] coupled to magnetic dynabeads (Thermo, Cat #14302D). After protein reduction and alkylation, the immunoprecipitation samples under each condition were run on a 4-12% SDS-PAGE gel using a short gradient. The whole region of each sample was cut and in-gel digested with trypsin as previously described [Algret, R. et al. Molecular architecture and function of the SEA complex, a modulator of the TORC1 pathway. *Mol Cell Proteomics* 13, 2855-70 (2014)]. After proteolysis, the peptide mixtures were desalted and analyzed with a nano-LC 1200 coupled to a Q Exactive™ Orbitrap™ mass spectrometer (Thermo Fisher). The peptides were loaded onto a picochip column (C18, 3 μm particle size, 300 Å pore size, 50 μm×10.5 cm; New Objective) and eluted using a 60 min LC gradient: 7% B-12% B, 0-3 min; 12% B—40% B, 3-50 min; 40% B-100% B, 50-53 min; 100% B, 53-60 min; mobile phase A consisted of 0.1% formic acid (FA) in LC/MS water, and mobile phase B consisted of 0.1% FA in 100% acetonitrile. The QE instrument was operated in the data-dependent mode, where the top 10 most abundant ions (mass range 350-1,500, charge state 2-6) were fragmented by high-energy collisional dissociation (normalized collision energy 30). The target resolution was 60,000 for MS and 7,500 for MS/MS analyses. The quadrupole isolation window was 2.0 Th and the maximum injection time for MS/MS was set at 100 ms. After MS analysis, the data was searched by Maxquant [Tyanova, S., Temu, T. & Cox, J. The MaxQuant computational platform for mass spectrometry-based shotgun proteomics. *Nat Protoc* 11, 2301-2319 (2016)] for identification and label-free quantification. The mass accuracy was specified as 10 and 20 p.p.m. for MS and MS/MS, respectively. Other search parameters included cysteine carbamidomethylation as a fixed modification and methionine oxidation as a variable modification. A maximum of three trypsin missed-cleavage sites was allowed.

For Western blot analysis, proteins from cells or tissues were separated by SDS-PAGE and then transferred to polyvinylidene difluoride membranes (PVDF; Bio-Rad, USA). The membranes were blocked with 5% non-fat milk in PBS and probed with antibodies against TRDMT1 (sc-365001, Santa Cruz Biotechnology, 1:400) TRIM28 (ab10484, Abcam, 1:1000), Ub (sc-8017, Santa Cruz Biotechnology, 1:500), Tubulin (12004165, Bio-Rad, 1:1000), β-Actin (8H10D10, Cell Signaling Technology, 1:10,000). After primary antibody incubation at 4° C. overnight and secondary antibody incubation at room temperature for 1 h, the membranes were washed 3 times in 0.1% PBST. Chemiluminescent HRP substrate was purchased from Millipore (Catalog #: WBKLS0500). Images were taken in the BIO-RAD Universal Hood II machine with corresponding Image-Lab software.

Dot Blot Assay

Total poly(A)+ mRNA from U2OS-TRE cells was purified with Dynabeads™ mRNA DIRECT™ Purification Kit (ThermoFisher Scientific, Catalog #: 61011). The amount of mRNA from different samples was diluted to the same concentration using 10 mM Tris-HCl from the kit. The mRNA solutions were loaded onto a positive-charged Nylon66 membrane (Biodyne B transfer membrane, 0.45 μm, 60209) and 1200 μJ was applied twice to the membrane in 1 min (UV Stratalinker 2400). After primary antibody (1:100) incubation at 4° C. overnight and secondary antibody (1:10,000) incubation at room temperature for 1 h, the membrane was washed 3 times in 0.02% PBST for 10 min each. The following steps were the same as in the western blot. The membrane was stained with 0.1% methylene blue (SIGMA-ALDRICH, Catalog #: M9140-25G) in 0.5 M sodium acetate.

Immunoassays and $m^5C$ Staining

Cells for immunofluorescence observation were fixed in 4% PFA (Affymetrix, 19943 1 LT) at room temperature for 15 min and further treated with 0.2% triton for 10 min. They were then blocked by 3% BSA (SIGMA, A-7030) at room temperature for 1 h. Primary antibody for RAD51(ab63801, Abcam, 1:200)), RAD52(sc-365341, Santa Cruz, CA, USA, 1:500), TRIM28 (ab10484, Abcam, 1:500), γH2AX ser139 (JBW301, 05-636, EMD Millipore, 1:200), were incubated with cells at 4° C. overnight. After washing with 0.05% PBS-Tween (PBST), the cells were incubated with secondary antibody for 1 h at room temperature.

For $m^5C$ staining using the heat method, the cells or tissues were fixed and permeabilized in a 35 mm glass-bottom dish using a standard protocol, incubated in buffer (10 mM Tris-HCl, 2 mM EDTA, pH=9) and steamed on a 95° C. heating block for 20 min to expose the antigen. The dish was cooled, washed 3 times with PBS and blocked using 5% BSA in 0.1% PBST for 0.5 h at room temperature. Primary antibody for $m^5C$ (33D3, ab10805, Abcam) and secondary antibody were diluted in the same buffer (5% BSA in 0.1% PBST) and followed the standard IF protocol. This protocol is modified from the classic heat-induced antigen retrieval method for paraformaldehyde-fixed tissues using Tris-EDTA buffer.

Animal Assay

SKOV3 cells ($1.0\times10^6$) were transfected with LV-TRDMT1-RNAi (gcAGAAGA AATTCACAGGAAA, SEQ ID NO: 15) or LV-NC-RNAi and injected intraperitoneally into female nude mice which were then randomly divided into 4 groups (6 animals per condition).

When mice developed palpable tumors (about a week after injection), cDDP (5 mg/kg) or saline were then injected into the center of the xenograft tumors twice per week for 3 consecutive weeks. On day 28, mice were sacrificed, and tumors were harvested. Terminal deoxynucleotidyl transferase dUTP nick end labeling (TUNEL) (In situ cell death detection kit, Fluorescein, 11684795910, Roche, Basel, Switzerland) was used to assess tissue apoptosis according to the instructions. All animal experiments were approved by and conducted according to the guidelines established by the Institutional Animal Care and Use Committee at the University of Pittsburgh. With the approval of the University of Pittsburgh, serous ovarian cancer samples from patients with FIGO stage IIIC or IV (n=38) were collected from tissue banks. All patients were treated with the standard care of platinum-based therapy after surgery, and informed consent was obtained from all patients. PFS was calculated from the time of surgery to the time of progression or recurrence. Platinum resistance or platinum sensitivity was defined by relapse or progression within 6 months or 6 months after the last platinum-based chemotherapy, respectively. Clinical and pathological features are described in Table 3.

TABLE 3

Clinicopathological characteristics of EOC patients (n = 38)

| | | PFS > 6 (n = 24) | PFS < 6 (n = 14) |
|---|---|---|---|
| | Age(yrs) | 57.13 ± 8.65 | 56.86 ± 6.85 |
| Stage | IIIC | 19 | 12 |
| | IV | 5 | 2 |
| Grade | High | 2 | 1 |
| | Moderate | 14 | 9 |
| | Low | 8 | 4 |

Immunohistochemistry and Scoring

Tumors were fixed, embedded in paraffins and sectioned into 4 μm thickness. After deparaffinization and rehydration, sections were blocked and incubated with antibody against TRDMT1(sc-365001, Santa Cruz, CA, USA, 1:200), Ki-67 (sc-23900, Santa Cruz, 1:200), and then detected using the Dako Envision two-step method of immunohistochemistry (Carpinteria, CA, USA). All IHC staining was scored independently by 2 pathologists. We divided the positive staining results into 0-4 categories as following: 0: <5%; 1: 6-25%; 2: 26-50%; 3: 51-75%; and 4: >76% staining.

NHEJ and HR Assay

Using a previously described method[Lan, L. et al. The ACF1 complex is required for DNA double-strand break repair in human cells. *Mol Cell* 40, 976-87 (2010)], U2OS (DR-GFP) and U2OS (EJ5-GFP) cells were seeded into 6 well plates and treated with indicated siRNAs and inhibitors after 16-24 h of seeding. 1 μg of I-SceI vector was transfected into siRNA or inhibitors pretreated cells using Lipofectamine 2000 (Invitrogen). Cells were then harvested by trypsinization and washed with PBS 48 h after I-SCEI transfection. The GFP signal arising from the recombination (HR) or non-homologous end joining (NHEJ) events were measured by flow cytometry.

Statistical Analysis

The data were presented as mean±SD from at least 3 independent experiments. Comparisons between each group were calculated using Student's t-test, two-tailed Fisher's exact test method of summing small P-values, one-way and two-way analysis of variance and Bonferroni's multiple comparison test as appropriate. A value of $P<0.05$ was considered significant. GraphPad Prism version 7 was used for graphics (GraphPad Software, San Diego, CA, USA).

Example 18. SYCP2 Contributes to HR and DDR Drug Resistance

Figure 7A:
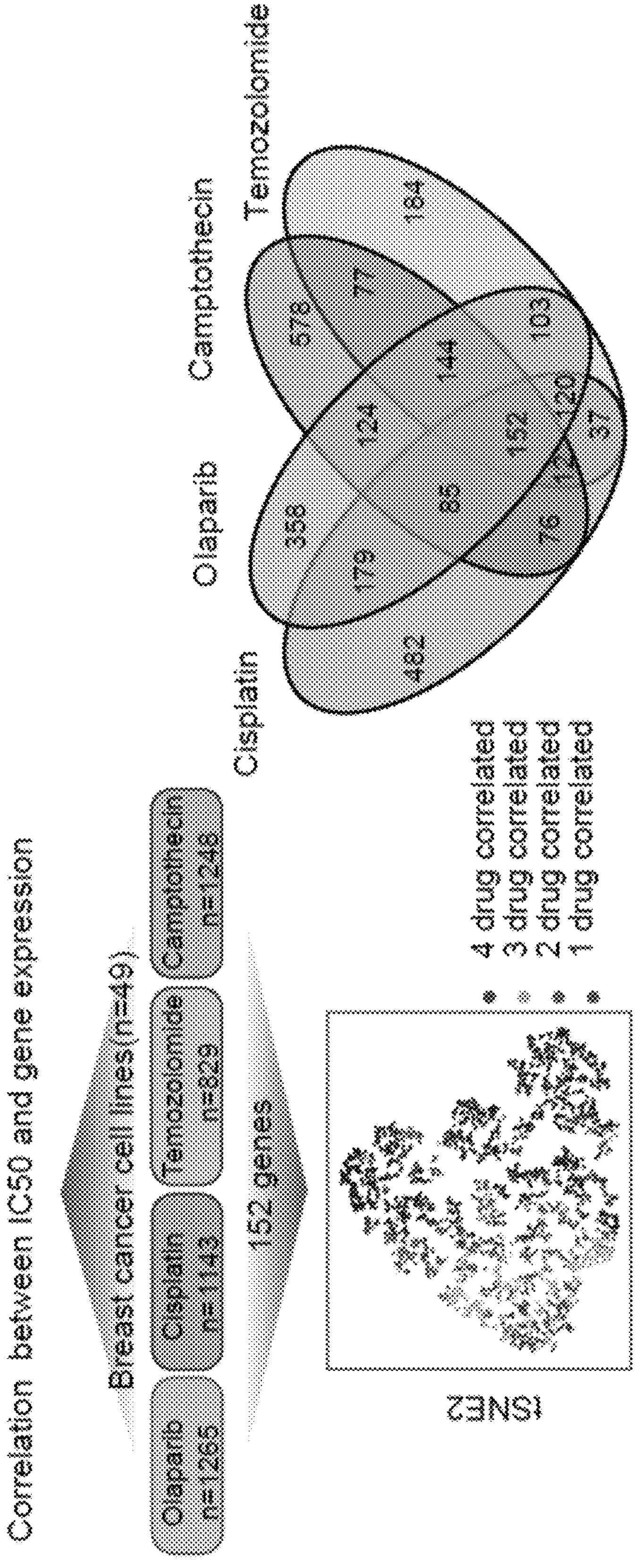
FIGS. 7A-7F show SYCP2 is the only synaptonemal complex protein ectopically expressed in breast cancer.
Figure 7B:
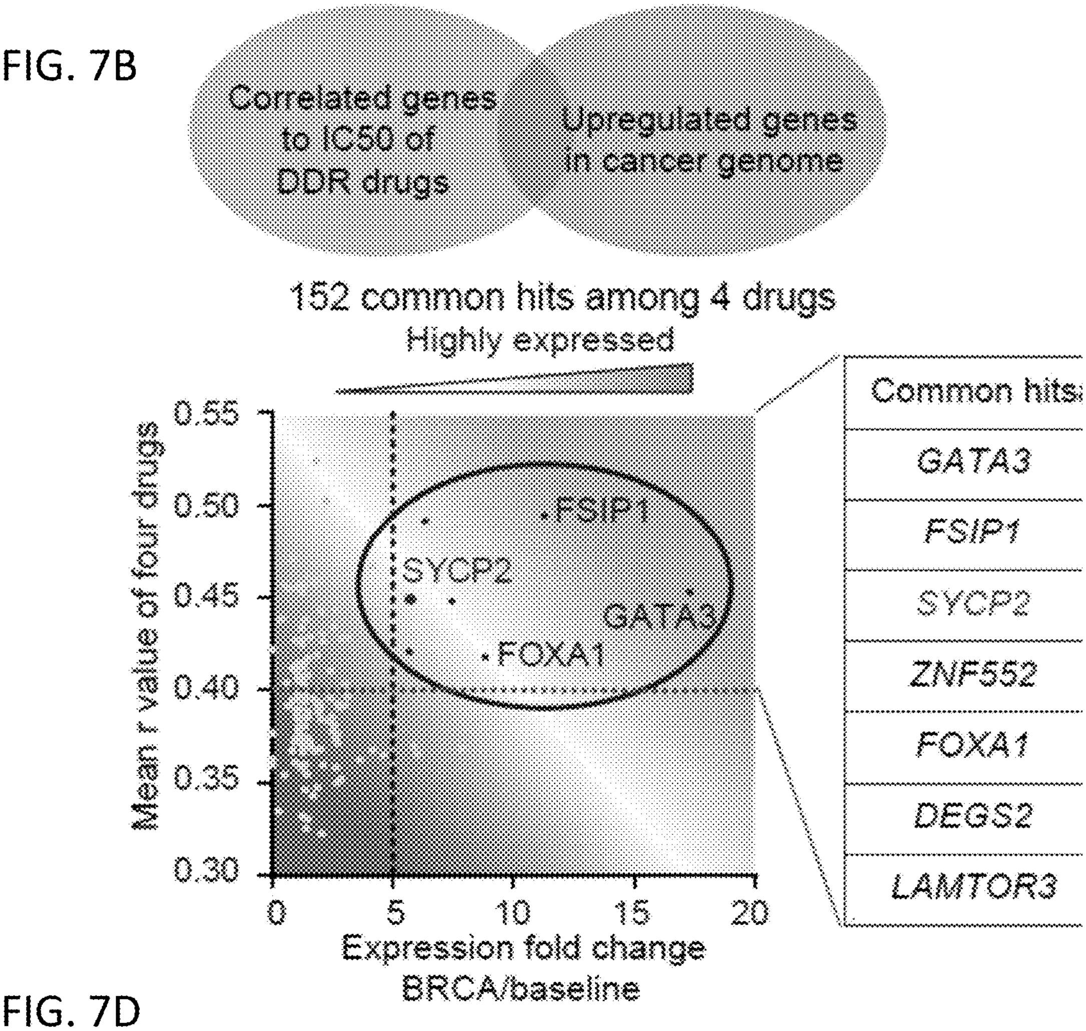
Figure 7D:
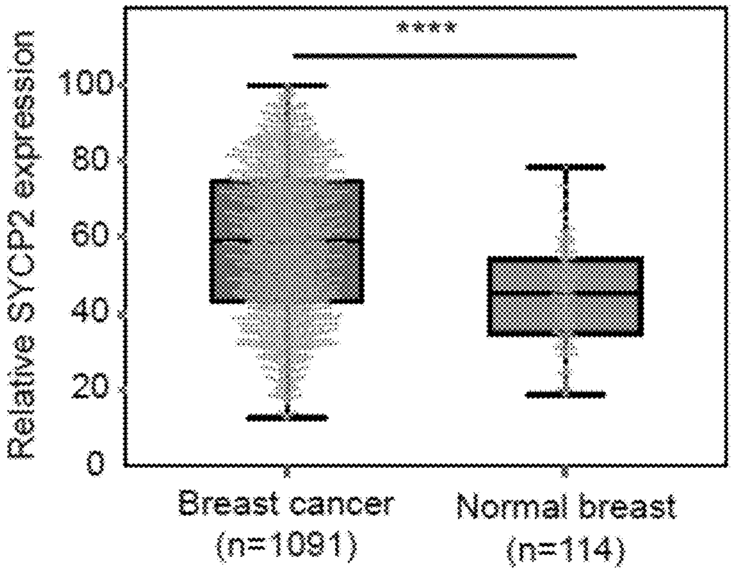
Figure 7C:
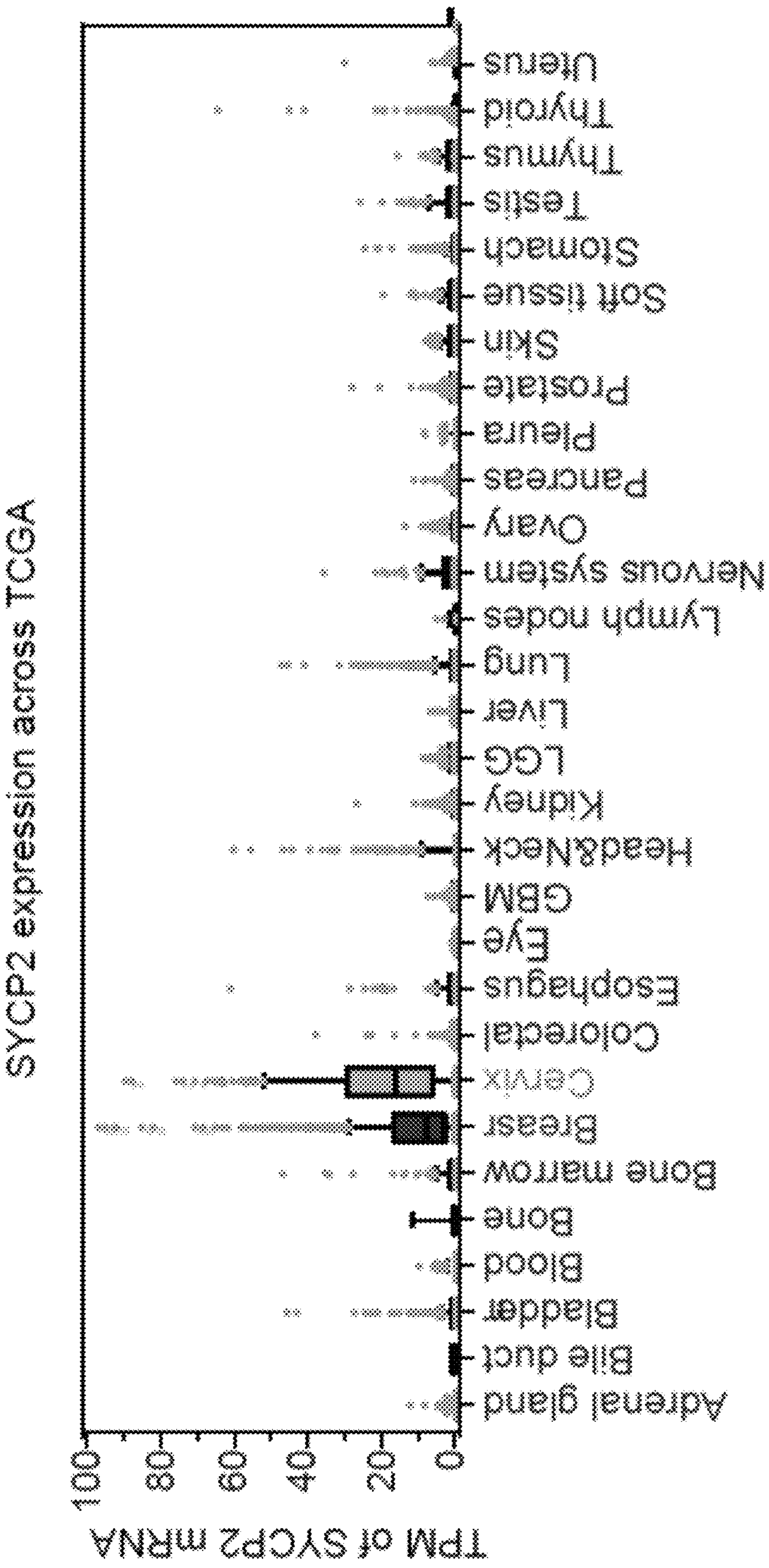
Figure 7E:
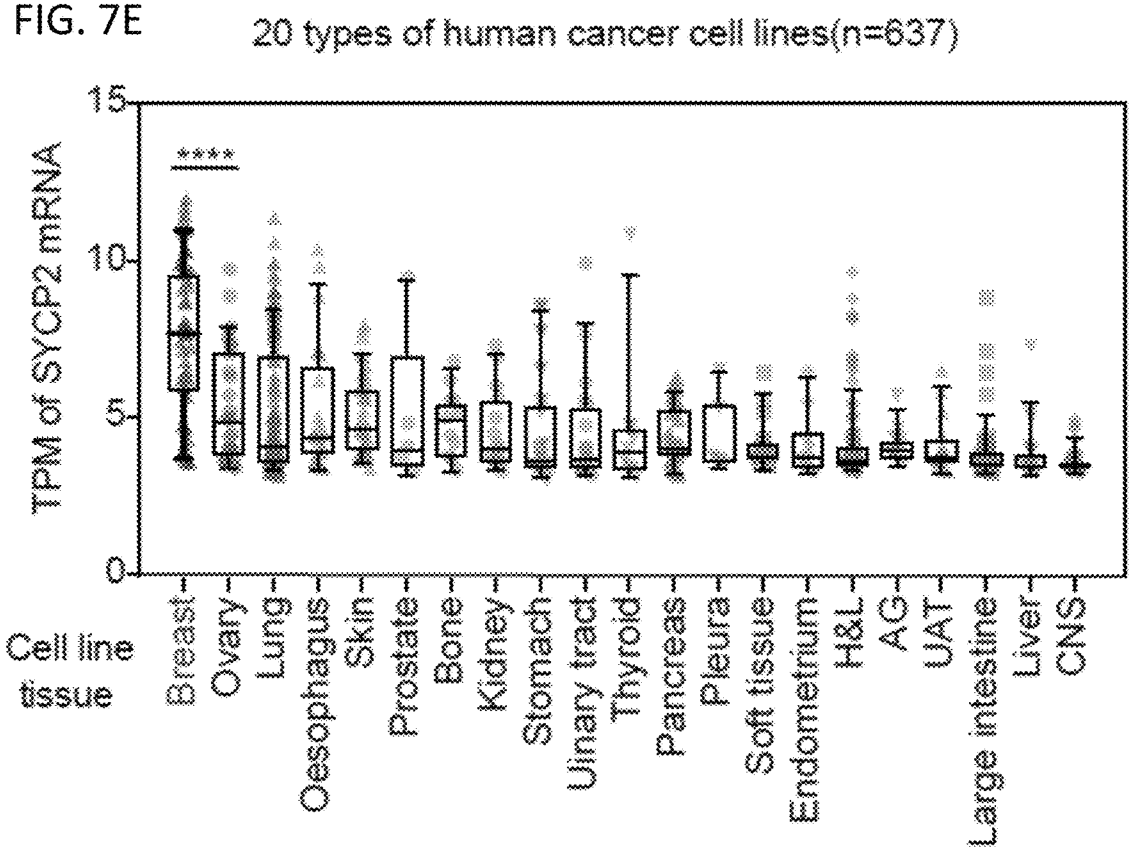

SYCP2 is the Only Synaptonemal Complex Protein Ectopically Expressed in Breast Cancer To identify genes whose up regulation is associated with the resistance of breast cancer to DDR-targeted drugs, we designed a multi-step bioinformatic pipeline to analyze gene expression in breast tumors and cell lines. First, we selected 49 breast cancer cell lines from the Cancer Cell Line Encyclopedia (CCLE) and Genomics of Drug Sensitivity in Cancer (GDSC) databases. These cell lines were selected because they have been characterized for both gene expression and sensitivities to four DDR-targeted drugs: olaparib, cisplatin, camptothecin, and temozolomide. Next, we preformed correlation analysis between the half-maximal inhibitory concentration (IC50) of each of the four drugs and the expression of genes in the 49 cell lines. About 1,000 genes were positively correlated with the IC50 of each drug. When we specifically looked for genes that correlated with the IC50s of all four drugs, only 152 genes were identified (FIG. 7A). Then, using the gene expression data from 1091 breast tumors in the TCGA database, we asked which of the 152 genes were overexpressed in breast tumors compared to normal breast tissues. Seven of the 152 genes were found to be more highly expressed in breast tumors than the rest of the genes (FIG. 7B). Among these 7 genes, FOXA1 and GATA3 have been shown to associate with chemoresistance in ER-positive breast cancers (Meyer and Carroll, 2012; Cowper-Sal•lari et al., 2012; Shahi et al., 2017). While DEGS2 and LAMTOR3 are highly expressed in breast tumors, they are also detected in tumors of other cancer types. Notably, SYCP2 is specifically overexpressed in breast and cervical cancers but not in 27 other cancer types in the TCGA database (FIG. 7C). Furthermore, SYCP2 expression is significantly higher in breast tumors than in adjacent breast tissues (FIG. 7D). Breast cancer is also the top cancer type for SYCP2 overexpression in CCLE and TARGET-treehouse databases (FIG. 7E). These results prompted us to further investigate whether SYCP2 is implicated in the resistance of breast cancer to DDR-targeted drugs.

Figure 7F:
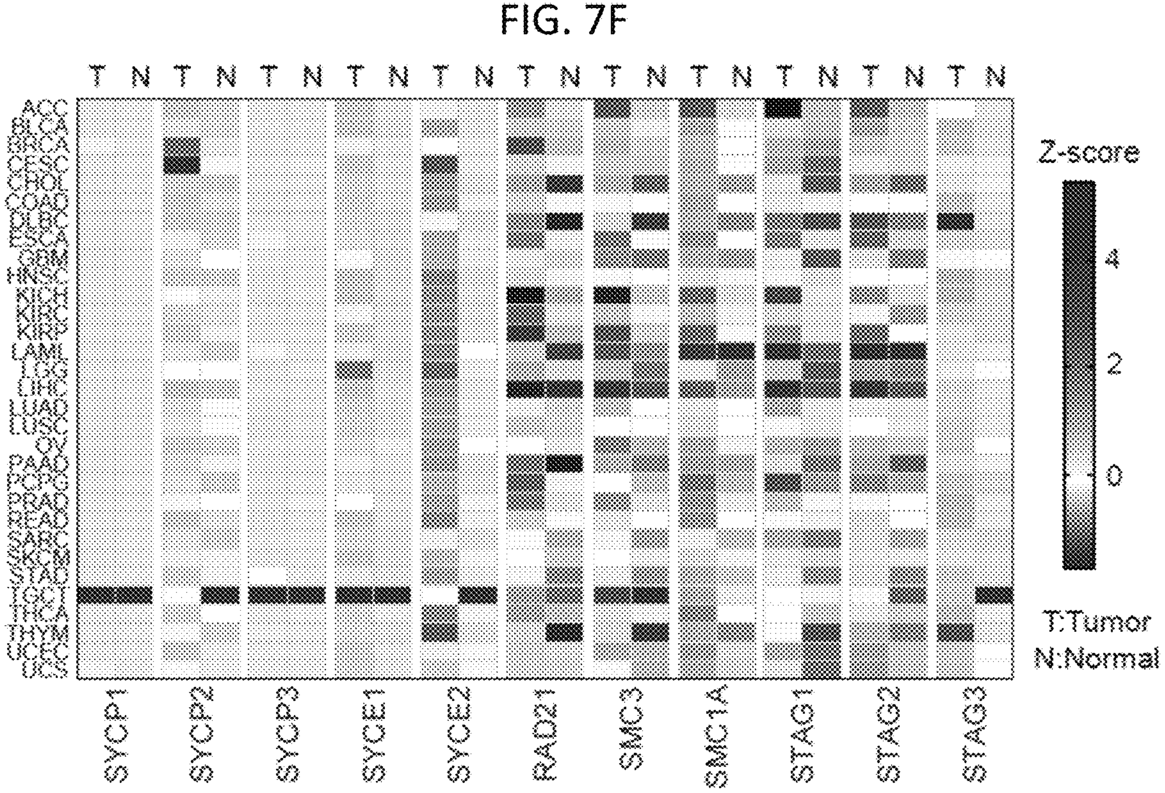

SYCP2 is a component of the synaptonemal complex (SYC), which also contains SYCP1, SYCP3, and SYCP2L. The SYC is important for paring homologous chromosomes and regulating cohesion in meiosis. We analyzed the mRNA levels of SYC and cohesin genes in 10,000 patient samples in the TCGA database. Consistent with their functions in meiosis, SYC genes are highly expressed in testis (FIG. 7F). However, only SYCP2, but not SYCP1, SYCP3, and SYCP2L, is ectopically expressed in breast tumors (FIG. 7F). A similar observation was made in the breast cancer cell lines in the CCLE database. On the other hand, cohesin proteins including RAD21, SMC1/3, and STAG1/2/3 are not up regulated in breast tumors (FIG. 7F). Thus, SYCP2 is the only SYC protein highly expressed in breast cancer, suggesting that SYCP2 may function independently of the SYC to promote resistance to DDR-targeted drugs.

Figure 8A:
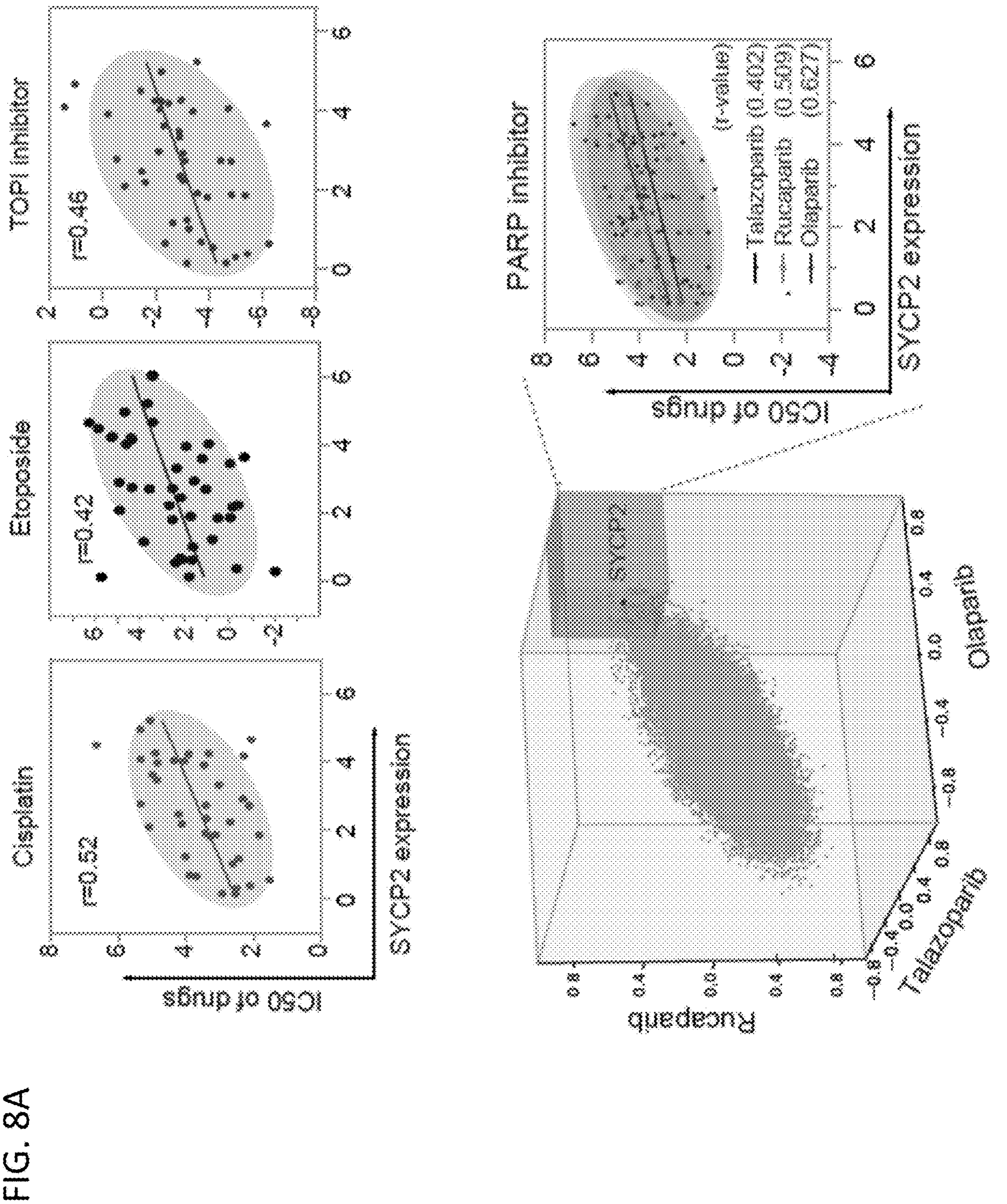
FIGS. 8A-8C show SYCP2 expression associates with resistance to DDR-targeted drugs.
Figure 8B:
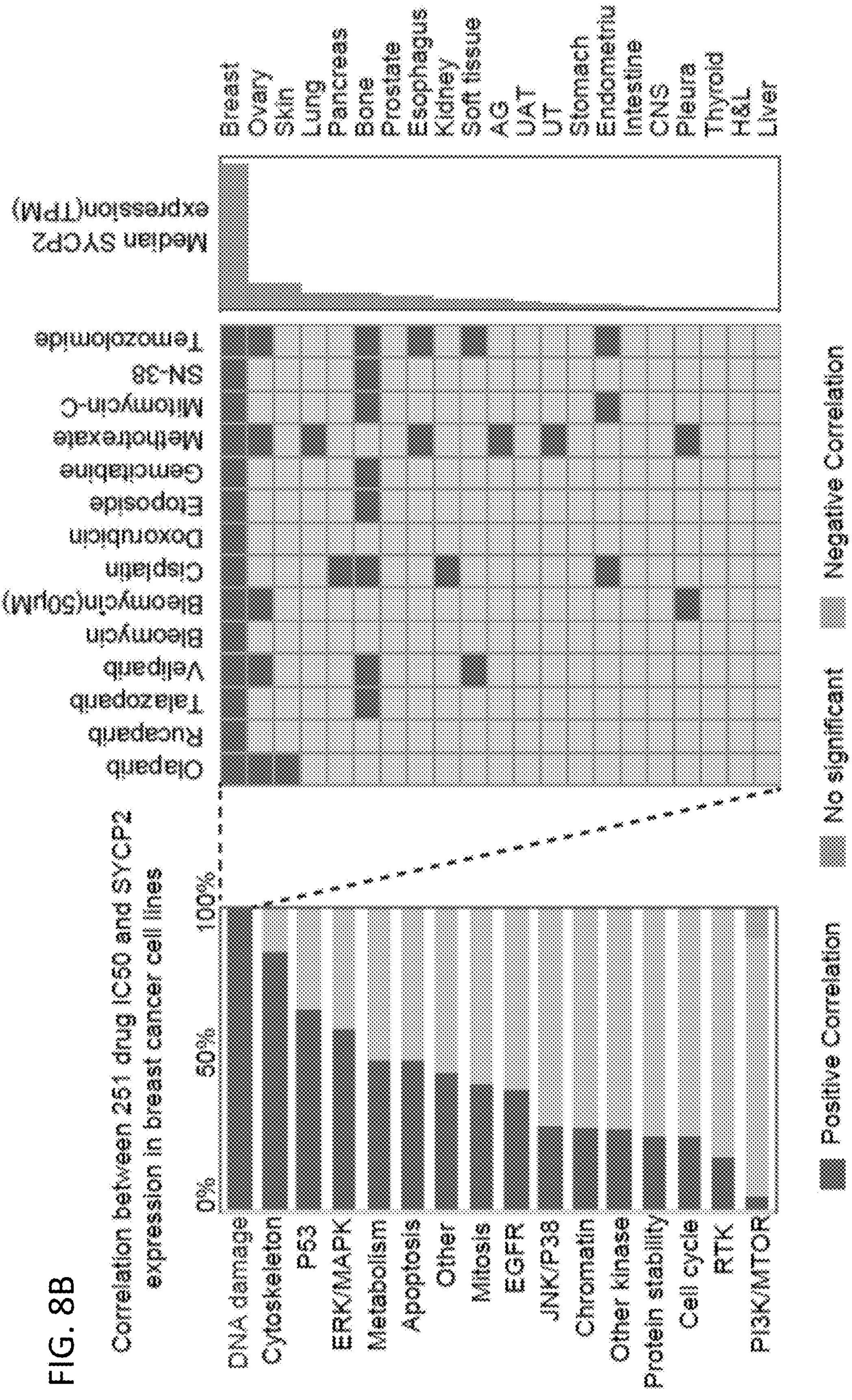

SYCP2 Expression Specifically Associates with Resistance to DDR-Targeted Drugs Next, we asked whether the high expression of SYCP2 associates with a general resistance to DDR-targeted drugs. In addition to the four DDR-targeted drugs used in our bioinformatic analysis, the expression levels of SYCP2 strongly correlate with IC50s of the Cisplatin, topoisomerase II inhibitor etoposide and topoisomerase I (TOPI) inhibitor (FIG. 8A). Furthermore, SYCP2 is one of top genes whose expression levels correlate with resistance to three distinct PARP inhibitors: olaparib, talazoparib, and rucaparib (FIG. 8A). The correlation coefficient r values for SYCP2 expression and IC50s of olaparib, talazoparib, and rucaparib are 0.627, 0.509, and 0.402, respectively (FIG. 8A). Expression of SLFN11 and DYNLL1 correlates with the sensitivity to PARPi. The results confirm the inverse correlations of SLFN11 and DNYLL1 with IC50s of the four PARPis. The p values for the inverse correlations of SLFN11 and DNYLL1 with IC50s of the PARPis are over 0.305 whereas the p values for the positive correlations of SYCP2 with IC50s of the PARPis are in the range of $1\times10^{-6}$-0.019, suggesting that SYCP2 is a better predictor of the PARPi response than SLFN11 or DNYLL1. We also analyzed the correlation between SYCP2 expression and IC50s of 14 DDR-targeted drugs in different cancer types. The correlation in breast cancer is by far the strongest (FIG. 8B). These results suggest that high SYCP2 expression in breast cancer broadly associates with resistance to a variety of DDR-targeted drugs.

Figure 8C:
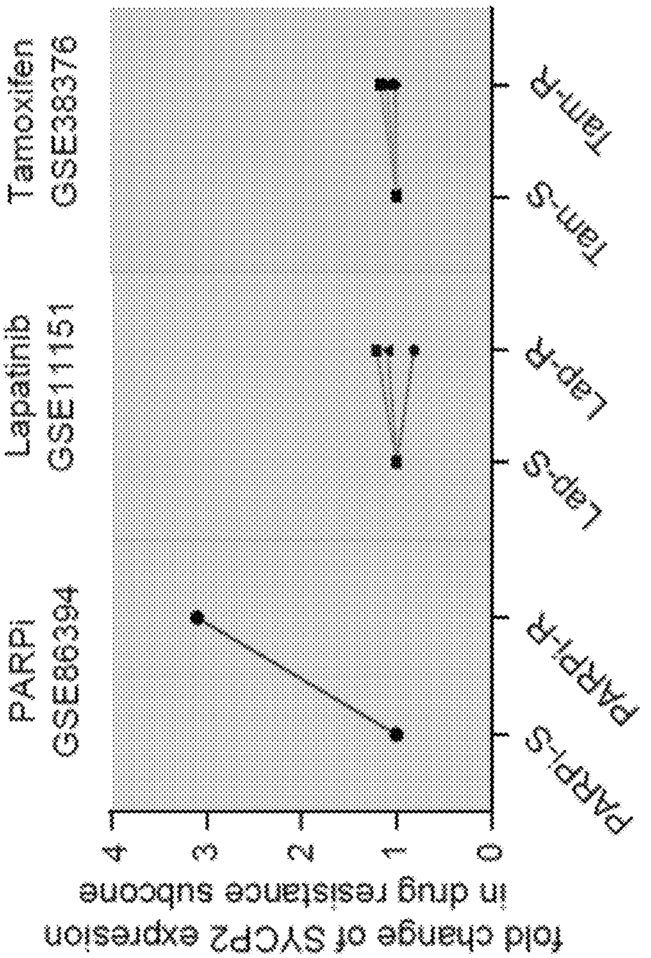

To understand whether SYCP2 expression also correlates with resistance to drugs in other pathways, we expanded the correlation analysis to 248 anticancer drugs targeting different cellular pathways. Among all the pathways targeted, the DDR pathway showed the strongest correlation with expression of SYCP2 (FIG. 8B). In contrast, drugs targeting PI3K kinase and histone modifying enzymes do not show consistent correlation. The correlation of SYCP2 expression with resistance to different drugs in isogenic cell line pairs was analyzed (FIG. 8C). SYCP2 is up regulated in PARPi-resistant cells, but not in cells resistant to lapatinib, a tyrosine kinase inhibitor, and tamoxifen, an estrogen receptor antagonist. Thus, SYCP2 expression specifically associates with resistance to DDR-targeted drugs but not drugs targeting other pathways.

SYCP2 is Required for Efficient Homologous Recombination

Figure 9A:
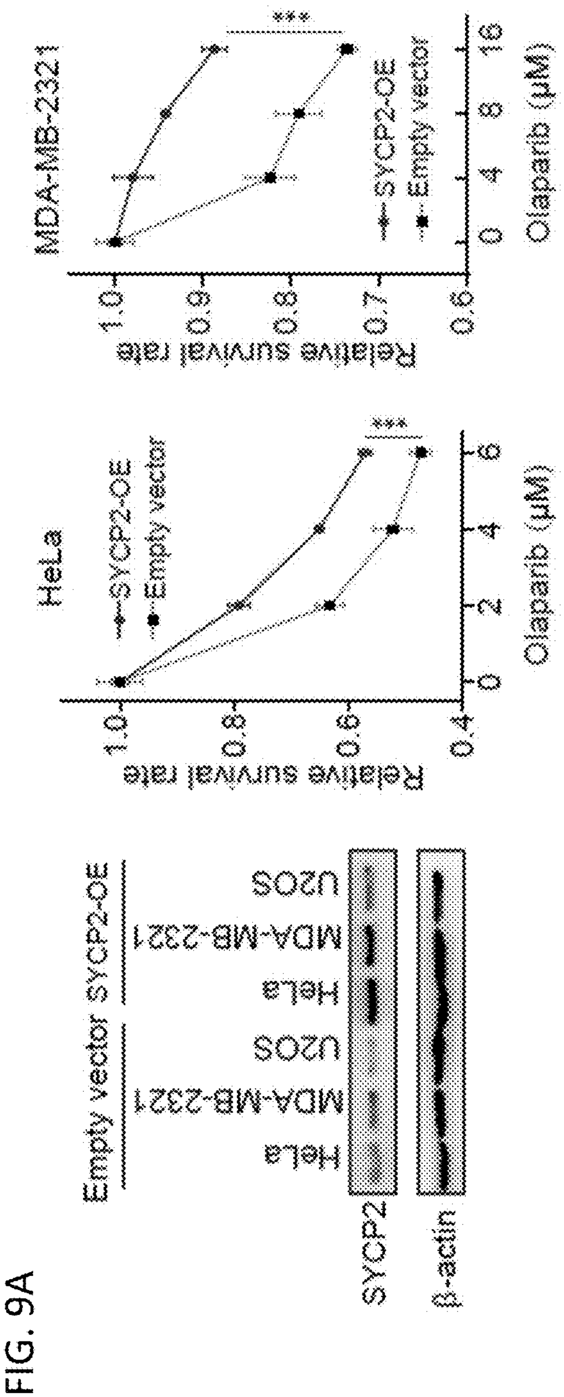
FIGS. 9A-9G show SYCP2 is required for efficient homologous recombination.
Figure 9B:
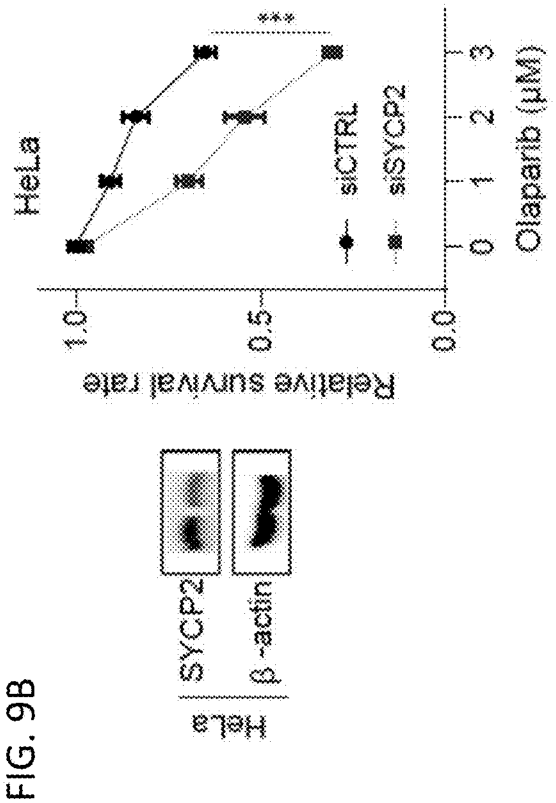
Figure 9C:
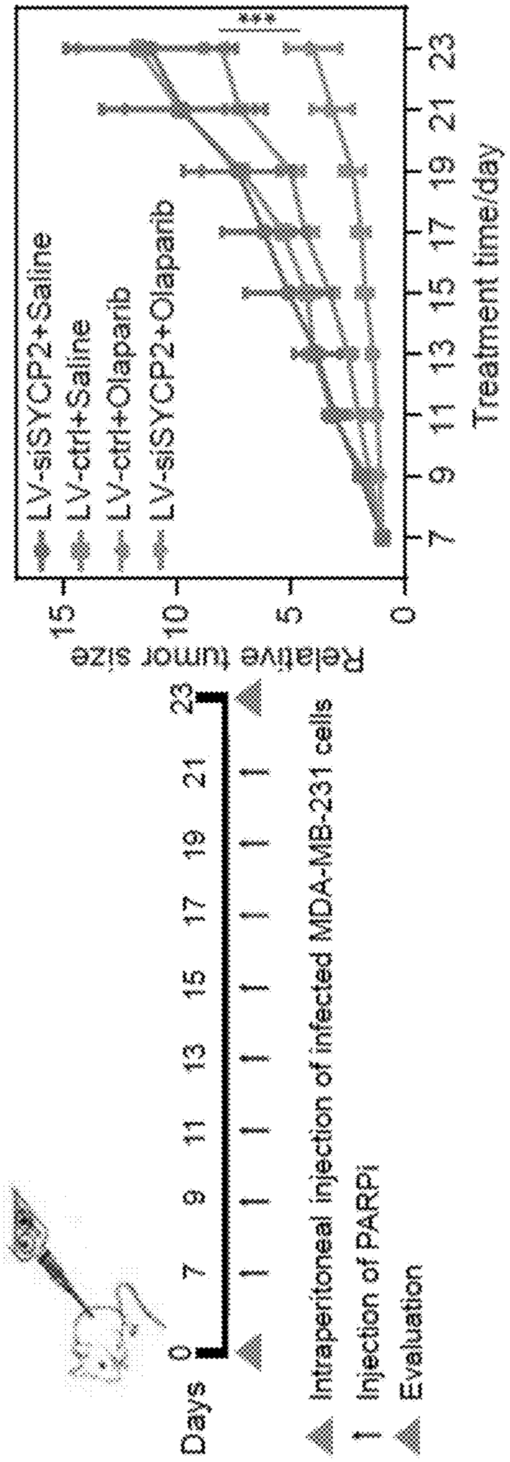

To further investigate whether and how SYCP2 contribute to DNA damage resistance, we overexpressed SYCP2 in the breast cancer cell line MDA-MB-231 and cervical cancer cell line HeLa. As shown in FIG. 9A, SYCP2 overexpression (SYCP2-OE) rendered MDA-MB-231 and HeLa cells resistant to PARPi (FIG. 9A). Conversely, knockdown of SYCP2 in HeLa cells increased the sensitivities to PARPi, cisplatin and ionizing radiation (IR) (FIG. 9B). To test the effects of SYCP2 in vivo, MD-MBA-231 cells infected with lentiviruses (LV) expressing siSYCP2 or siControl were injected intraperitoneally into mice, and tumor growth was measured over 23 days. As expected, PARPi reduced the growth of control tumors (FIG. 9C). Importantly, PARPi reduced the growth of SYCP2 knockout tumors more than control tumors (FIG. 9C), showing that SYCP2 depletion sensitizes cancer cells to PARPi in vivo. Together, these results demonstrate that the up or down regulation of SYCP2 is sufficient to alter the sensitivity of cells and tumors to DNA damage and DDR-targeted drugs.

Figure 9D:
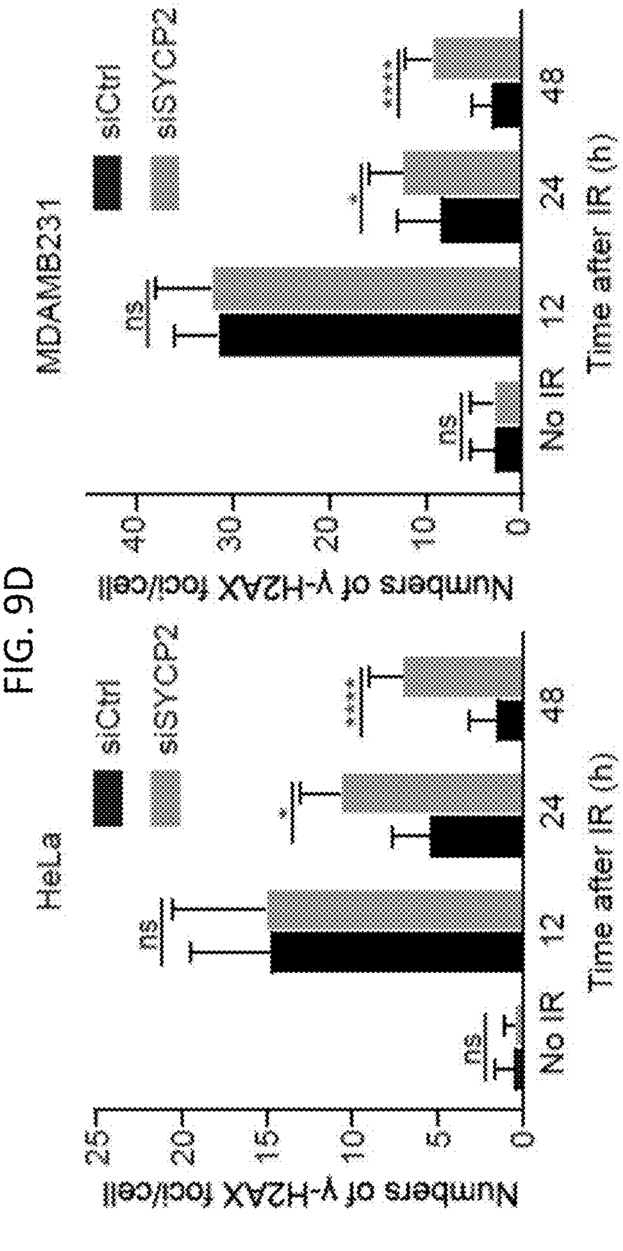
Figures 9E, 9F:
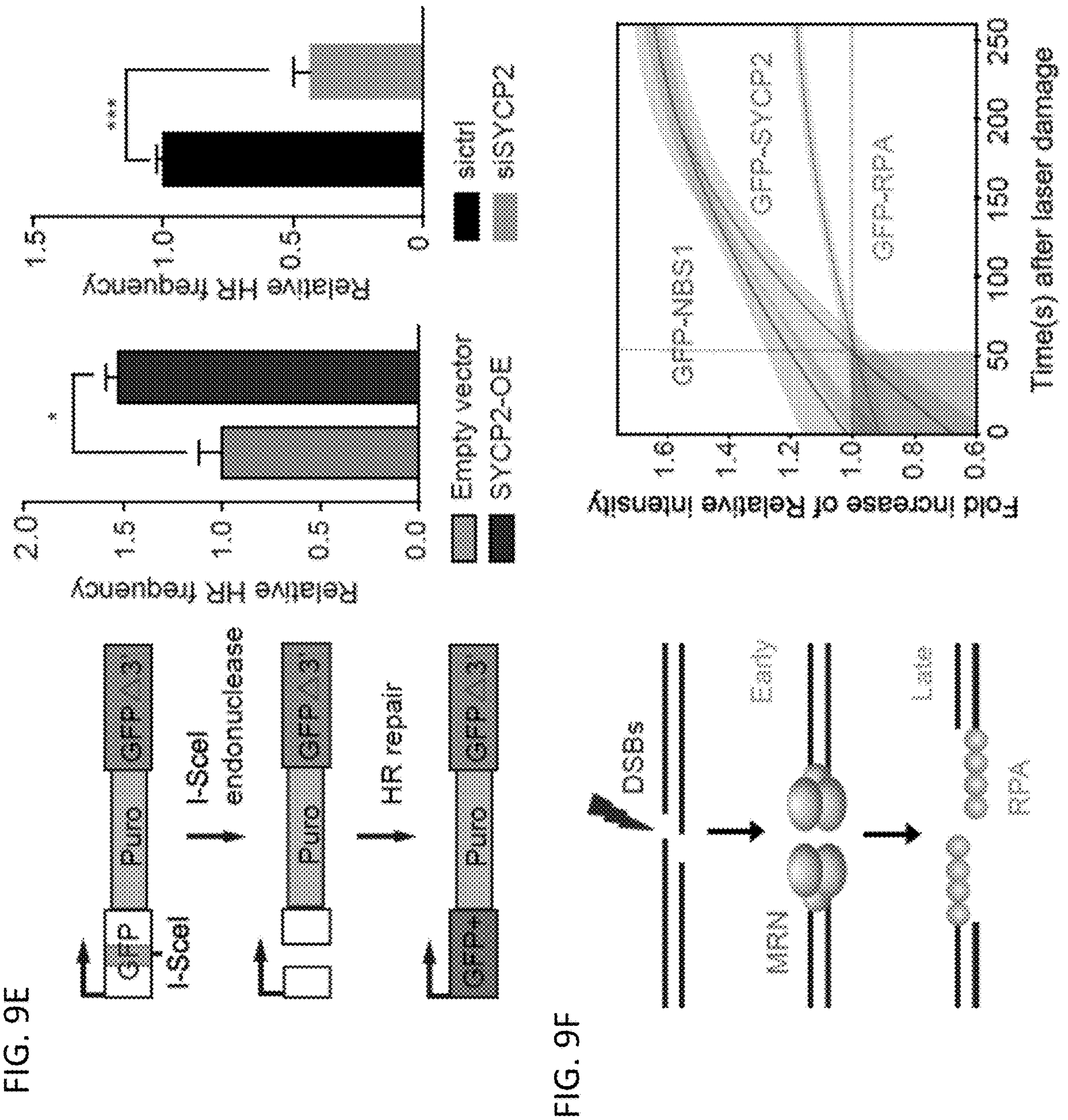

The role of SYCP2 in DNA damage resistance prompted us to test if it is involved in DNA repair. Knockdown of SYCP2 in MDA-MB-231 and HeLa cells delayed the clearance of 7-H2A.X, a marker of DSBs, after IR (FIG. 9D), suggesting that SYCP2 is required for efficient DSB repair. HR is one of the major repair pathways to remove DSBs, and HR deficiency is a well-known cause of PARPi sensitivity Using the DR-GFP reporter, in which a functional GFP gene is generated through HR-mediated repair, SYCP2 overexpression increased HR, whereas SYCP2 knockdown significantly decreased HR (FIG. 9E). These effects of SYCP2 on HR are not attributed to alterations of the cell cycle. Thus, SYCP2 may affect DNA damage sensitivity by directly regulating HR.

SYCP2 Promotes RAD51 Localization to DSBs Independent of BRCA1

Figure 9G:
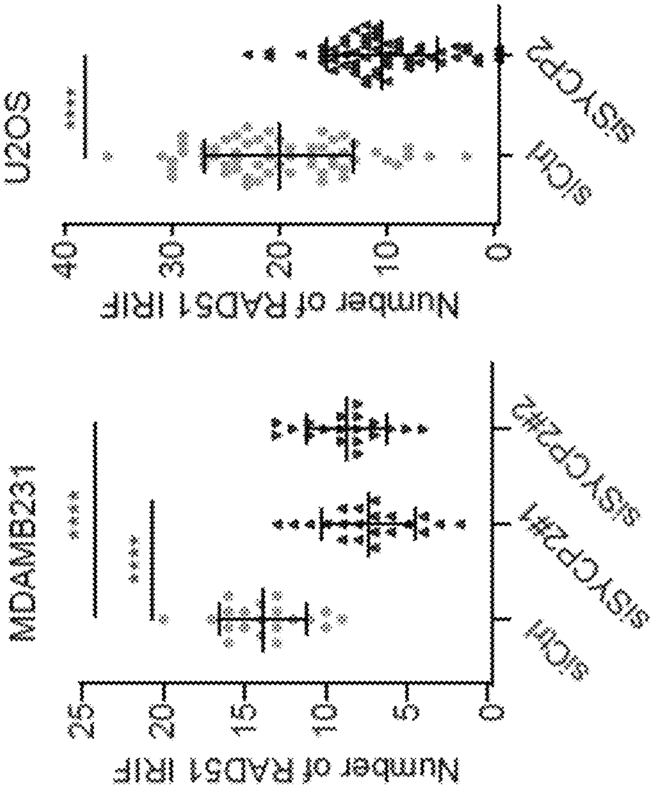

DNA end resection by the MRE11-RAD50-NBS1 complex is an early event in HR that generates ssDNA and recruits RPA to DSBs. SYCP2 was recruited to laser microirradiation-induced DSBs slightly after NB S1 but well before RPA (FIG. 9E), suggesting that SYCP2 is one of early responders to DSBs. SYCP2 also formed nuclear foci after IR. The localization of RAD51 to DSBs is a key HR event after DNA end resection. In both MDA-MB-231 and U2OS cells, knockdown of SYCP2 significantly decreased IR-induced RAD51 foci without affecting RAD51 expression (FIG. 9G). These results suggest that SYCP2 promotes HR by localizing RAD51 to DSBs.

Figure 10A:
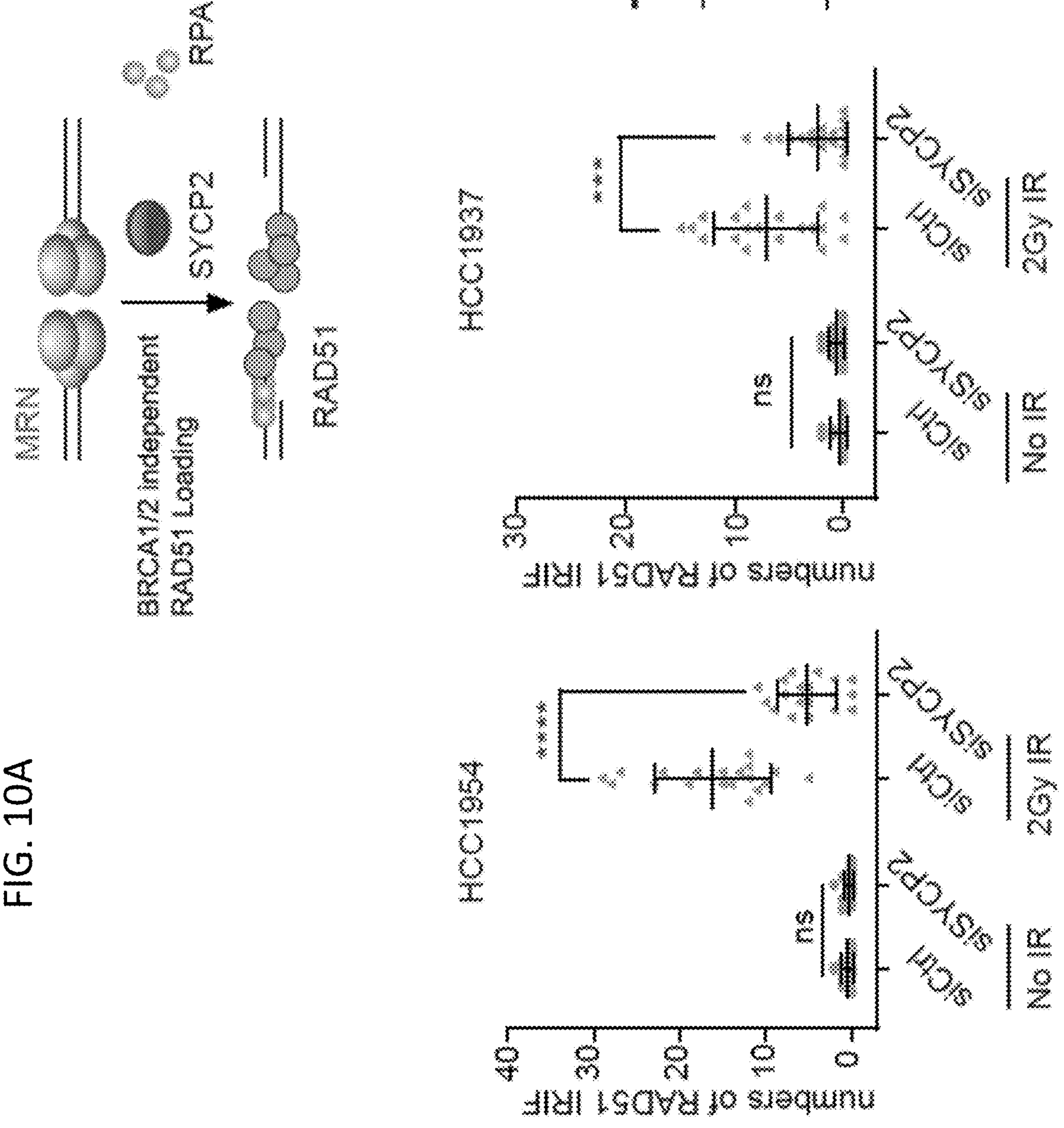
FIGS. 10A-10E show SYCP2 promotes RAD51 localization to DSBs independently of BRCA1.
Figure 10B:
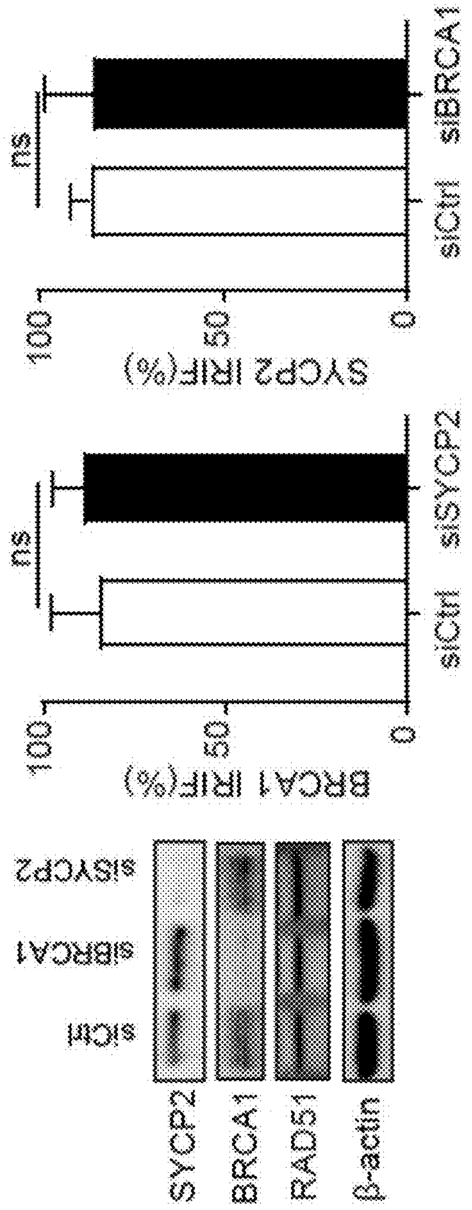
Figure 10C:
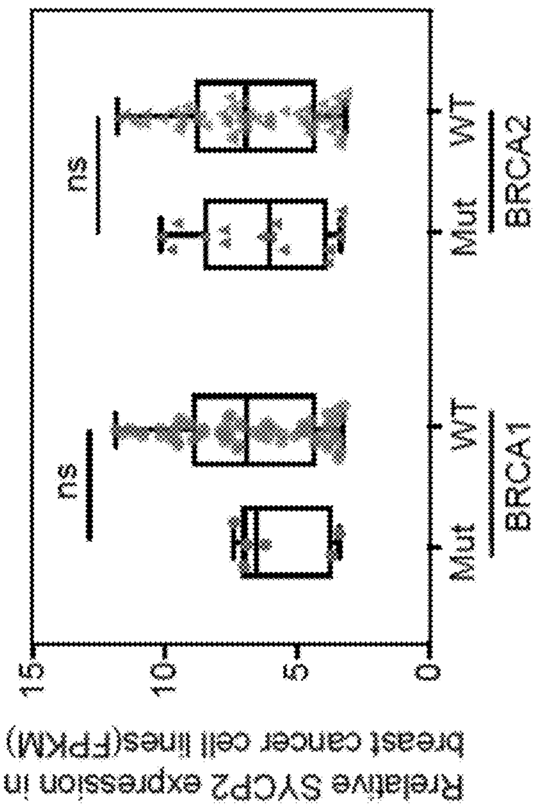
Figure 10D:
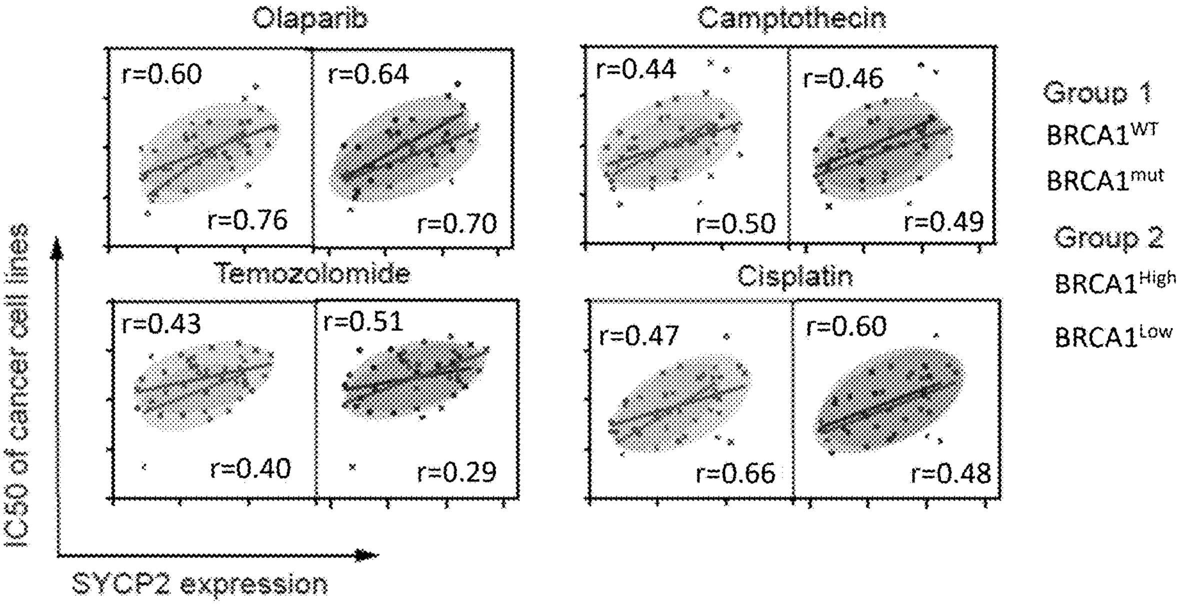

The functional relationship between SYCP2 and BRCA1 was investigated. HCC1954 and HCC1937 are two breast cancer cell lines defective for BRCA1 functions. Notably, substantial levels of IR-induced RAD51 foci remained detectable in the BRCA1-deficient cell lines HCC-1937 and HCC 1954, consistent with the BRCA1-independent HR activity. Knockdown of SYCP2 in HCC-1937 and HCC 1954 further reduced RAD51 foci (FIG. 10A), suggesting that SYCP2 can function independently of BRCA1. Consistent with this possibility, BRCA1 and SYCP2 formed IR-induced foci independently of each other (FIG. 10B). In the TCGA database, SYCP2 expression is not significantly different in tumors with and without BRCA1/2 mutations (FIG. 10C). Furthermore, the correlation between SYCP2 expression with PARPi sensitivity was identical in cell lines with and without BRCA1 mutations (FIG. 10D). Together, these results suggest that the function of SYCP2 in HR is independent of BRCA1.

Figure 10E:
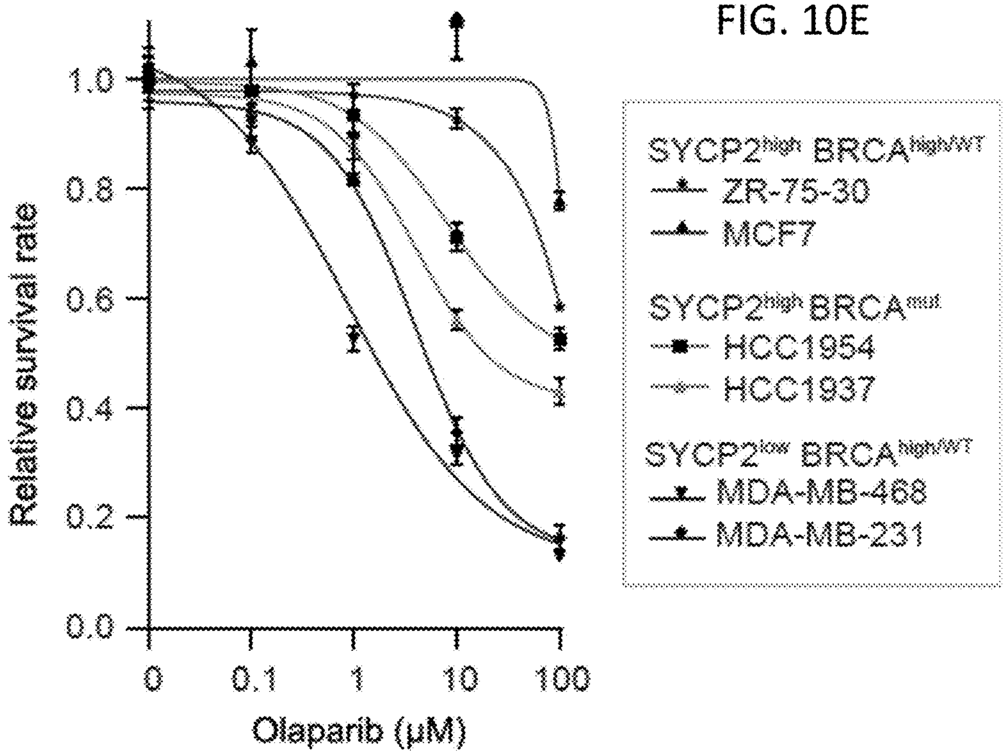

Next, we asked whether low SYCP2 expression predicts PARPi sensitivity independently of BRCA mutations using six breast cancer cell lines with or without BRCA mutations and expressing different levels of SYCP2. As expected, among the four cell lines expressing high levels of SYCP2, the two cell lines with BRCA1 mutations were more sensitive to PARPi (FIG. 10E). When the four cell lines without BRCA mutations were compared, the two cell lines with low SYCP2 expression were much more sensitive to PARPi (FIG. 10E). Notably, the increase of PARPi sensitivity associated with low SYCP2 expression was more prominent than that resulting from BRCA1 mutations, suggesting that in some contexts low SYCP2 expression may be a better marker to predict PARPi sensitivity than BRCA1 mutations.

SYCP2 Promotes RAD51 Recruitment in a Transcription-Dependent Manner

Figure 11A:
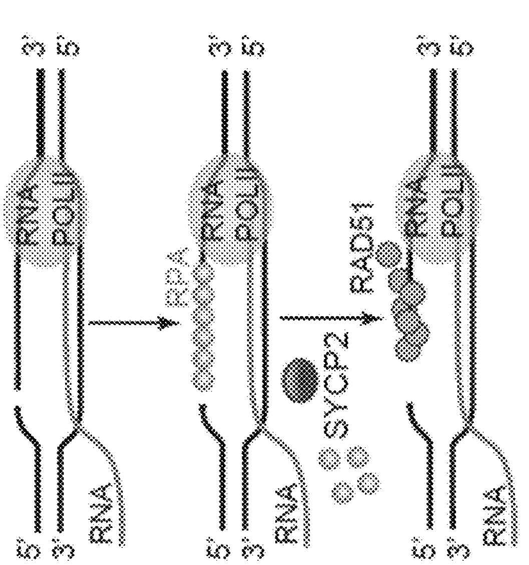
Figure 11A:
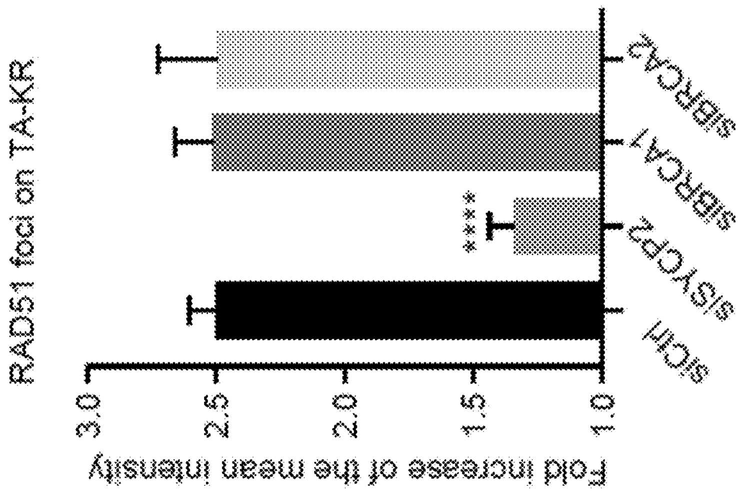

Recruitment of RAD51 to DSBs is enhanced in transcribed regions of the genome. We have previously established an inducible system in which RAD51 is recruited to a locus of ROS-induced DSBs in a transcription-dependent manner [Lan, L., et al. (2014). Novel method for site-specific induction of oxidative DNA damage reveals differences in recruitment of repair proteins to heterochromatin and euchromatin. Nucleic Acids Res 42, 2330-2345]. In this system, killer-red (KR), a light excitable ROS-releasing protein, was fused to the transcription activator (TA) VP16 and the Tet repressor (TetR). When the TA-KR fusion protein was targeted to an array of Tet Response Elements (TRE) in the genome, it activates transcription and generates ROS-induced DNA damage locally. Using this system, we found that SYPC2 was recruited to the locus bound by TA-KR and colocalized with γ-H2A.X. In contrast to TA-KR, fusion proteins unable to activate transcription or induce DNA damage (TetR-KR, TetR-cherry, and TA-cherry) did not trigger localization of SYCP2 to the locus, suggesting that SYPC2 is recruited in a transcription- and DNA damage-dependent manner. Furthermore, knockdown of SYCP2 reduced the localization of RAD51 to the TRE array in TA-KR expressing cells (FIG. 11A), confirming the role of SYCP2 in RAD51 recruitment. BRCA1 and BRCA2 were not required for RAD51 recruitment in this context. The recruitment of SYPC2 was not affected by the loss of BRCA1. Thus, in the context of ROS-induced DSBs in transcribed regions, SYCP2 promotes RAD51 recruitment in a transcription-dependent but BRCA1-independent manner.

SYCP2 Binds RAD51 and Promotes HR Through the KR Domain

Figure 11C:
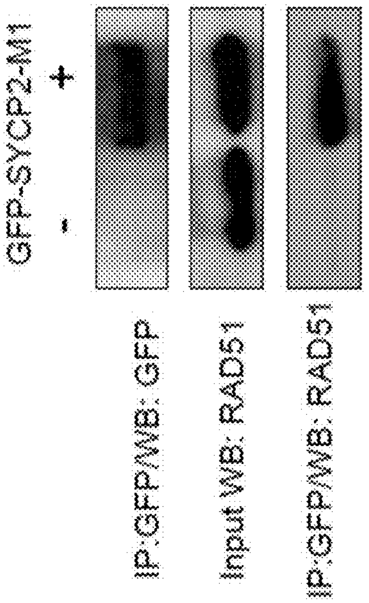
Figure 11C:
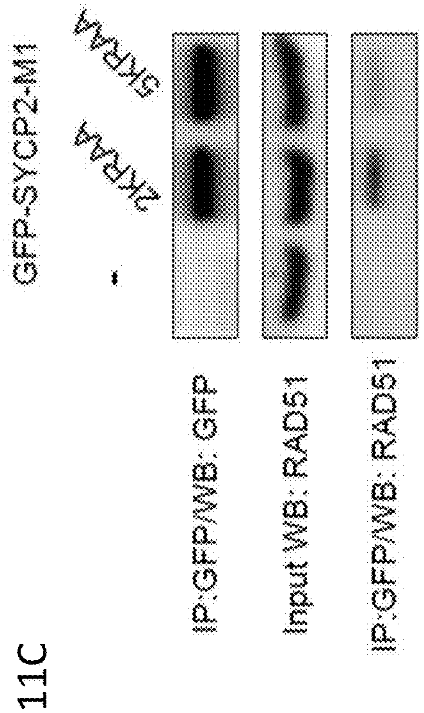
Figure 11B:
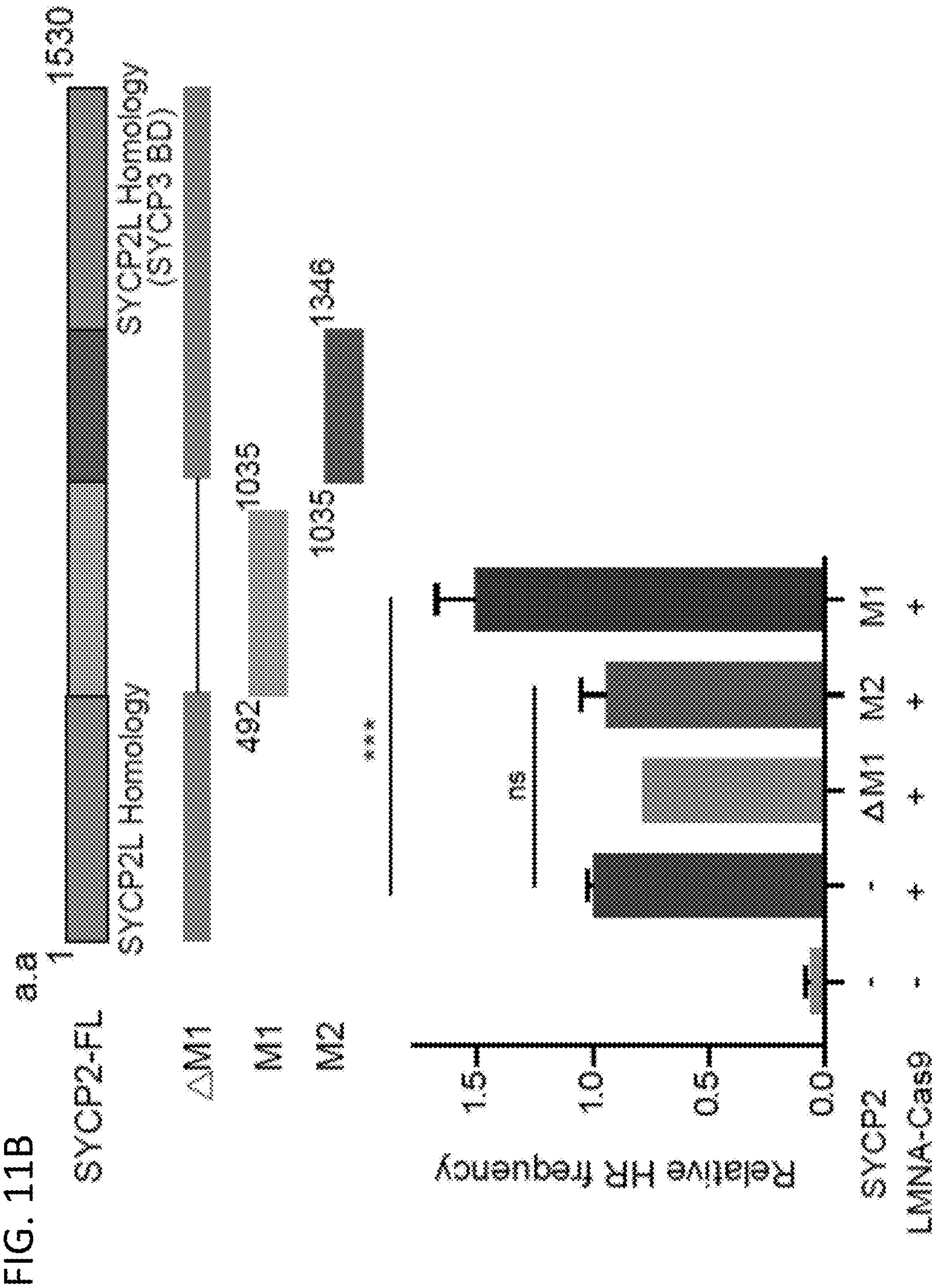

To understand how SYCP2 promotes RAD51 localization to DSBs, we overexpressed set of SYCP2 fragments (truncated M1, M2 and ΔM1) in cells (FIG. 11B upper panel). The N-terminal (1-394) domain (NTD) of SYCP2 is conserved in SYCP2L, whereas the C-terminal coiled-coil (CC) domain interacts with SYCP3. A HORMAD1 binding domain is next to the NTD of SYCP2, but the function of the rest (492-1346) of SYCP2 remain unknown. To assess the effects of SYCP2 fragments on HR, we analyzed the HR-mediated knock-in of mClover to a site of CRISPR-generated DSB in the LAMINA gene [Pinder, J., et al. (2015). Nuclear domain 'knock-in' screen for the evaluation and identification of small molecule enhancers of CRISPR-based genome editing. Nucleic Acids Res 43, 9379-9392]. Only the M1 fragment significantly increased HR (FIG. 11B lower panel), showing that the central region (492-1035) of SYCP2 is sufficient for its pro-HR activity.

Figure 11D:
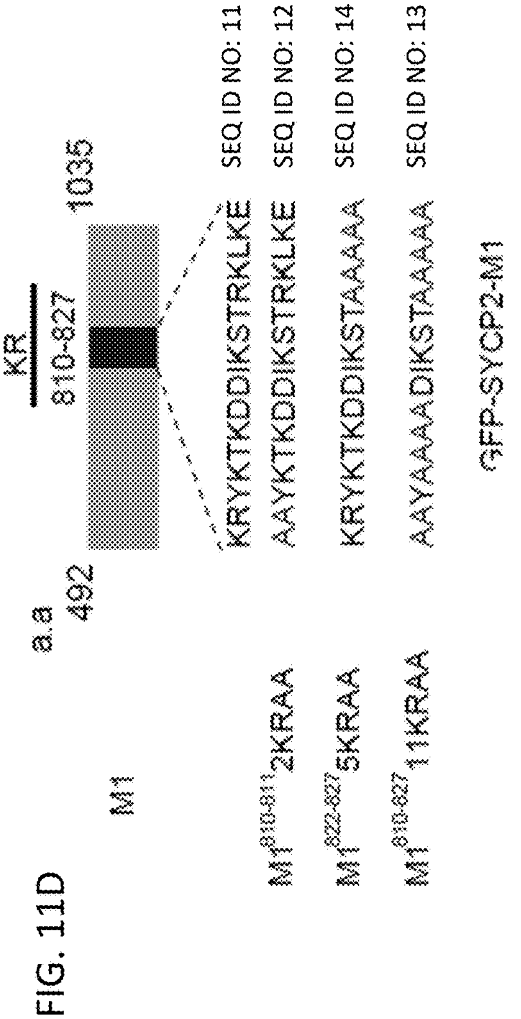
Figure 11E:
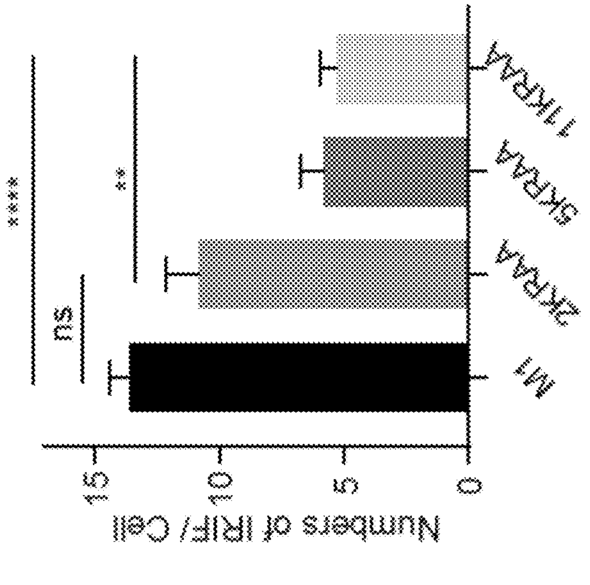
Figure 11F:
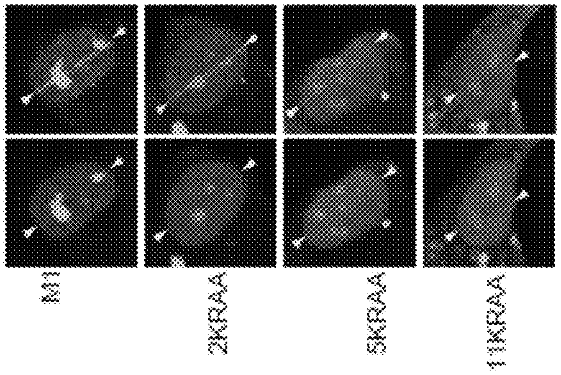
Figure 11G:
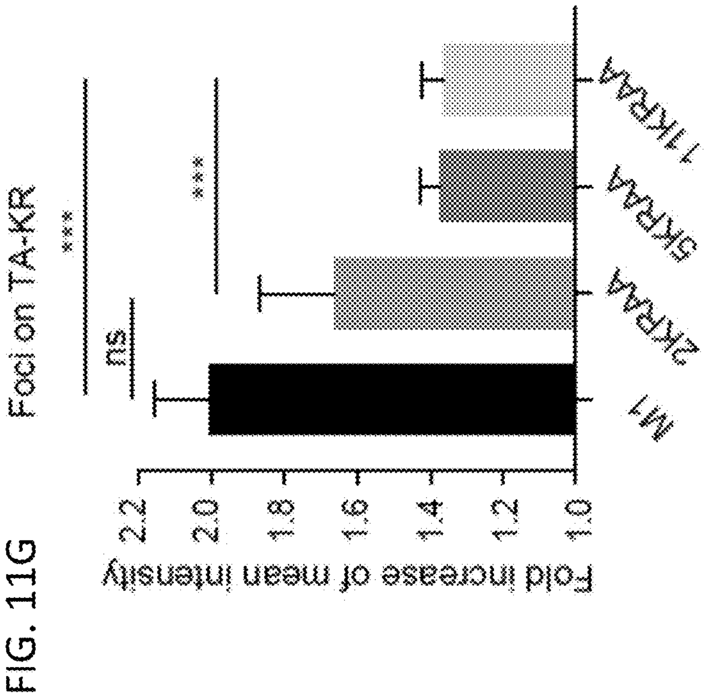
Figure 11H:
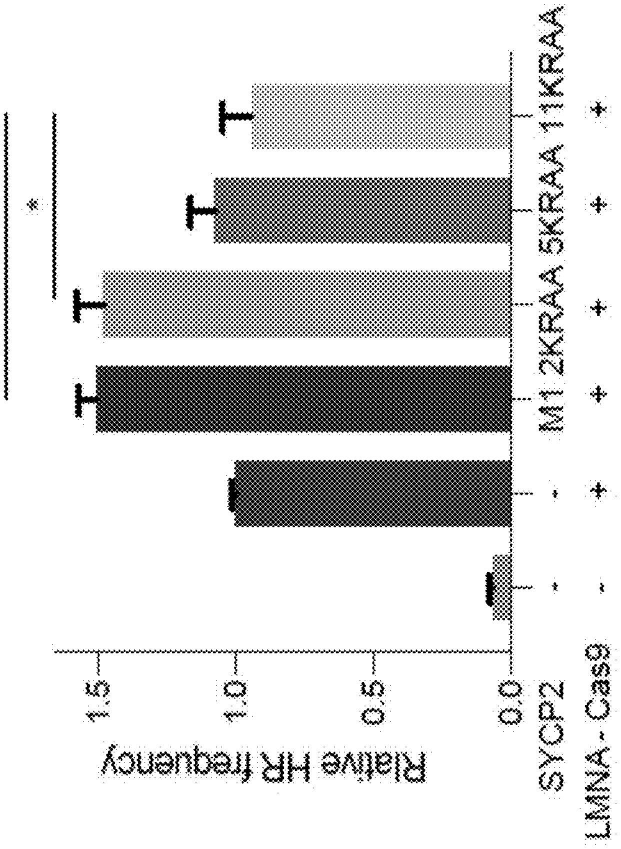

To understand how the M1 region of SYCP2 works, we searched for proteins with sequence homology. M1 shares homology with the BRCS domain of BRCA2. The BRCS domain of BRCA2 does not bind RAD51 directly but helps stabilize RAD51-ssDNA filaments by forming a BRCS-ssDNA-RAD51 complex. A interaction between M1 and endogenous RAD51 was detected by coimmunoprecipitation (FIG. 11C). The M1 fragment contains a lysine/arginine (KR)-rich region (FIG. 11D upper panel), which may be involved in protein and/DNA binding. Indeed, an M1 mutant (5KRAA) in which five of the KR residues are changed to alanines lost the ability to bind RAD51, whereas another M1 mutant (2KRAA) with only two of the KR residues mutated still interacted with RAD51 (FIG. 11D). Moreover, the binding of 2KRAA to RAD51 is dependent on DNA. When overexpressed in cells, wild-type M1 and 2KRAA localized to IR-induced foci more efficiently than 5KRAA and 11KRAA mutants (eleven KR residues are mutated to alanines in the 11KRAA mutant) (FIG. 11E). 5KRAA and 11KRAA mutants also displayed reduced localization to TA-KR-induced foci and stripes of laser induced damage (FIG. 11F, FIG. 11G). Consistent with their localization defects, in the mClover HR assay, 5KRAA and 11KRAA failed to enhance HR as wild-type M1 and 2KRAA (FIG. 11G). These results suggest that SYCP2 forms a complex with RAD51 and ssDNA through the KR residues in M1 to promote RAD51 filament formation. We therefore termed this KR-rich region (822-877) of SYCP2 the KR domain.

Figure 12A:
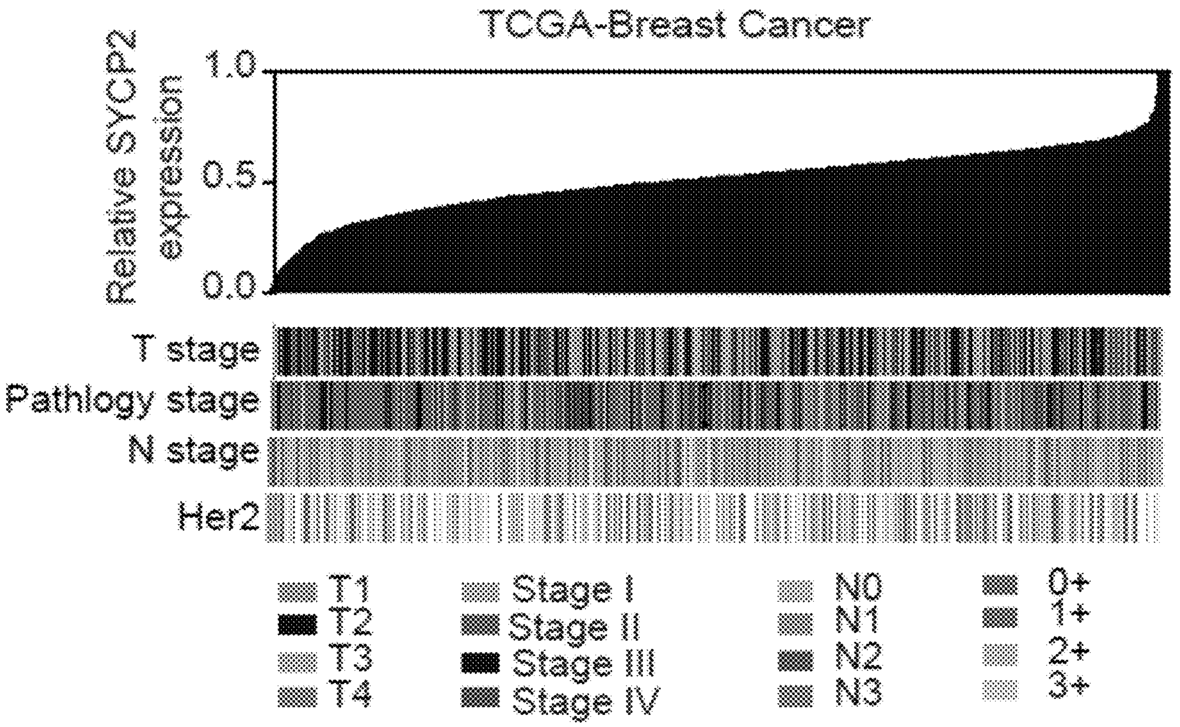
FIGS. 12A-12E show DNA hypomethylation at the SYCP2 gene associates with its expression in breast cancer.
Figure 12B:
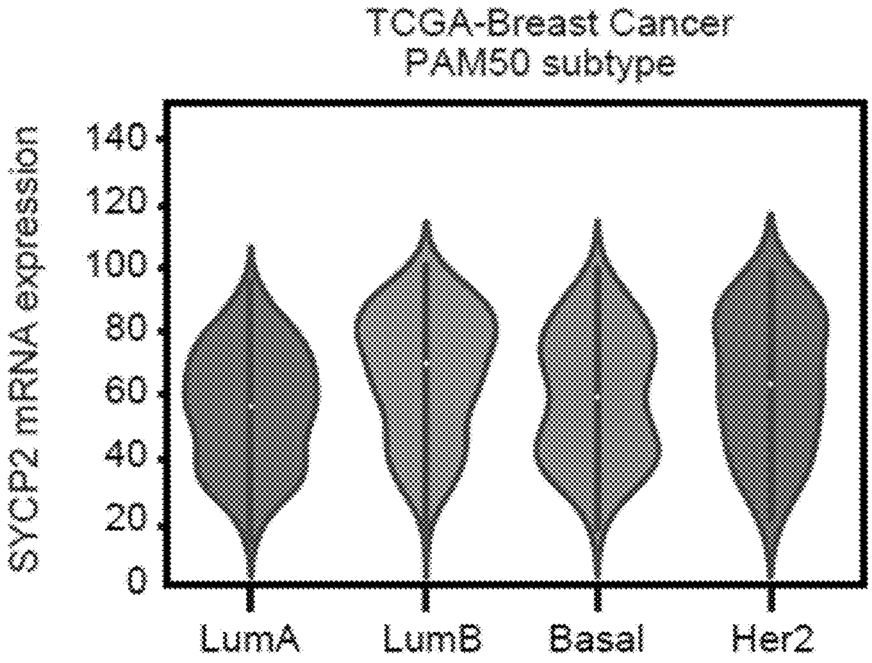
Figure 12C:
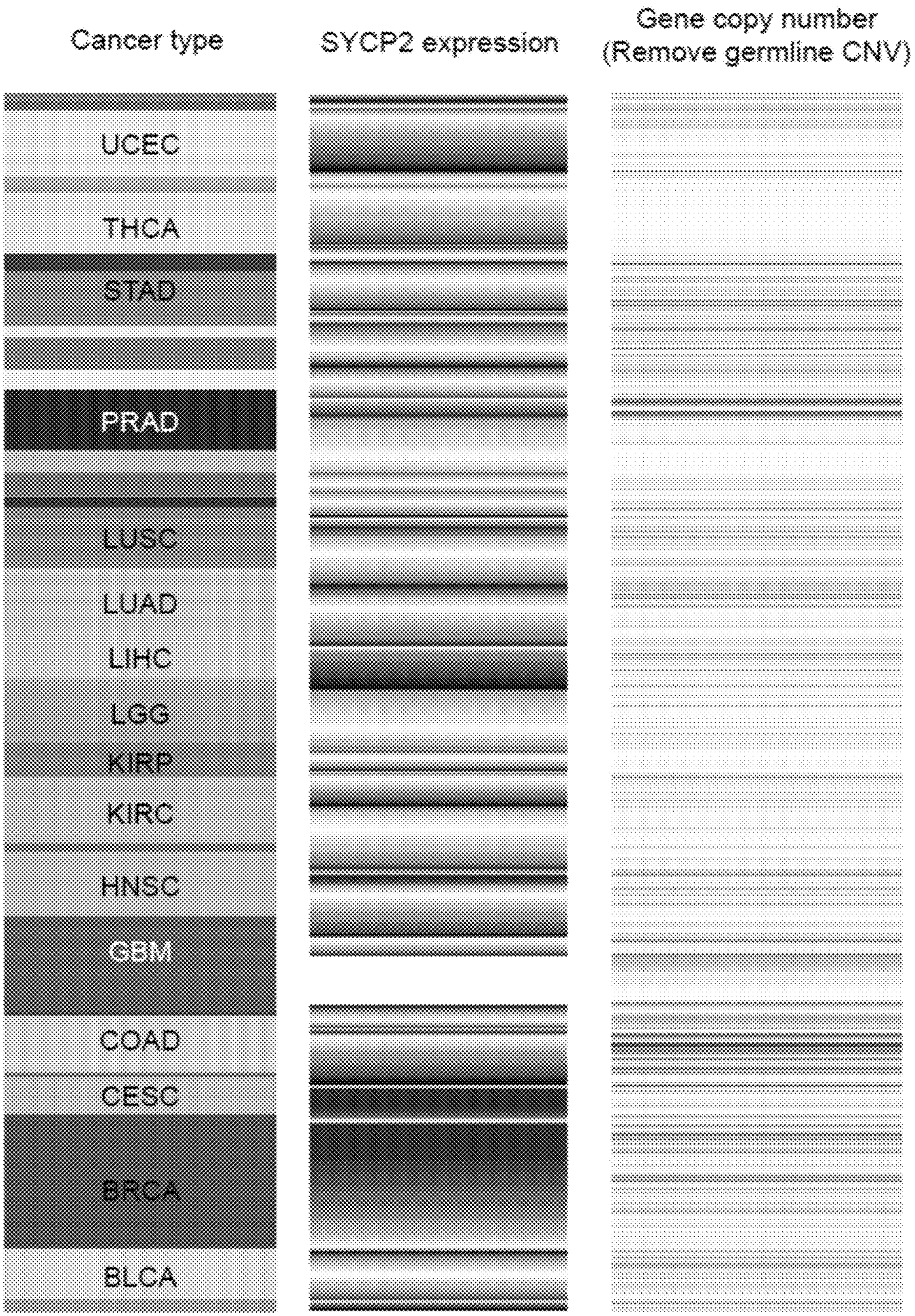
Figure 12C:
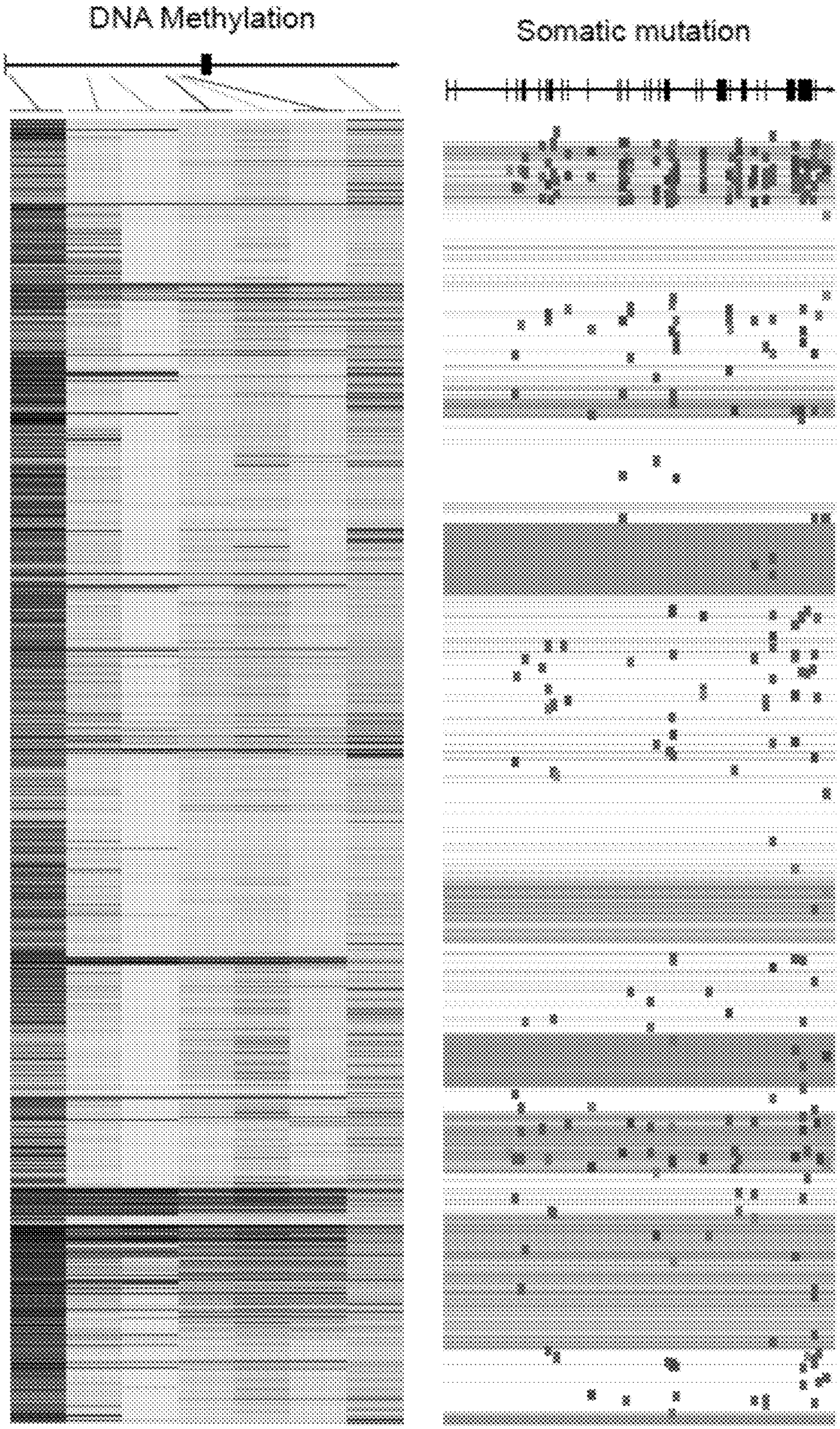
Figure 12D:
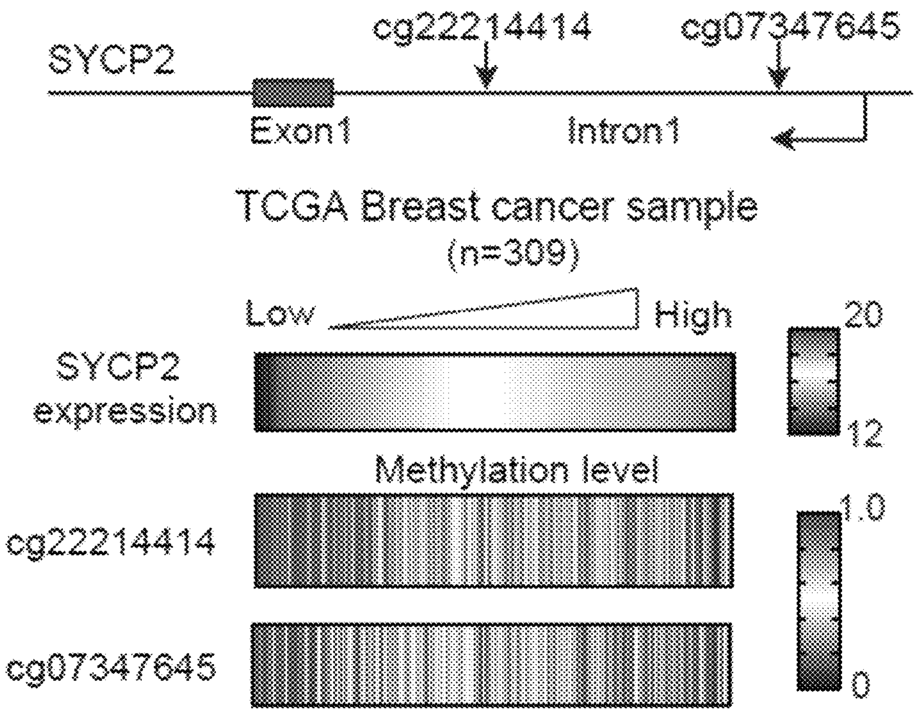
Figure 12E:
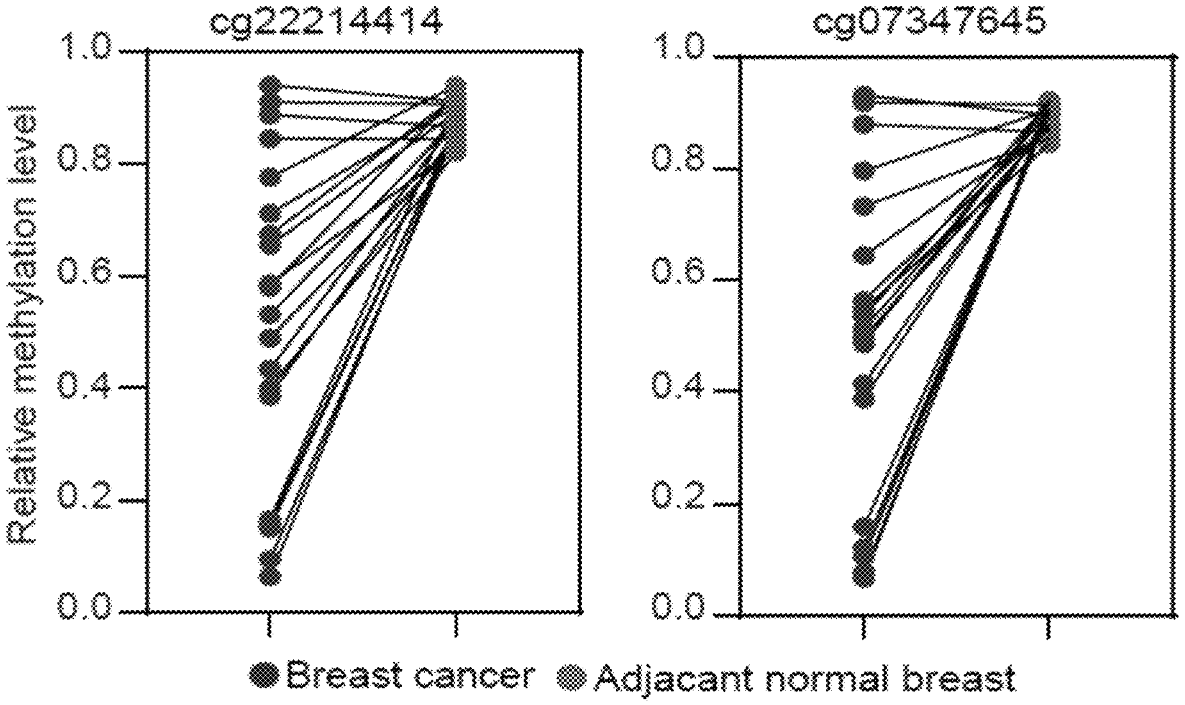

DNA Hypomethylation at the SYCP2 Gene Associates with its Expression in Breast Cancer The mRNA levels of SYCP2 in breast tumors do not correlate with tumor stages (T1-T4), pathological stages (StageI-IV), lymph node status (N0-N3) and Her2 levels (FIG. 12A). Furthermore, SYCP2 mRNA levels are not significantly different in different subtypes of breast cancers (FIG. 12B). We then considered if the up regulation comes from the genomic variations including copy number variants (CNV), DNA methylation levels and somatic mutations. Notably, the SYCP2 gene locus was hypomethylated only in breast cancer (FIG. 12C). To understand if SYCP2 is up regulated by DNA hypomethylation, we selected two sites in the intron 1 of SYCP2 and measured the levels of DNA methylation in 309 breast cancer samples in the TCGA database (FIG. 12D). We found that low DNA methylation at these two sites strongly correlated with high SYCP2 expression. In addition, DNA hypomethylation at these two sites was only detected in breast cancer tissues but not in adjacent normal breast tissues (FIG. 12E). These results suggest that DNA hypomethylation of the SYCP2 gene is likely the cause of its expression in breast cancers.

Figure 13A:
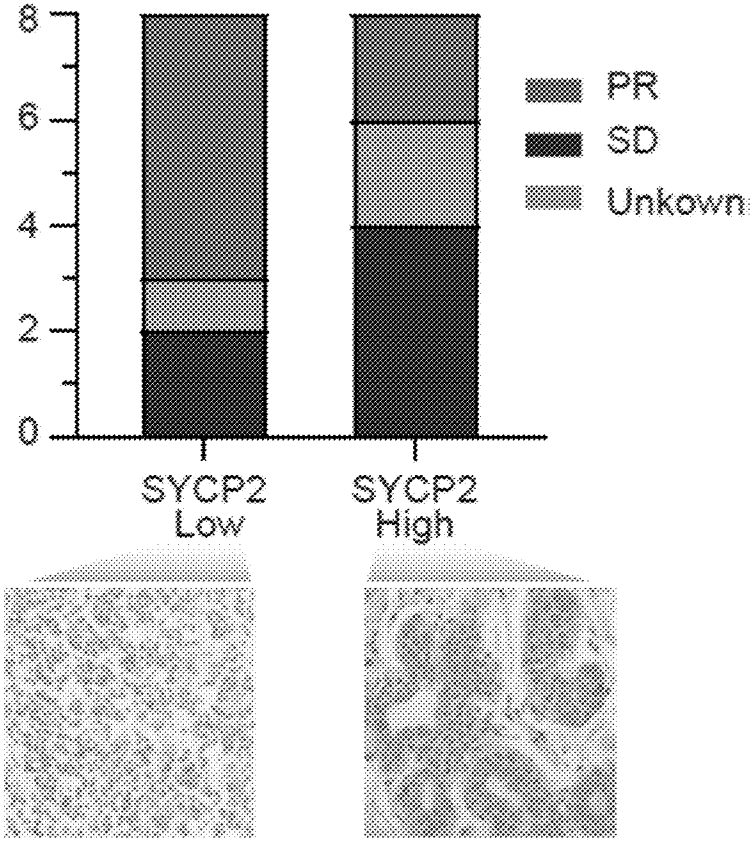
FIGS. 13A-13D show high SYCP2 expression associates with poor prognosis and drug resistance in patients.
Figure 13B:
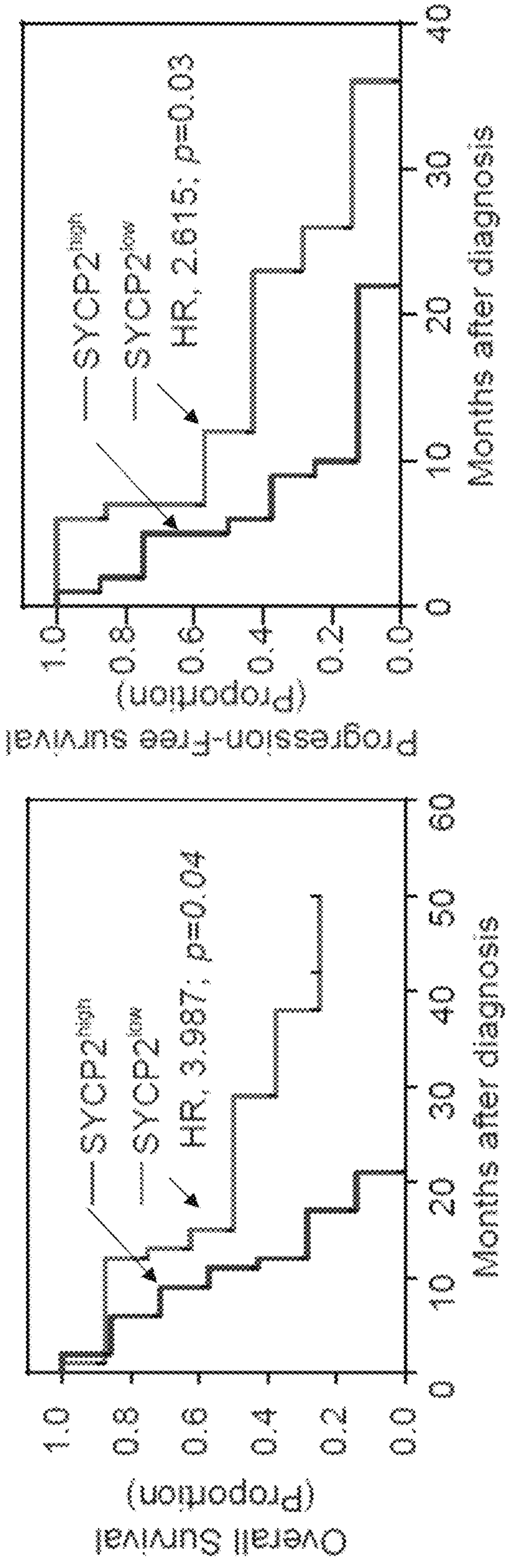
Figure 13C:
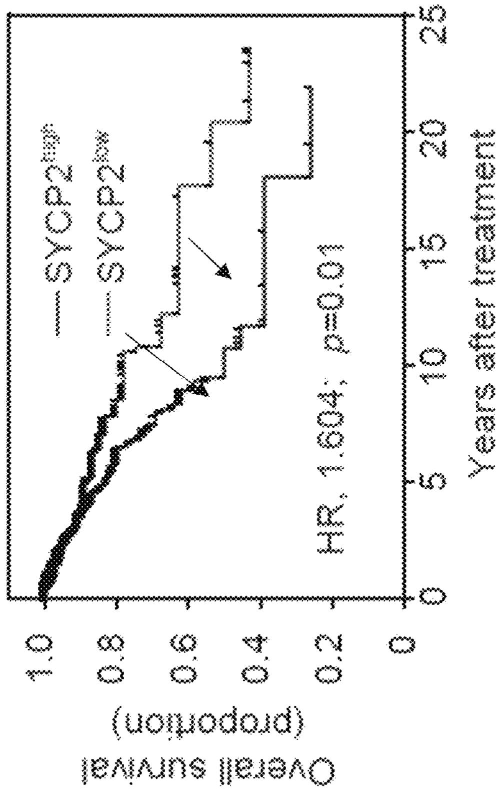
Figure 13D:
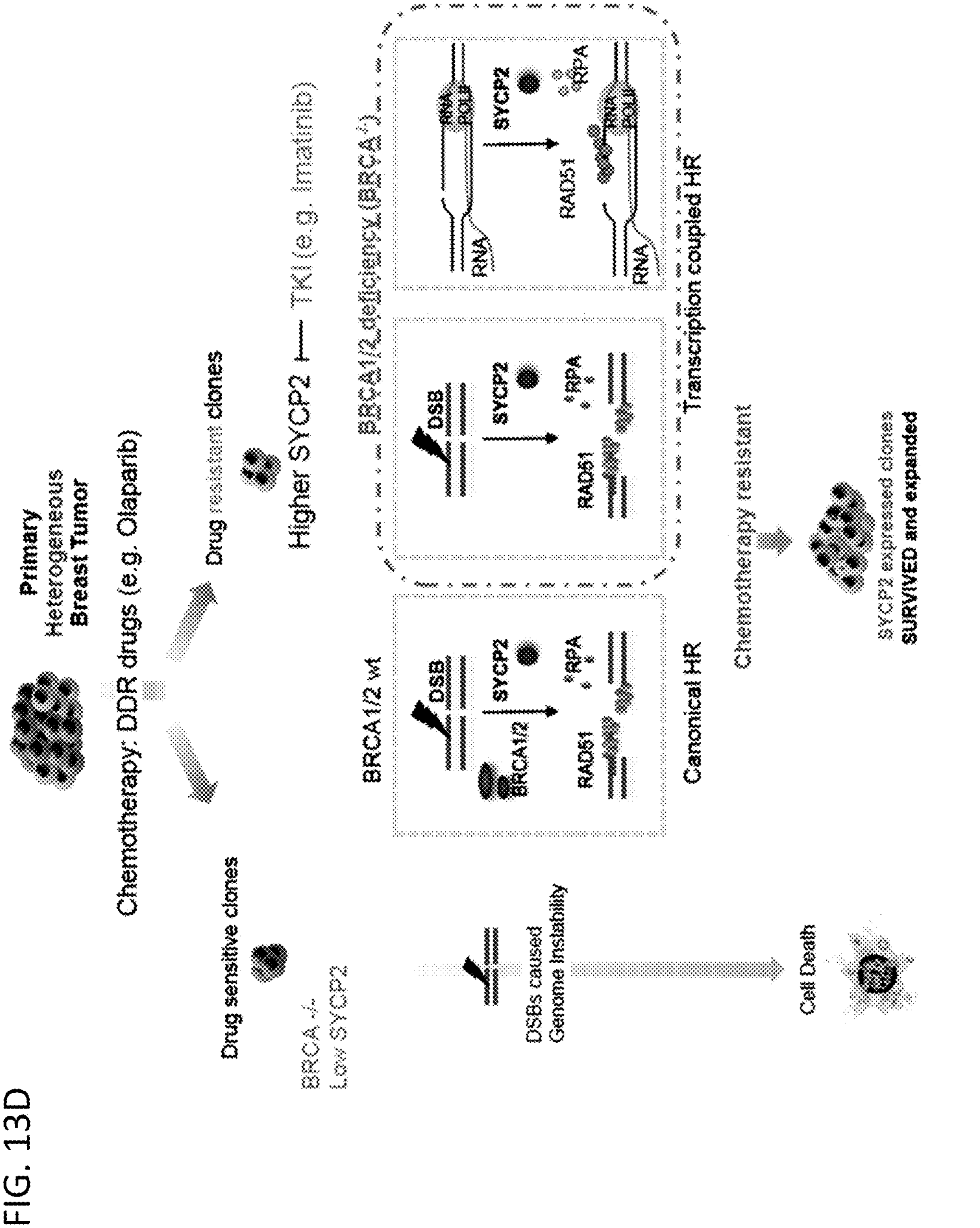

High SYCP2 Expression Associates with Poor Prognosis and Drug Resistance in Patients Based on our analysis of SYCP2 expression in tumors in databases, we performed immunohistochemistry (IHC) analysis of SYCP2 in breast cancer tissues and adjacent normal breast tissues from patients. SYCP2 levels were specifically up regulated in breast cancer tissues. To understand whether SYCP2 levels affect clinical outcomes, we analyzed 16 patients (7 luminal ER/PR positive, 8 triple negative, and 1 unknown) form a clinical trial in which patients were treated with TOP1 inhibitor, Sacituzumab Govitecan (IMMU-132) (FIG. 13A). We performed IHC analysis on tissue microarrays of breast tumors, metastatic sites, and adjacent normal tissues from all 16 patients. SYCP2 was specifically up regulated in breast tumors and at metastatic sites compared to normal tissues from breast, brain, and lymph node. Next, we assessed SYCP2 levels in tumor tissues based on IHC staining. The $SYCP2^{low}$ group represents tumors with <50% cells positive for SYCP2, whereas the $SYCP2^{high}$ group represents tumors with >50% cells positive for SYCP2. Representative images of tumors with low or high SYCP2 are shown (FIG. 13A). Our analysis shows that patients with $SYCP2^{high}$ tumors had a reduced rate of partial response (PR) but an increased rate of stable disease (SD) (FIG. 13A), suggesting that high SYCP2 expression in tumors associates with reduced efficacy of TOP1 inhibitor. Correspondingly, high SYCP2 expression was significantly correlated with shorter overall survival and progression-free survival among patients in this clinical trial (FIG. 13B). Furthermore, the clinical data of 1,095 breast cancer patients from the TCGA database confirm that high SYCP2 expression associates with poor prognosis (FIG. 13C). Thus, SYCP2 is both predictive of response and prognostic of outcome in patients (FIG. 13D).

Discussion

DDR-targeted drugs, including DNA-damaging chemotherapeutics and DNA repair inhibitors, are widely use in cancer therapy today. While these drugs are effective in the clinic, drug resistance remains a major challenge. We used a bioinformatic approach to identify SYCP2 as a gene whose expression in cancers strongly correlates with resistance to a panel of DDR-targeted drugs. SYCP2 is specifically up regulated in several cancer types, including breast, cervical and lung cancers. In breast cancer, the up regulation of SYCP2 is likely a result of DNA hypomethylation. Importantly, the high expression of SYCP2 is associated with resistance to a broad spectrum of DDR-targeted drugs, including PARP inhibitors, TOPI and TOPII inhibitors, DNA crosslinkers and others. In contrast, the resistance to drugs targeting other pathways does not correlate with SYCP2 expression. These results suggest that high SYCP2 expression is a biomarker that broadly predicts resistance to DNA damage and DNA damaging agents.

It is interesting to note that SYCP2 is a mitotic protein involved in the recombination between homologous chromosomes. Up regulation of mitotic DNA repair/recombination proteins may be a common mechanism conferring DNA damage resistance in tumors. For example, the up regulation of the meiotic recombinase DMC1 has been linked to PARPi resistance. However, it should be noted that SYCP2 but no other component of the SYC or cohesion complex is associated with DNA damage resistance, suggesting that SYCP2 functions differently from its normal meiotic role in the context of drug resistance. Notably, DMC1 rather than RAD51 is the main recombinase that functions in meiosis (Da Ines et al., 2013). It is conceivable SYCP2 acquires the ability to bind RAD51 when it is aberrantly expressed in mitotic cells. This is consistent with the idea that rewiring of DNA repair/recombination pathways is a major mechanism driving the resistance to DDR-targeted drugs, revealing a similarity between the rewiring of DNA repair pathways and that of the classic signaling pathways altered in cancers.

We demonstrate that SYCP2 overexpression is sufficient to enhance HR and confer DNA damage resistance. This function of SYCP2 is linked to the localization of RAD51 to sites of DNA damage. Interestingly, however, SYCP2 is able to promote RAD51 localization independently of BRCA1, a well-known regulator of HR. SYCP2 promotes RAD51 localization even in BRCA1-deficient cells and at a locus of ROS-induced DNA damage where HR is independent of BRCA1. The role of SYCP2 in recruiting RAD51 to the locus of ROS-induced DNA damage is transcription-dependent, suggesting that SYCP2 may be regulated by RNA. It is important to note that SYCP2 loss reduces HR by ~50%, suggesting that it is not only involved in the residual BRCA1-independent HR. In cancer cells expressing SYCP2, it may function with BRCA1 to promote HR. Consistent with this possibility, SYCP2 is not specifically up regulated in BRCA cancers. Instead, the high expression of SYCP2 associates with drug resistance in tumors with and without BRCA mutations.

Our results also explain how SYCP2 promotes the recruitment of RAD51 to DSBs. Surprisingly, we identified a BRC-like domain in SYCP2. We found that abolish the KR motif in KR-rich domain attenuated the interaction of SYCP2 with RAD51. Therefore, SYCP2 uses this KR-rich domain to interact with RAD51 in a DNA-dependent manner, suggesting that SYCP2 forms a complex with RAD51 and ssDNA and promotes RAD51 filament formation. Normal mitotic cells lacking SYCP2 do not need this mechanism for HR. However, in cancer cells expressing SYCP2, this mechanism contributes to the heightened HR and DNA damage resistance. It is possible that SYCP2 is normally repressed in mitotic cells because SYCP2-driven HR is deleterious in certain contexts, or because it is strictly controlled by a meiotic program. The aberrant expression of SYCP2 in breast cancer allows cancer cells to tolerate genomic instability, thereby promoting tumorigenesis and priming cancer cells to drug resistance.

While the expression of SYCP2 in breast tumors drives resistance to DDR-targeted drugs, it may also offer a target for therapy. It is conceivable that inhibition of HR would overcome the resistance of SYCP2-expressing cancer cells to DNA damage and DDR-targeted drugs. Drugs or compounds that inhibit HR independently of BRCA1/2 may be particularly useful in this context.

Materials and Methods

Cell Culture, Plasmids and siRNAs

U2OS TRE, HCC1954, HCC1937, MDA-MB-231, MDA-MB-438, MCF7, T47D, CAMA1, HeLa, and 293 (ATCC) cells were cultured in Dulbecco's modified Eagle medium (DMEM, Lonza, Catalog #12-604F) with 10% (vol/vol) fetal bovine serum (FBS) at 37° C., 5% CO2. ZR75 cells were cultured in Dulbecco's modified Eagle medium (DMEM, Lonza, Catalog #12-604F) with 15% (vol/vol) fetal bovine serum (FBS) at 37° C., 5% CO2. The U2OS THE cell line for the DNA damage targeted at the telomeres (DART) system is derived from wild-type U2OS cells (ATCC) by inserting an array of TRE/I-SceI and a transcription cassette in the genome. pBROAD3/TA-KR, tetR-KR, TA-Cherry, tetR-Cherry, pEGFP-RAD52, pEGFP-SYCP2 pEGFP-CSB, pEGFP-TRDEMT1, pEGFP-plasmids were used for the DART system. CMV-SYCP2-myc-DDK plasmid was used for HR assay. SYCP2 fragments 492-1035, 1036-1346 were cloned into pEGFP-C3 vectors using KpnI and BamHI as digestion sites. The 510-960 fragment has an added NLS sequence in the N terminus to ensure nucleus localization. The 2KRAA, 5KRAA, and 11KRAA mutants in the SYCP2 492-1035 (SYCP2-M1) fragment were created using DNA synthesis from Geneuniversal. Plasmids were transfected by Lipofectamine2000 (Invitrogen) using a standard protocol. siRNAs were transfected with Lipofectamine RNAiMax (Invitrogen) 48-72 h before analysis. The siRNAs used in this study are siSYCP2 (Integrated DNA technologies: GUCCAAGGAAUCAUGAUGAACUUAA (SEQ ID NO: 10), siRAD51 (E-003530-00, Dharmacon), siBRCA1 (L-003461-00, Dharmacon), and siBRCA2 (GS675, Qiagen) and SmartPool siRNAs targeted at RPA1 were all purchased from Dharmacon.

Immunofluorescence Staining and Microscopy

Cells in a 35 mm dish were rinsed with phosphate-buffered saline (PBS) and fixed in 4% paraformaldehyde (PFA; Affymetrix, 19943 1 LT) for 15 min at room temperature. They were washed three times by PBS, permeabilized by 0.2% Triton X-100 in PBS for 15 min, then washed three times by PBS. Then they were blocked by 5% bovine serum albumin (BSA) (SIGMA, A 7030) in PBS for 1 hour at room temperature. Primary antibodies were diluted in blocking buffer and incubated with cells overnight at 4° C. Then the cells were washed three times with 0.05% PBST and incubated with secondary antibodies for one hour at room temperature, including Alexa Fluor 405/488/594 goat anti-mouse/rabbit IgG conjugate (1:3000). Finally, they were washed three times by 0.05% PBST and optionally stained with DAPI (4',6-diamidino-2-phenylindole; 1:1000 in PBS) for 5 min at room temperature. The primary antibodies for immunoassays are SYCP2 (PAS-66486, Invitrogen, 1:500) RAD51 (ab63801, Abcam, 1:100), γH2AX (JBW301, 05-636, EMD Millipore, 1:400), BRCA1 (D-9, sc-6954, Santa Cruz Biotechnology, 1:100), RAD21(#4321, D213, Cell Signaling Technology, 1:100), hFAB Rhodamine anti-tubulin (#12004166, Bio-Rad, 1:1000).

Homologous Recombination Assay

For DR-GFP HR assay, cells were seeded into 6-well plates and transfected with 2 μg of the I-SceI expression plasmid (pCBASce) and 4 μg of the pCMV-SYCP2-myc-DDK plasmid using FuGENE 6 transfection reagent (Promega); GFP fluorescence was assessed by FACS 72 hours after transfection. For knockdown assays, cells were transfected with siRNA 24 hours prior to I-SceI transfection. For mCherry Homologous Recombination Assay, Cells were seeded into a 35 mm glass-bottom dish and transfected with 0.6 μg of the LuminA expression plasmid (pCBASce), 0.3 μg of the sgRNA plasmid using and 0.5 ug SYCP2 fragment plasmids by using FuGENE 6 transfection reagent (Promega); Puromycin (1:1000) added after 24 hours transfection. Cells were fixed by 4% after 48 hours and counted under confocal.

Colony Formation Assay

Approximately 400 cells were replanted on 6-cm dishes 48 h after siRNA transfection. For treatment with Olaparib or cisplatin, cells were incubated in DMEM (10% FBS) containing compound for 9 days. For treatment with UVC light and ionizing radiation (IR), cells were washed and irradiated with the indicated dose 8 h after passaging. Colonies were stained with 0.3% crystal violet/methanol and counted 9 days after treatments. Each experiment was performed at least 3 times and the standard errors were calculated and indicated in the graphs. Results were normalized for plating efficiencies.

Microscope and Laser Micro-Irradiation

The Olympus FV/1000 confocal microscopy system (Olympus) and FV/1000 software were used for image acquisition and analysis and described in a previous study. The damage was induced with a 405 nm laser. The laser passed through a PLAON 60× oil lens. Cells transfected with GFP-tagged proteins were incubated at 37° C. on a thermos plate in normal media during observation. Before laser damage, cells were treated with 8-mop to sensitize. For the evaluation of accumulation and kinetics, the mean intensity of each accumulated point or line was obtained after subtraction and quantified by ImageJ.

KillerRed Induced Damage Response

U2OS THE cells were cultured in 35 mm glass-bottom dishes (MatTek, P35GC-1.5-14-C). Cells were transfected with plasmids containing Killerred protein (TA-KR/tetR-KR). For ROS induced damages, cells were exposed to a 15W Sylvania cool white fluorescent bulb for 10-20 minutes. Cells were then recovered at around 30 minutes to an hour before live-cell observation or fixation. For γH2AX staining, cells were recovered for 12, 24 and 48 hours before fixation.

Co-Immunoprecipitation and Western Blots

Flip-in 293 cells were co-transfected with expression vectors 36-48 h after transfection; cell lysates were collected in 1 mL of lysis buffer (10 mM Hepes, pH 7.6; 50 mM Tris-HCl, pH 7.4; 150 mM NaCl; 1% NP-40; 3 mM EDTA; protease inhibitor from Roche). For anti-green fluorescent protein (GFP) immunoprecipitation, 2 μg anti-GFP monoclonal antibody (11814460001, Roche), and 25 μL of G-Sepharose protein beads (GE Healthcare Bio-Sciences) were added to each lysate. Mixtures were incubated at 4° C. overnight with rotation; the supernatant was removed and protein beads were washed four times using 0.4 mL of lysis buffer. For western blotting analysis, samples were boiled at 95° C. for 5-8 min in SDS loading buffer. Then they were subjected to electrophoresis in 10-12% SDS-polyacrylamide gels and transferred to the polyvinylidene difluoride membrane. The membranes were blocked with 5% non-fat milk in PBS for 1 h before being incubated with the primary antibody at 4° C. overnight. The primary antibodies for western blotting used in this study are GFP (11814460001, Roche, 1:2000), SYCP2 (LS-C386874, LifeSpan BioSciences, 1:1000), RAD51 (ab63801, Abcam, 1:1000), BRCA1 (D-9, sc-6954, Santa Cruz Biotechnology, 1:100), 0-actin (#3700, 8H10D10, Cell Signaling Technology, 1:1000). Then the cells were washed three to four times with 0.1% PBST and incubated with horseradish peroxidase (HRP)-conjugated secondary antibody (1:10,000) for 1 h at room temperature. The membranes were washed in 0.1% PBST for four times before exposure. Chemiluminescent HRP substrate was purchased from Abcam (Catalog #: WBKLS0500). Images were acquired in a BIO-RAD Universal Hood II machine with ImageLab software.

Cell Cycle Analysis by Flow Cytometry

The cells were collected and fixed in cold 70% ethanol at 4° C. overnight. The cells were washed once with 2% BSA in PBS and incubated in PBS solution containing 2% BSA, 50 μg/mL propidium iodide, and 100 μg/mL RNase A in the dark for 30 min before being analyzed by flow cytometry.

Mice Model and Xenograft

Lentiviral (LV-SYCP2-RNAi or LV-NC-RNAi) transfected MD-MBA-231 (6.0×105) were injected intraperitoneally into the BALB/c nude mice. The transfected mice were then randomly divided into four groups. After the injection of lentiviral transfected cancer cells. Mice would develop a palpable tumor within a week. At day 7, Olaparib and/or saline was intraperitoneally injected into the xenograft tumors once every 2 days after day 7 for 8 times, around 20 days. Mice were sacrificed at day 23. Tumors were harvested, then fixed and embedded in paraffin. The embedded tumor was then sectioned into 4 μm slices. The sectioned slices were deparaffinized and rehydrated before staining. The rehydrated sections were then blocked and incubated with primary antibody SYCP2 (PA5-67554, Invitrogen) and Ki-67 (sc-23900, Santa Cruz Biotechnology), then detected using the Dako Envision two-step method of immunohistochemistry (Carpinteria, CA, USA).

Clinical Sample Data

A tissue microarray data comprising 16 breast cancer patients fixed sample was obtained from the Massachusetts general hospital cancer center. A detailed description of clinicopathologic features has been published previously and is provided in Supplementary FIG. S5C.

Immunohistochemistry and Tissue Staining Evaluation

The collected tumor specimens and adjacent normal tissue samples were fixed in 4% parafoiinaldehyde, stored in PBS. After sucrose infiltration, samples were filled with OTC and ready for cryosection. The immunohistochemistry staining, scoring and analysis followed a triple-blinded manner. The images were captured through a light compound microscope following the manual for pathological specimen from Specialized Histopathology Core at MGH. The counting of positive cells and analysis were performed by one pathologist and one investigator separately in a blinded fashion. Immunohistochemistry and scoring Tumors were fixed, embedded in paraffins and sectioned into 4 μm thickness in animal study. After deparaffinization and rehydration, sections were blocked and incubated with antibody against SYCP2 (PAS-67554, 1:20), Ki-67 (sc-23900, Santa Cruz, 1:200), and then detected using the Dako Envision two-step method of immunohistochemistry (Carpinteria, CA, USA). Cold sectioning and staining with Ki67 and SYCP2 antibodies (PAS-67554, 1:20) were performed by the Specialized Histopathology Services-MGH at Massachusetts General Hospital-East. All IHC staining was scored independently by 2 pathologists. We divided the positive staining results into 0-4 categories as following: 0: <5%; 1: 6-25%; 2: 26-50%; 3: 51-75%; and 4: >76% staining. SYCP2 low group contains categories 0 and 1; and SYCP2 high group contains categories 3 and 4. Cold sectioning and staining with Ki67 and SYCP2 antibodies (PA5-67554, 1:20) were performed by the Specialized Histopathology Services-MGH at Massachusetts General Hospital-East.

Figure 14B:
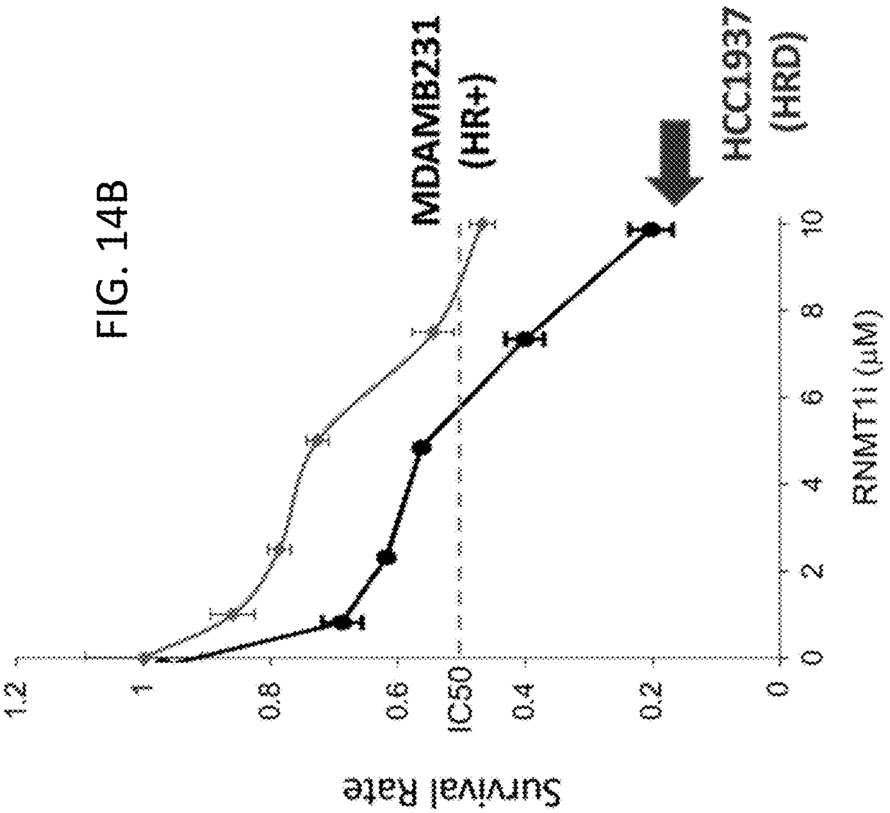
FIGS. 14A-14C show TRDMT1i alone reduce cancer cell survival in a dose-dependent manner.
Figure 14A:
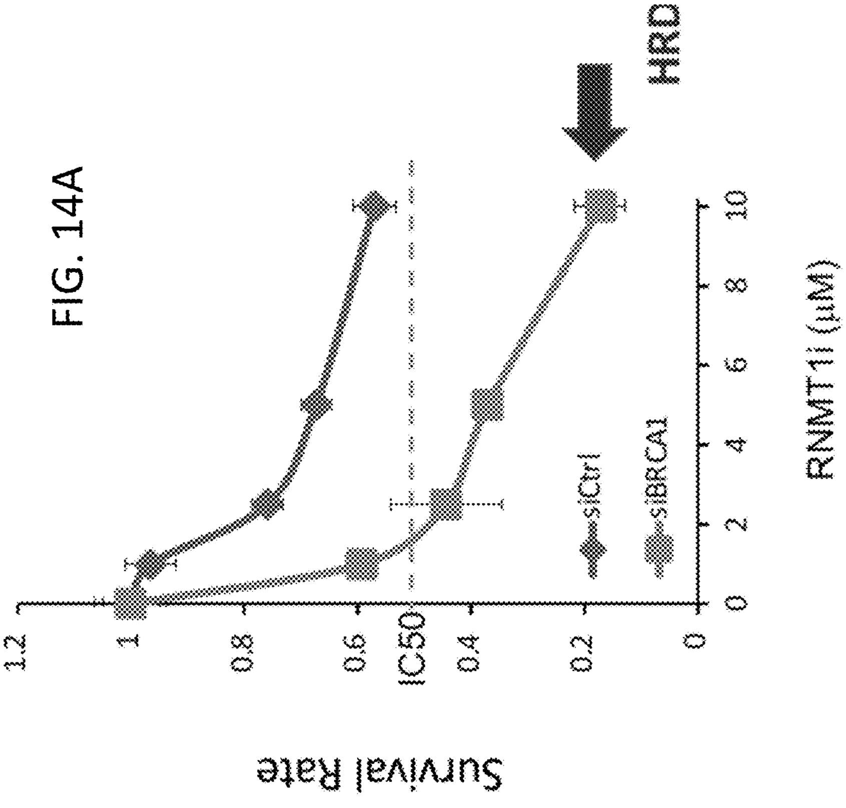

Example 19. TRDMT1i Alone Reduce Cancer Cell Survival in a Dose-Dependent Manner TRDMT1i alone kills HR-proficient cancer cells HST578 in a dose-dependent manner. Notably, BRCA1 knockdown significantly increased TRDMT1i sensitivity (FIG. 14A). Our results suggest that HR deficient cells are more sensitive to TRDMT1i alone. (FIG. 14B).

SYCP2 Level as Well as HR Status Predicts Drug Response to TRDMT1i

Figure 14C:
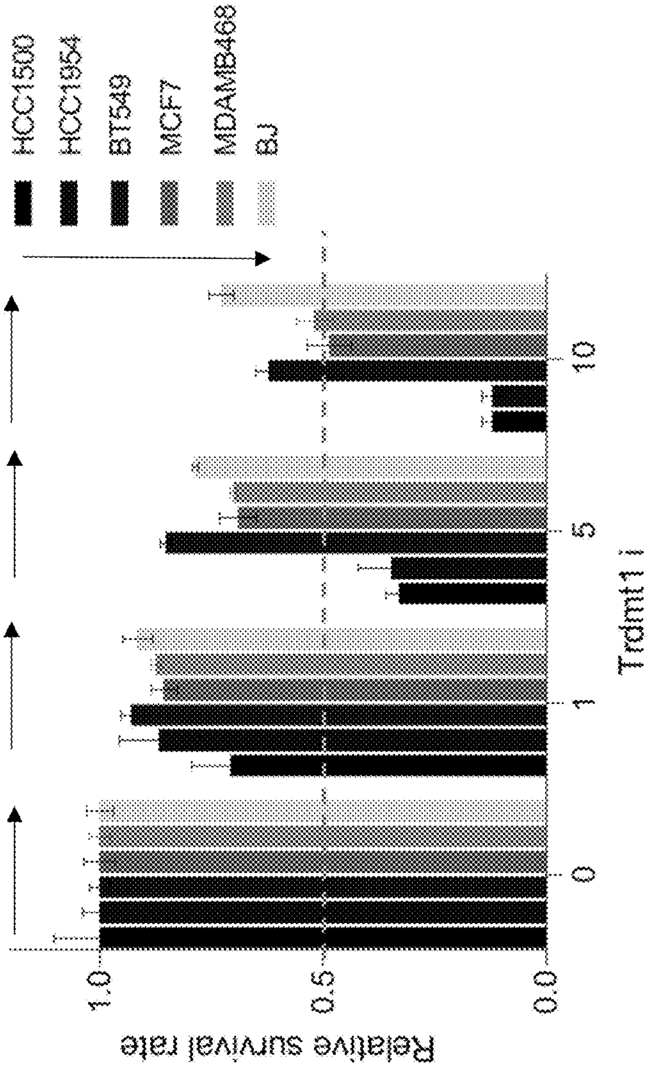

TRDMT1i killed SYCP2-high cancer cell lines and HR deficient cells the most efficiently. (FIG. 14C) HCC1954, which is HRD but express high levels of SYCP2, are relatively resistant to PARPi. TRDMT1i efficiently killed HCC1954. Our results suggest that TRDMT1i preferentially kill SYCP2-high cancer cells and HR deficient cells.

Cell Culture and Transfection

HCC1500, HCC1954, BT549, MCF7 and MDAMB468 were cultured in Roswell Park Memorial Institute (RPMI) 1640 Medium (Sigma, R8758) with 10% (vol/vol) fetal bovine serum (FBS, XY Cell Culture, FBS-500) at 37° C., 5% $CO_2$. siBRCA1 (L-003461-00, Dharmacon) was transfected with Lipofectamine RNAiMax (Invitrogen; Carlsbad, CA, USA). PARPi Olaparib (AZD2281/Ku-0059436, Sellekchem, S1060) and Pol theta inhibitor Novobiocin (Sigma) were used.

Cell Survival Assay

Cells were seeded in each 6-cm dish and cultured as described above. They were treated with drugs with indicated dose in medium after seeding. After 7-10 days, colonies were fixed and stained with 0.3% crystal violet in methanol, and the number of colonies was counted manually.

We claim:

1. A method for treatment of a subject in need of a treatment for a cancer, the method comprising administering an effective amount of an RNA methyltransferase inhibitor to the subject, wherein the cancer has upregulated SYCP2 expression or upregulated SYCP2 activity.

2. A method for treatment of a subject in need of a treatment for a cancer, the method comprising administering an effective amount of an RNA methyltransferase inhibitor to the subject, wherein the cancer is a homologous recombination (HR) deficient cancer.

3. A method for treatment of a subject in need of a treatment for a breast cancer, the method comprising administering an effective amount of an RNA methyltransferase inhibitor to the subject, wherein the breast cancer is a BRCA proficient breast cancer.

4. The method of claim 1, wherein the cancer is a homologous recombination (HR) deficient cancer, the cancer is a cancer resistant to therapy with a DNA damaging agent, or a combination thereof.

5. The method of claim 1, wherein the cancer is a breast cancer, ovarian cancer, esophageal cancer, stomach cancer, colon cancer, lung cancer, skin cancer, prostate cancer, head and neck cancer, bone cancer, kidney cancer, urinary tract cancer, bladder cancer, pancreatic cancer, pediatric cancer, or blood cancer.

6. The method of claim 1, wherein the cancer is a breast cancer.

7. The method of claim 1, wherein the RNA methyltransferase inhibitor is a compound of formula

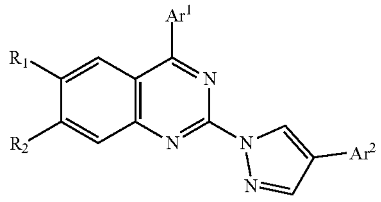

or a pharmaceutically acceptable salt thereof, wherein $R_1$ and $R_2$ are independently selected from hydrogen; an unsubstituted or substituted, unbranched or branched, saturated or unsaturated, acyclic or cyclic $C_1$-$C_6$ alkyl; hydroxide; an unsubstituted or substituted, unbranched or branched, saturated or unsaturated, acyclic or cyclic $C_1$-$C_6$ alkoxy; an unsubstituted or substituted, unbranched or branched, saturated or unsaturated, acyclic or cyclic $C_1$-$C_6$ amino; an unsubstituted or substituted aryl; or an unsubstituted or substituted heteroaryl; and wherein $Ar^1$ and $Ar^2$ are independently selected from an unsubstituted or substituted aryl or an unsubstituted or substituted heteroaryl.

8. The method of claim 7, wherein $R_1$ and $R_2$ are independently the unsubstituted or substituted, unbranched or branched, saturated or unsaturated, acyclic or cyclic $C_1$-$C_6$ alkoxy;

$Ar^1$ is the unsubstituted heteroaryl; and/or $Ar^2$ is the substituted aryl.

9. The method of claim 7, wherein $R_1$ and $R_2$ are methoxy;

$Ar^1$ is an unsubstituted thiophene; and/or $Ar^2$ is a sulfonyl substituted phenyl.

10. The method of claim 7, wherein the compound, or a pharmaceutically acceptable salt thereof, is selected from the group consisting of 6,7-dimethoxy-4-phenyl-2-(4-(pyridin-3-yl)-1H-pyrazol-1-yl)quinazoline, 6,7-dimethoxy-2-(4-(pyridin-3-yl)-1H-pyrazol-1-yl)-4-(quinolin-8-yl)quinazoline, 5-(6,7-dimethoxy-2-(4-(pyridin-3-yl)-1H-pyrazol-1-yl) quinazolin-4-yl)-N,N-dimethylpyridin-2-amine, 6,7-dimethoxy-4-(pyridin-3-yl)-2-(4-(pyridin-3-yl)-1H-pyrazol-1-yl)quinazoline, 1-(4-(6,7-dimethoxy-2-(4-(pyridin-3-yl)-1H-pyrazol-1-yl)quinazolin-4-yl)phenyl)ethanone, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(pyridin-3-yl)quinazoline, 4-(furan-3-yl)-6, 7-dimethoxy-2-(4-(4-(methylsulfonyl) phenyl)-1H-pyrazol-1-yl)quinazoline, 6,7-dimethoxy-2-(4-(4-(methylsulfonyl)phenyl)-1H-pyrazol-1-yl)-4-(thiophen-3-yl)quinazoline, 6,7-dimethoxy-2-(4-(4-(methylsulfonyl)phenyl)-1H-pyrazol-1-yl)-4-(p-tolyl)quinazoline, 2-(4-(4-(methylsulfonyl)phenyl)-1H-pyrazol-1-yl)-4-(thiophen-3-yl)quinazoline, 7-(4-ethylpiperazin-1-yl)-2-(4-(4-(methylsulfonyl)phenyl)-1H-pyrazol-1-yl)-4-(thiophen-3-yl)quinazoline, 4-(1-(6,7-dimethoxy-4-(thiophen-3-yl)quinazolin-2-yl)-1H-pyrazol-4-yl)-N-(2-(dimethylamino)ethyl)benzenesulfonamide, 6,7-dimethoxy-4-(4-((4-methylpiperazin-1-yl)sulfonyl) phenyl)-2-(4-(4-(methylsulfonyl)phenyl)-1H-pyrazol-1-yl)quinazoline, and 6,7-dimethoxy-4-(3-methoxyphenyl)-2-(4-(4-(methylsulfonyl)phenyl)-1H-pyrazol-1-yl)quinazoline.

11. The method of claim 7, wherein the RNA methyltransferase inhibitor is

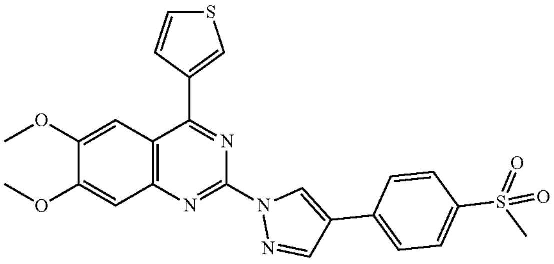 [SMILES: COc1cc2nc(-n3cc(-c4ccc(S(C)(=O)=O)cc4)cn3)nc(-c3ccsc3)c2cc1OC]

or a pharmaceutically acceptable salt thereof.

12. The method of claim 2, wherein the cancer has upregulated SYCP2 expression or upregulated SYCP2 activity, the cancer is a cancer resistant to therapy with a DNA damaging agent, or a combination thereof.

13. The method of claim 2, wherein the cancer is a breast cancer, ovarian cancer, esophageal cancer, stomach cancer, colon cancer, lung cancer, skin cancer, prostate cancer, head and neck cancer, bone cancer, kidney cancer, urinary tract cancer, bladder cancer, pancreatic cancer, pediatric cancer, or blood cancer.

14. The method of claim 2, wherein the cancer is a breast cancer.

15. The method of claim 2, wherein the RNA methyltransferase inhibitor is a compound of formula

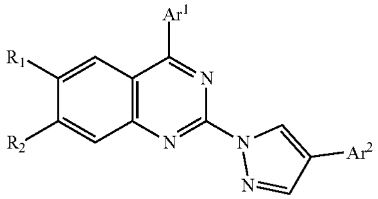

or a pharmaceutically acceptable salt thereof, wherein $R_1$ and $R_2$ are independently selected from hydrogen; an unsubstituted or substituted, unbranched or branched, saturated or unsaturated, acyclic or cyclic $C_1$-$C_6$ alkyl; hydroxide; an unsubstituted or substituted, unbranched or branched, saturated or unsaturated, acyclic or cyclic $C_1$-$C_6$ alkoxy; an unsubstituted or substituted, unbranched or branched, saturated or unsaturated, acyclic or cyclic $C_1$-$C_6$ amino; an unsubstituted or substituted aryl; or an unsubstituted or substituted heteroaryl; and wherein $Ar^1$ and $Ar^2$ are independently selected from an unsubstituted or substituted aryl or an unsubstituted or substituted heteroaryl.

16. The method of claim 15, wherein $R_1$ and $R_2$ are independently the unsubstituted or substituted, unbranched or branched, saturated or unsaturated, acyclic or cyclic $C_1$-$C_6$ alkoxy;

$Ar^1$ is the unsubstituted heteroaryl; and/or $Ar^2$ is the substituted aryl.

17. The method of claim 15, wherein $R_1$ and $R_2$ are methoxy;

$Ar^1$ is an unsubstituted thiophene; and/or $Ar^2$ is a sulfonyl substituted phenyl.

18. The method of claim 15, wherein the compound, or a pharmaceutically acceptable salt thereof, is selected from the group consisting of 6,7-dimethoxy-4-phenyl-2-(4-(pyridin-3-yl)-1H-pyrazol-1-yl)quinazoline, 6,7-dimethoxy-2-(4-(pyridin-3-yl)-1H-pyrazol-1-yl)-4-(quinolin-8-yl)quinazoline, 5-(6,7-dimethoxy-2-(4-(pyridin-3-yl)-1H-pyrazol-1-yl) quinazolin-4-yl)-N,N-dimethylpyridin-2-amine, 6,7-dimethoxy-4-(pyridin-3-yl)-2-(4-(pyridin-3-yl)-1H-pyrazol-1-yl)quinazoline, 1-(4-(6,7-dimethoxy-2-(4-(pyridin-3-yl)-1H-pyrazol-1-yl)quinazolin-4-yl)phenyl)ethanone, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(quinolin-8-yl)quinazoline, 6,7-dimethoxy-2-(4-(4-(methylsulfonyl)phenyl)-1H-pyrazol-1-yl)-4-(pyridin-3-yl)quinazoline, 4-(furan-3-yl)-6, 7-dimethoxy-2-(4-(4-(methylsulfonyl) phenyl)-1H-pyrazol-1-yl)quinazoline, 6,7-dimethoxy-2-(4-(4-(methylsulfonyl)phenyl)-1H-pyrazol-1-yl)-4-(thiophen-3-yl)quinazoline, 6,7-dimethoxy-2-(4-(4-(methylsulfonyl)phenyl)-1H-pyrazol-1-yl)-4-(p-tolyl)quinazoline, 2-(4-(4-(methylsulfonyl)phenyl)-1H-pyrazol-1-yl)-4-(thiophen-3-yl)quinazoline, 7-(4-ethylpiperazin-1-yl)-2-(4-(4-(methylsulfonyl)phenyl)-1H-pyrazol-1-yl)-4-(thiophen-3-yl)quinazoline, 4-(1-(6,7-dimethoxy-4-(thiophen-3-yl)quinazolin-2-yl)-1H-pyrazol-4-yl)-N-(2-(dimethylamino)ethyl)benzenesulfonamide, 6,7-dimethoxy-4-(4-((4-methylpiperazin-1-yl)sulfonyl) phenyl)-2-(4-(4-(methylsulfonyl)phenyl)-1H-pyrazol-1-yl)quinazoline, and 6,7-dimethoxy-4-(3-methoxyphenyl)-2-(4-(4-(methylsulfonyl)phenyl)-1H-pyrazol-1-yl)quinazoline.

19. The method of claim 15, wherein the RNA methyltransferase inhibitor is

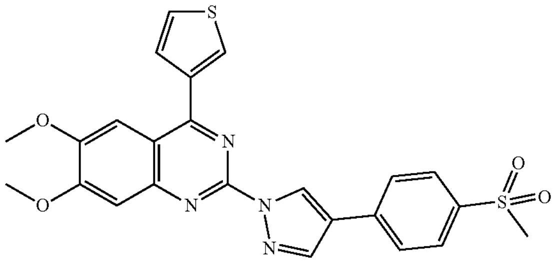

or a pharmaceutically acceptable salt thereof.

20. The method of claim 3, wherein the RNA methyltransferase inhibitor is a compound of formula

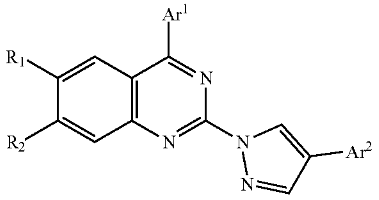

or a pharmaceutically acceptable salt thereof, wherein $R_1$ and $R_2$ are independently selected from hydrogen; an unsubstituted or substituted, unbranched or branched, saturated or unsaturated, acyclic or cyclic $C_1$-$C_6$ alkyl; hydroxide; an unsubstituted or substituted, unbranched or branched, saturated or unsaturated, acyclic or cyclic $C_1$-$C_6$ alkoxy; an unsubstituted or substituted, unbranched or branched, saturated or unsaturated, acyclic or cyclic $C_1$-$C_6$ amino; an unsubstituted or substituted aryl; or an unsubstituted or substituted heteroaryl; and wherein $Ar^1$ and $Ar^2$ are independently selected from an unsubstituted or substituted aryl or an unsubstituted or substituted heteroaryl.

* * * * *

SEQUENCE LISTING

```
<160> NUMBER OF SEQ ID NOS: 15

<210> SEQ ID NO 1
<211> LENGTH: 35
<212> TYPE: RNA
<213> ORGANISM: Artificial Sequence
<220> FEATURE:
<223> OTHER INFORMATION: Synthetic- TRIM28 siRNA

<400> SEQUENCE: 1

gcggaaaugu gagcguguac acgcucacau uuccg                              35


<210> SEQ ID NO 2
<211> LENGTH: 29
<212> TYPE: DNA
<213> ORGANISM: Artificial Sequence
<220> FEATURE:
<223> OTHER INFORMATION: Synthetic- TRDMT1-F-EcoRI

<400> SEQUENCE: 2

ccggaattct gatggagccc ctgcgggtg                                     29


<210> SEQ ID NO 3
<211> LENGTH: 33
<212> TYPE: DNA
<213> ORGANISM: Artificial Sequence
<220> FEATURE:
<223> OTHER INFORMATION: Synthetic- TRDMT1-R-BamH1

<400> SEQUENCE: 3

cgcggatcct tattcatata agattttgat tag                                33


<210> SEQ ID NO 4
<211> LENGTH: 33
<212> TYPE: DNA
<213> ORGANISM: Artificial Sequence
<220> FEATURE:
<223> OTHER INFORMATION: Synthetic- TRDMT1 K122R-F

<400> SEQUENCE: 4

cttttggaaa atgttagagg ttttgaagta tct                                33


<210> SEQ ID NO 5
<211> LENGTH: 33
<212> TYPE: DNA
<213> ORGANISM: Artificial Sequence
<220> FEATURE:
<223> OTHER INFORMATION: Synthetic- TRDMT1 K122R-R

<400> SEQUENCE: 5

agatacttca aaacctctaa cattttccaa aag                                33
```

<210> SEQ ID NO 6
<211> LENGTH: 33
<212> TYPE: DNA
<213> ORGANISM: Artificial Sequence
<220> FEATURE:
<223> OTHER INFORMATION: Synthetic- TRDMT1 K251R-F

<400> SEQUENCE: 6
agtgatctct ctgtgagaat gctaaaagat ttt 33

<210> SEQ ID NO 7
<211> LENGTH: 33
<212> TYPE: DNA
<213> ORGANISM: Artificial Sequence
<220> FEATURE:
<223> OTHER INFORMATION: Synthetic- TRDMT1 K251R-R

<400> SEQUENCE: 7
aaaatctttt agcattctca cagagagatc act 33

<210> SEQ ID NO 8
<211> LENGTH: 40
<212> TYPE: DNA
<213> ORGANISM: Artificial Sequence
<220> FEATURE:
<223> OTHER INFORMATION: Synthetic- TRDMT1 G155V-F

<400> SEQUENCE: 8
ttatctccaa cctctcttgt cattccaaat tcaaggctac 40

<210> SEQ ID NO 9
<211> LENGTH: 40
<212> TYPE: DNA
<213> ORGANISM: Artificial Sequence
<220> FEATURE:
<223> OTHER INFORMATION: Synthetic- TRDMT1 G155V-R

<400> SEQUENCE: 9
gtagccttga atttggaatg acaagagagg ttggagataa 40

<210> SEQ ID NO 10
<211> LENGTH: 25
<212> TYPE: RNA
<213> ORGANISM: Artificial Sequence
<220> FEATURE:
<223> OTHER INFORMATION: Synthetic- SYCP2 siRNA

<400> SEQUENCE: 10
guccaaggaa ucaugaugaa cuuaa 25

<210> SEQ ID NO 11
<211> LENGTH: 17
<212> TYPE: PRT
<213> ORGANISM: Artificial Sequence
<220> FEATURE:
<223> OTHER INFORMATION: Synthetic- KR

<400> SEQUENCE: 11

Lys Arg Tyr Lys Thr Lys Asp Asp Ile Lys Ser Thr Arg Lys Leu Lys
1 5 10 15

Glu

<210> SEQ ID NO 12
<211> LENGTH: 17
<212> TYPE: PRT

-continued

<213> ORGANISM: Artificial Sequence
<220> FEATURE:
<223> OTHER INFORMATION: Synthetic- M1810-8112KRAA

<400> SEQUENCE: 12

Ala Ala Tyr Lys Thr Lys Asp Asp Ile Lys Ser Thr Arg Lys Leu Lys
1 5 10 15

Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic- M1822-8272KRAA

<400> SEQUENCE: 13

Lys Arg Tyr Lys Thr Lys Asp Asp Ile Lys Ser Thr Ala Ala Ala Ala
1 5 10 15

Ala

<210> SEQ ID NO 14
<211> LENGTH: 17
<212> TYPE: PRT
<213> ORGANISM: Artificial Sequence
<220> FEATURE:
<223> OTHER INFORMATION: Synthetic- M1810-8272KRAA

<400> SEQUENCE: 14

Ala Ala Tyr Ala Ala Ala Ala Asp Ile Lys Ser Thr Ala Ala Ala Ala
1 5 10 15

Ala

<210> SEQ ID NO 15
<211> LENGTH: 21
<212> TYPE: DNA
<213> ORGANISM: Artificial Sequence
<220> FEATURE:
<223> OTHER INFORMATION: Synthetic- LV-TRDMT1-RNAi

<400> SEQUENCE: 15
gcagaagaaa ttcacaggaa a 21